United States Patent
Qian et al.

(10) Patent No.: US 11,820,762 B2
(45) Date of Patent: Nov. 21, 2023

(54) COMPOUNDS AS POTENTIAL THERAPEUTIC AGENTS TARGETING VARIOUS NEURODEGENERATIVE DISEASES

(71) Applicants: The Hong Kong University of Science and Technology, Hong Kong (CN); Southern Marine Science and Engineering Guangdong Laboratory (Guangzhou), Guangzhou (CN)

(72) Inventors: Pei-Yuan Qian, Hong Kong (CN); Aifang Cheng, Hong Kong (CN); Changdong Liu, Hong Kong (CN); Wenkang Ye, Hong Kong (CN); Guang Zhu, Hong Kong (CN)

(73) Assignees: The Hong Kong University of Science and Technology, Hong Kong (CN); Southern Marine Science and Engineering Guangdong Laboratory (Guangzhou), Guangzhou (CN)

( * ) Notice: Subject to any disclaimer, the term of this patent is extended or adjusted under 35 U.S.C. 154(b) by 108 days.

(21) Appl. No.: 17/447,784

(22) Filed: Sep. 15, 2021

(65) Prior Publication Data
US 2022/0112180 A1     Apr. 14, 2022

Related U.S. Application Data

(60) Provisional application No. 63/078,697, filed on Sep. 15, 2020.

(51) Int. Cl.
*C07D 407/12* (2006.01)
*C07D 493/04* (2006.01)

(52) U.S. Cl.
CPC ......... *C07D 407/12* (2013.01); *C07D 493/04* (2013.01)

(58) Field of Classification Search
CPC ............................ C07D 407/12; C07D 493/04
USPC ........................................................ 514/453
See application file for complete search history.

(56) References Cited

PUBLICATIONS

Chen, W.-W., et al., "Role of neuroinflammation in neurodegenerative diseases (Review)," Molecular Medicine Reports, 2016, 13:3391-3396.
Scheltens, P., et al., "Alzheimer's disease," Lancet, 2016, 388:505-517.
Hardiman, O., et al., "Amyotrophic lateral sclerosis," Nature Reviews Disease Primers, 2017, 3(17071): 1-19.
Poewe, W., et al., "Parkinson disease," Nature Reviews Disease Primers, 2017, 3(17013):1-21.
Long, J.M., et al., "Alzheimer Disease: An Update on Pathobiology and Treatment Strategies," Cell, 2019, 179:1-28.
Hou, Y., et al., "Ageing as a risk factor for neurodegenerative disease," Nature Reviews Neurology, 2019, pp. 1-17.
Eratne, D., et al., "Alzheimer's disease paper 1: clinical update on epidemiology, pathophysiology and diagnosis," Australasian Psychiatry, 2018, pp. 1-11.
Lopez, O.L., et al. "Epidemiology of aging and associated cognitive disorders: Prevalence and incidence of Alzheimer's disease and other dementias," Handbook of Clinical Neurology, 2019, 167(3):139-148.
Garre-Olmo, J., "Epidemiologia de la enfermedad de Alzheimer y otras demencias," Rev Neurol., 2018, 66(11): 377-386, along with its English abstract.
Tysnes, O.-B., et al., "Epidemiology of Parkinson's disease," Journal of Neutral Trasmission, 2017, 124:901-905.
Abbas, M. M., et al., "Epidemiology of Parkinson's Disease—East Versus West," Movement Disorders Clinical Practice, 2017, 5(1):14-28.
Rafii, M., et al., "Advances in Alzheimer's Disease Drug Development," BMC Medicine, 2015, 13(62):1-7.
Hung, S.-Y., et al., "Drug candidates in clinical trials for Alzheimer's disease," Journal of Biomedical Science, 2017, 24(47):1-12.
Witt, A., et al., "Memantine hydrochloride," Nature Reviews Drug Discovery, 2004, 3:109-110.
Reisberg, B., et al., "Memantine in Moderate-to-Severe Alzheimer's Disease," The New England Journal of Medicine, 2003, 348(14):1333-1341.
Popović, M., et al., " Neuroprotective Effect of Chronic Verapamil Treatment on Cognitive and Non Cognitive Deficits in an Experimental Alzheimer's Disease in Rats," International Journal of Neuroscience, 1997, 92(1-2):79-93.
Albarran, M. T., et al., "Endogenous rhythms of melatonin, total antioxidant status and superoxide dismutase activity in several tissues of chick and their inhibition by light," Journal of Pineal Research, 2001, 30:227-233.
Charvin, D., et al., "Therapeutic strategies for Parkinson disease: beyond dopaminergic drugs," Nature Reviews Drug Discovery, 2018, 17:804-822.
Kuller, L. H., "A new era for dementia epidemiology: Alzheimer's disease, hardening of arteries, or just old age?" European Journal of Epidemiology, 2018, 33:613-616.
Harvey, A. L., et al., "The re-emergence of natural products for drug discovery in the genomics era," Nature Reviews Drug Discovery, 2015, 14:111-129.
Haefner, B., "Drugs from the deep: marine natural products as drug candidates," Drug Discovery Today, 2003, 8(12):536-544.
Xiao, G., et al., "Chemical synthesis of marine saponins," Natural Product Reports, 2019, 36:769-787, 2019.
He, W., et al., "A Scalable Total Synthesis of the Antitumor Agents Et-743 and Lurbinectedin," Angewandte Chemie International Edition, 2019, 58:3972-3975.

(Continued)

*Primary Examiner* — Kahsay Habte
(74) *Attorney, Agent, or Firm* — Saliwanchik, Lloyd & Eisenschenk

(57) ABSTRACT

The subject invention pertains to compositions and methods for treating neurodegenerative diseases, including Alzheimer's disease (AD), Parkinson's disease (PD), amyotrophic lateral sclerosis (ALS), Huntington's disease (HD), multiple sclerosis, epilepsy, stroke, alcohol withdrawal, progressive supranuclear palsy (PSP), Pick's disease (PiD), corticobasal degeneration (CBD), frontotemporal dementia or parkinsonism linked to chromosome 17 (FTDP-17). The methods of the subject invention further relate to methods of fermentation of bacterial cells and methods of tautomerization of the subject compounds.

12 Claims, 87 Drawing Sheets

Specification includes a Sequence Listing.

(56) References Cited

PUBLICATIONS

Yamada, Y., "Studies on Discovery and Synthesis of Bioactive Marine Organic Molecules," 2002, 122(10): 727-743, along with its English abstract.

Shinde, P., et al., "Marine natural products as source of new drugs: a patent review (2015-2018)," Expert Opinion on Therapeutic Patents, 2019, pp. 1-48.

Blasco, H., et al., "The Glutamate Hypothesis in ALS: Pathophysiology and Drug Development.," Current Medicinal Chemistry, 2014, 21(1):1-26.

Mehta, A., et al., "Excitotoxicity: Bridge to various triggers in neurodegenerative disorders," European Journal of Pharmacology, 2013, 698:6-18.

Dong, X.-X., et al., "Molecular mechanisms of excitotoxicity and their relevance to pathogenesis of neurodegenerative diseases," Acta Pharmacol Sin, 2009, 30(4):379-387.

Balendra, R., et al., "C9orf72-mediated ALS and FTD: multiple pathways to disease," Nature Reviews Neurology, 2018, pp. 1-15.

Kumar, V., et al., "Unraveling the Role of RNA Mediated Toxicity of C9orf72 Repeats in C9-FTD/ALS," Frontiers in Neuroscience, 2017, 11(711):1-10.

Mazanetz, M.P., et al., "Untangling tau hyperphosphorylation in drug design for neurodegenerative diseases," Nature Reviews Drug Discovery, 2007, 6:464-479.

Julien, J.-P., "Amyotrophic Lateral Sclerosis: Unfolding the Toxicity of the Misfolded," Cell, 2001, 104:581-591.

Schneider, A., et al., "Tau-Based Treatment Strategies in Neurodegenerative Diseases," Neurotherapeutics, 2008, 5(3):443-457.

Cammas, A., et al., "RNA G-quadruplexes: emerging mechanisms in disease," Nucleic Acids Research, 2016, 45 (4):1584-1595.

Kumar, V., et al. "Structural Insight into C9orf72 Hexanucleotide Repeat Expansions: Towards New Therapeutic Targets in FTD-ALS," Neurochemistry International, 2016, pp. 1-36.

Mauger, D.M., et al., "hnRNP H and hnRNP F Complex with Fox2 To Silence Fibroblast Growth Factor Receptor 2 Exon IIIc," Molecular and Cell Biology, 2008, 28(17):5403-5419.

Lee, Y.- B., et al., "Hexanucleotide Repeats in ALS/FTD form Length-Dependent RNA Foci, Sequester RNA Binding Proteins, and Are Neurotoxic," Cell Reports, 2013, 5:1178-1186.

Zhou, B., et al., "Characterizations of distinct parallel and antiparallel G-quadruplexes formed by two-repeat ALS and FTD related GGGGCC sequence," Scientific Reports, 2018, 8:1-7.

Zhou, B., et al., "Topology of a G-quadruplex DNA formed by C9orf72 hexanucleotide repeats associated with ALS and FTD," Scientific Reports, 2015, 5:1-7.

Liu, C., et al., "A chair-type G-Quadruplex structure formed by a human telomeric variant DNA in K+ solution," Chemical Science, 2019, 10:218-226.

Liu, C., et al., "G-quadruplex structures formed by human telomeric DNA and C9orf72 hexanucleotide repeats," Biophysical Reviews, 2019, 11:389-393.

Simone, R., et al., "G-quadruplex-binding small molecules ameliorate C9orf72 FTD/ALS pathology in vitro and in vivo," EMBO Molecular Medicine, 2017, 10(1):22-31.

Selvaraj, B., et al., "C9ORF72 repeat expansion causes vulnerability of motor neurons to Ca2+-permeable AMPA receptor-mediated excitotoxicity," Nature Communications, 2018, 9:1-14.

Westergard, T., et al., "Repeat-associated non-AUG translation in C9orf72-ALS/FTD is driven by neuronal excitation and stress," EMBO Molecular Medicine, 2019, 11:1-14.

Wen, X., et al., "Tau Accumulation via Reduced Autophagy Mediates GGGGCC Repeat Expansion-Induced Neurodegeneration in *Drosophila* Model of ALS," Neuroscience Bulletin, 2020, 36(12):1414-1428.

He, H., et al., "Amyotrophic Lateral Sclerosis-associated GGGGCC repeat expansion promotes Tau phosphorylation and toxicity," Neurobiology of Disease, 2019, 130:1-10.

Kondo, K., et al., "Structure and Biosynthesis of FD-594; a New Antitumor Antibiotic," The Journal of Antibiotics, 1998, 51(3):288-295.

Kang, H.- S., et al., "Arixanythomycins A-C: Phylogeny-Guided Discovery of Biologically Active eDNA-Derived Pentangular Polyphenols," ACS Chemical Biology, 2014, 9:1267-1272.

Kang, H.-S., et al., "Mining Soil Metagenomes to Better Understand the Evolution of Natural Product Structural Diversity: Pentangular Polyphenols as a Case Study," Journal of the American Chemical Society, 2014, 136:18111-18119.

Wang, P., et al., "Identification of OxyE as an Ancillary Oxygenase during Tetracycline Biosynthesis," ChemBioChem, 2009, 10:1544-1550.

Gao, C., et al., "Hexaricins, Pradimicin-like Polyketides from a Marine Sediment-Derived *Streptosporangium* sp. and Their Antioxidant Effects," Journal of Natural Products, 2018, 81:2069-2074.

Dorst, J., et al., "Disease-modifying and symptomatic treatment of amyotrophic lateral sclerosis," Therapeutic Advances in Neurological Disorders, 2018, 11:1-16.

Donnelly, C. J., et al., "RNA Toxicity from the ALS/FTD C9ORF72 Expansion Is Mitigated by Antisense Intervention," Neuron, 2013, 80:415-428.

Starr, A., et al., "Synaptic dysfunction and altered excitability in C9ORF72 ALS/FTD," Brain Research, 2018, 1693:98-108.

Yuva-Aydemir, Y., et al., "Insights into C9ORF72-Related ALS/FTD from *Drosophila* and iPSC Models," Trends in Neurosciences, 2018, 14(7):457-469.

Selvaraj, B. T., et al., "Modeling the C9ORF72 repeat expansion mutation using human induced pluripotent stem cells," Brain Pathology, 2017, 27:518-524.

Dejesus-Hernandez, M., et al., "Expanded GGGGCC Hexanucleotide Repeat in Noncoding Region of C9ORF72 Causes Chromosome 9p-Linked FTD and ALS," Neuron, 2011, 72:245-256.

Xu, W., et al., "C9orf72 Dipeptide Repeats Cause Selective Neurodegeneration and Cell-Autonomous Excitotoxicity in *Drosophila* Glutamatergic Neurons," The Journal of Neuroscience, 2018, 38(35):7741-7752.

Dong, W., et al., "Ablation of C9orf72 together with excitotoxicity induces ALS in rats," The FEBS Journal, 2021, 288:1712-1723.

Wang, E., et al., "G-Quadruplexes as pathogenic drivers in neurodegenerative disorders," Nucleic Acids Research, 2021, 49(9):4816-4830.

Morris, G. M., et al., "Automated Docking Using a Lamarckian Genetic Algorithm and an Empirical Binding Free Energy Function," Journal of Computational Chemistry, 1998, 19(14):1639-1662.

*Streptomyces chrestomyceticus*
BCC 24770

E

F general formula-I formula-II formula-III

Groups:

$R_1$: OH; $R_2$: OH; $R_3$: OH, OCH3, OC2H5;
$R_4$: formula-II, formula-III; $R_5$: OH, OCH3, OC2H5;
$R_6$: OH; $R_7$: OH; $R_8$: OH; $R_9$: OH;

HRMS(m/z): calcd for $C_{31}H_{25}O_{14}$, 621.1239 $[M+H]^+$, found 621.1235.

1H NMR (800 MHz, Methanol-d4) δ 8.0 (d, J = 8.2 Hz, 1H), 7.8 (d, J = 7.9 Hz, 1H), 7.4 (t, J = 8.0 Hz, 1H), 6.8 (s, 1H), 6.2 (d, J = 3.7 Hz, 1H), 5.8 (d, J = 5.5 Hz, 1H), 4.3 (t, J = 4.3 Hz, 1H), 4.2 (t, J = 5.1 Hz, 1H), 2.7 (s, 1H), 1.7 (s, 2H).

$^{13}$C NMR (200 MHz, Methanol-$d_4$) δ 182.9, 170.9, 165.1, 160.1, 152.1, 150.6, 148.4, 146.4, 144.8, 142.2, 138.8, 134.2, 134.0, 125.8, 125.0, 122.7, 121.3, 120.2, 118.9, 115.2, 114.9, 113.9, 108.2, 107.6, 72.1, 68.3, 24.3, 22.9.

HRMS(m/z): calcd for $C_{32}H_{27}O_{14}$, 635.1395 $[M+H]^+$, found 635.1387.

Figures are 40% probability atom displacement ellipsoids, with labelling schemes.

COMPOUNDS AS POTENTIAL THERAPEUTIC AGENTS TARGETING VARIOUS NEURODEGENERATIVE DISEASES

CROSS-REFERENCE TO RELATED APPLICATION

This application claims the benefit of U.S. Provisional Application Ser. No. 63/078,697, filed Sep. 15, 2020, which is hereby incorporated by reference in its entirety including any tables, figures, or drawings.

SEQUENCE LISTING

The sequence listing for this application is label "HKUS-155X-Sequence.txt" which was created on Dec. 29, 2021 and is 1.83 KB. The entire contents of the sequence listing is incorporated herein by reference in its entirety.

BACKGROUND OF THE INVENTION

Neurodegenerative diseases are nervous system disorders characterized by progressive loss of neurons and degeneration of neuronal structures in the central nervous system or peripheral nervous system, with heterogeneous phenotypes. The most common neurodegenerative diseases are Alzheimer's disease (AD), Parkinson's disease (PD), and Amyotrophic lateral sclerosis (ALS)[1-4]. AD is a heterogenous nerve system disorder with complex pathobiology. For AD diagnosis, the deposition of extracellular β-amyloid plaques and intracellular neurofibrillary tangles of hyperphosphorylated tau are the most recognized pathological criteria[5]. The neuropathological hallmarks of PD are intracellular α-synuclein aggregations and dopamine neuron loss in the brain region of substantia nigra, resulting in bradykinesia and other motor disabilities[4]. ALS is a motor neuron disease characterized by upper and lower motor neuron degeneration, resulting in neuromuscular weakness and paralysis. About 50% of ALS patients present cognitive impairments and 13% develop concomitant frontotemporal dementia (FTD)[3].

Aging is a primary risk factor for these neurodegenerative diseases, all along with neuronal cell death and neuron loss. In recent decades, the aging of worldwide populations is speeding up dramatically. With the aging trend of the global community, neurodegenerative diseases with increasingly large numbers of patients, have been severely threatening human health[6]. It is estimated that one new diagnosis of AD is added every three seconds in the world. There are about 50 million AD patients in 2018, among which approximately 30 million are Chinese patients. To 2050, the number is predicted up to 152 million, three-times the current size. The global cost of AD was estimated at 1 trillion US dollars in 2018, and will be double that amount in 20307-9. PD is the second most prevalent neurodegenerative disease, and the global patient size is about 10 million in 2020, among which there are 1 million Americans and 2.5 million Chinese[10,11]. ALS, cancer, and Acquired Immune Deficiency Syndrome (AIDS) are regarded as three incurable diseases by the World Health Organization. There are more than 5000 new ALS cases diagnosed every year in the world, probably reaching 400,000 by 2040.

However, there are almost no effective drugs currently, and the present medicines targeting these diseases can only relieve symptoms without any effect on reversing neuronal damage or delaying disease progression. The existing AD drugs can be classified into several groups based on their working mechanism: for example, Tacrine and Exelon for improving central cholinergic system[12,13]; Memantine as glutamate receptor antagonist[14,15]; Nimodipine and Flunarizine for modulating calcium homeostasis[16]; vitamin E and Selegiline as antioxidants; antibodies targeting Aβ[17]; anti-inflammation steroid drugs; neurotrophins like NGF[12,13]; Nefiracetam for promoting neuron metabolism; and some traditional Chinese medicines like Huperzine A, catechin, Ginsenoside and others. All these drugs can only relieve AD-related symptoms but not inhibit the progress of the disease. As for PD therapy, the combination of L-dopa and dopamine decarboxylase inhibitors, such as Carbidopa, has been used for years. The application of L-dopa could compensate for the deficiency of dopamine signals in PD patients; however, the effect becomes weaker with the progression of the disease[18]. There are three drugs for ALS approved by the FDA: Riluzole, Edaravone, and Nuedexta. Riluzole is a glutamate receptor antagonist, while Edaravone protects neurons from free radicals. While these two drugs improve quality of life for patients, they do not prevent ALS progression. Nuedexta is used for the treatment of Pseudobulbar affect, a concomitant of ALS.

It was further shown that more than 300 drug candidates under clinical trials held by several international pharmaceutical companies failed in the past 20 years[19]. This indicates that the traditional combination of a single target with chemistry total synthesis is hard to succeed in finding effective drugs for neurodegenerative diseases. Therefore, novel ideas for developing therapeutic drugs are needed. At the end of 2019, GV-971 was established by China as an AD therapy, showing significant neuroprotective effects and improving cognition by reducing neuronal inflammation and removing Aβ depositions and tau hyperphosphorylation in the brain. The GV-971 was isolated from marine brown algae.

In recent years, more and more attention focused on drug discovery from marine natural products due to its rich diversity, structure novelty, and high bioactivity. Notably, various marine bacteria play essential roles in the marine ecosystem, leading to the discovery of novel drug lead compounds because of the unique bacterial metabolism pathways, offering a diverse database of model compounds for novel drug discovery[20,21]. With the development of advanced deep ocean work, efficient isolation and purification, high-throughput screening analysis, genetic engineering and molecular modification technologies, there is a revival of drug discovery from marine natural products[22-24]. Preclinical testing and clinical trials of marine compounds step have begun, and more countries are paying attention to the investment of ocean "blue drug library"[25]. At present, there are 29 active marine compounds approved for marketing or clinical tests, involved in treating various diseases.

Excitotoxicity caused by excess glutamate signal in neurons is an accredited account of cell death and a common pathological pathway shared by various neurodegenerative diseases, such as AD, PD, ALS, Huntington's disease (HD), multiple sclerosis, epilepsy, stroke, and alcohol withdrawal[26-28]. It was reported that the GGGGCC (G4C2) hexanucleotide repeat expansions (HRE), which forms G-quadruplex secondary structure, in the first non-coding region of the C9orf72 gene is a primary genetic cause of ALS and FTD. Furthermore, G-quadruplexes (G4s), the unique structural elements, play diverse roles in the pathogenesis of various neurological diseases, including Alzheimer's disease (AD), Parkinson's Disease (PD), ALS/FTD, Fragile X Syndrome (FXS), and Prion Disease Progressive Myoclonus Epilepsy Type I (PME1)[60]. Additionally, hyperphosphorylated tau aggregation is one of the most characteristic and frequent biomarkers of several neurodegenerative diseases, including AD, ALS, progressive supranuclear palsy (PSP), Pick's disease (PiD), corticobasal degeneration (CBD), and frontotemporal dementia and parkinsonism linked to chromosome 17 (FTDP-17)[31-33]. Therefore, pharmacological designs targeting to glutamate-caused excitotoxicity, DNA/RNA G4C2 binding, tau aggregation may be a feasible therapeutic combo strategy for such diseases[31].

It has been hypothesized that there are three possible underlying mechanisms of the ALS/FTD pathogenesis: loss of function of the C9orf72 gene, toxic RNA foci formed by recruitment of RNA binding proteins (RBPs) to the RNA G4C2 repeats, and toxic dipeptides by the repeat-associated non-ATG (RAN) translation[29,30]. In addition to the causative mechanisms, persistent glutamate-induced neuron excitotoxicity plays a major role in the pathogenesis of C9orf72 ALS/FTD[53-57]. Increased glutamate signals cause excitotoxicity and promote DPR formation, making neurons vulnerable[44,58,53]. Meanwhile, previous research showed a tight genetic association between tau aggregation and G4C2 HRE in modulating the neurodegeneration of C9orf72 ALS/FTD[45,46]. G4C2 HRE significantly increases aberrant tau aggregation in Drosophila by inhibiting autophagosome-lysosome fusion[45,46]. Therefore, the onset and progression of C9orf72 ALS/FTD is synergistically affected by the above several interconnected factors[59].

Though some progress in developing therapies for these neurodegenerative diseases has been made, the molecular mechanisms remain elusive. Therefore, novel biomarkers need to be discovered, and better design of pharmaceutical targets is needed.

BRIEF SUMMARY OF THE INVENTION

The present invention relates to neuroprotective compound chrexanthomycin A (cA) and its five analogs, as well as potential structurally-similar molecules, and the method of isolation and purification of these compounds. The present invention further pertains to the specific binding of cA and its analogs to DNA/RNA G4C2 G-quadruplex (G4), their neuroprotective bioactivities on neuronal cells from glutamate-induced excitotoxicity, the molecular mechanism in protecting neuronal cells by, for example, reducing G4C2 RNA foci toxicity, scavenging cellular reactive oxygen species (ROS), and decreasing tau aggregation related toxicity, and methods of treating ALS, AD, and other neurodegenerative diseases.

In certain embodiments, compound cA (chrexanthomycin A) and five structurally-similar analogs (chrexanthomycin B (cB), chrexanthomycin C (cC), chrexanthomycin D (cD), chrexanthomycin E (cD), chrexanthomycin F (cF)) can selectively protect cells from excitotoxicity caused cell death. In certain embodiments, a tautomerization process can result in two forms cA, cB, cC, cD, cE, or cF: an open form and a cyclic form.

In certain embodiments, cA, cB, cC, cD, cE, or cF can physically interact with DNA (G4C2)$_4$ (SEQ ID NO: 5) G-quadruplex (G4), RNA (G4C2)$_2$ (SEQ ID NO: 8) G4, RNA recognition motif (RRM) domain of RNA binding protein hnRNP H, or DNA binding proteins hnRNP F and/or hOrc6.

In certain embodiments, cA, cB, cC, cD, cE, or cF can enter eukaryotic cells without cytotoxic effects, rescue cells from glutamate excitotoxicity and diminish cellular G4C2 RNA foci.

In certain embodiments, cA, cB, cC, cD, cE, or cF can inhibit aberrant tau aggregation and/or decrease or eliminate tau fibril formation, tau oligomer formation, or tau protofibril formation.

In certain embodiments, cA, cB, cC, cD, cE or cF can penetrate blood brain barrier without hemolytic effects and rescue (G4C2)$_{29}$ (SEQ ID NO: 6) repeats-caused eye degeneration in animals.

BRIEF DESCRIPTION OF THE DRAWINGS

FIG. 1A. The bacteria strain producing the isolated fractions and (FIG. 1B) the HPLC spectrum of the isolated fractions. Cytotoxicity test of the isolated fractions (F8 (FIG. 1C), F9 (FIG. 1D), F10 (FIG. 1E), F11 (FIG. 1F), and F13 (FIG. 1G)) is provided on differentiated HT22 cells with a dose of 0, 0.1, 1, and 10 µg/ml (FIG. 1H). Cell viability was measured by MTT assay. FIG. 1I. Cytotoxicity test of the isolated fractions on HEK293T cells with a dose of 0, 1, and 10 µg/ml. Cell viability was measured by MTT assay. High-throughput screening modeling on differentiated Neuro2a cells (FIG. 1J) and Fraction 10 (F10) treatment on these models (FIG. 1K). F10 was added at the same time with the modeling drugs with different treatment concentration: KU60019: 1 µM; VE822: 0.2 µM; Etopside: 10 µM; L-glutamate: 5 mM; F10: 1 µg/ml for 24 h incubation. Cell viability was measured by MTT assay. n=4 batches of cell cultures; p values were determined by unpaired two-tailed t-tests.

FIG. 2A. Tautomerization of the chemical structure of chrexanthomycin A (cA). FIG. 2B. CD spectrum of cA and its analog, chrexanthomycin (cB). FIG. 2C. Chemical structures of chrexanthomycin B (cB), chrexanthomycin C (cC), chrexanthomycin D (cD), chrexanthomycin E (cE), and chrexanthomycin F (cF). FIG. 2D. Key HMBC, $^1$H,$^1$H-COSY and NOESY correlations of cA, cB, cC and cF. FIG. 2E. Single-crystal X-ray structures of compound cA in open (top left) and cyclic form (bottom left) and cF (top right) FIG. 2F. General chemical structures of compounds of the subject invention. Formula (I), formula (II), and formula (III) are defined herein.

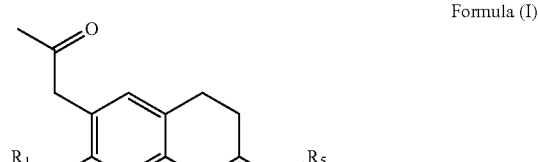

Formula (I)

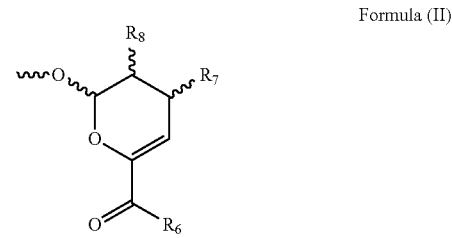

Formula (II)

-continued

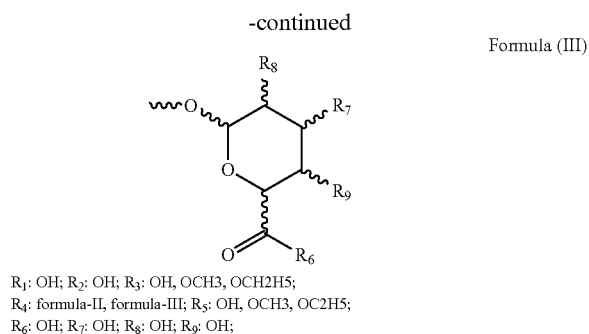

Formula (III)

Figure 3A:
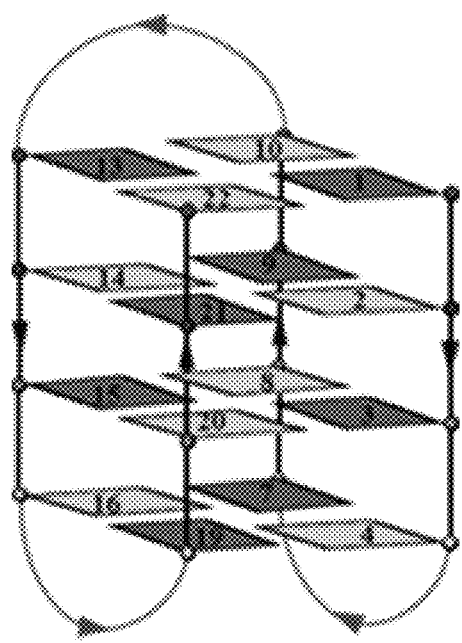
Figure 3B:
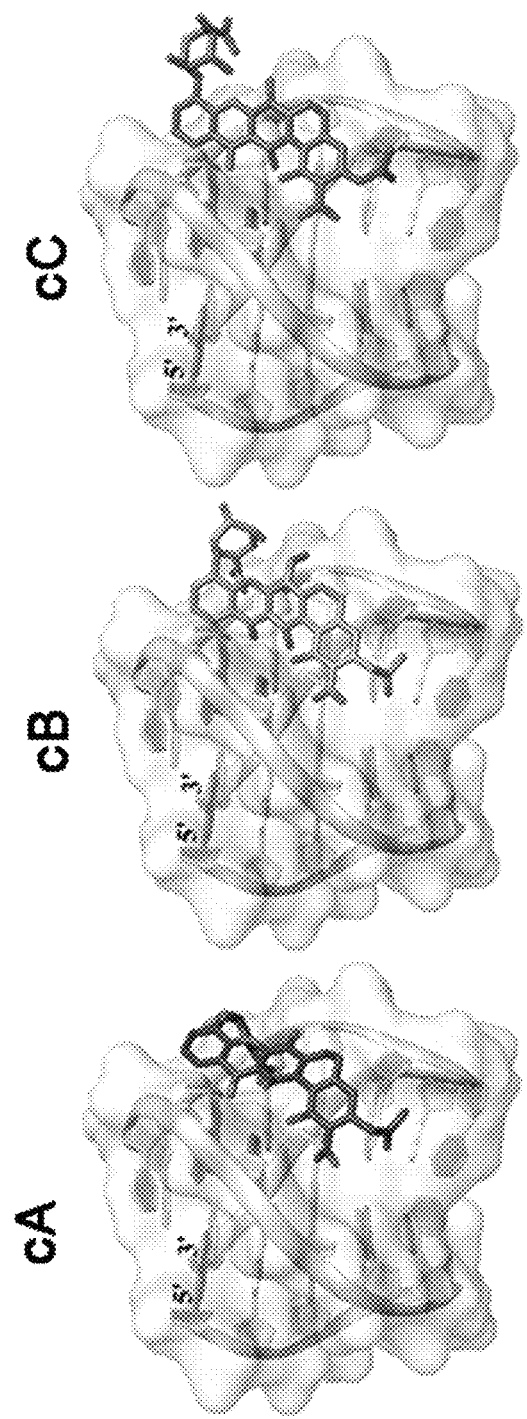
Figure 3C:
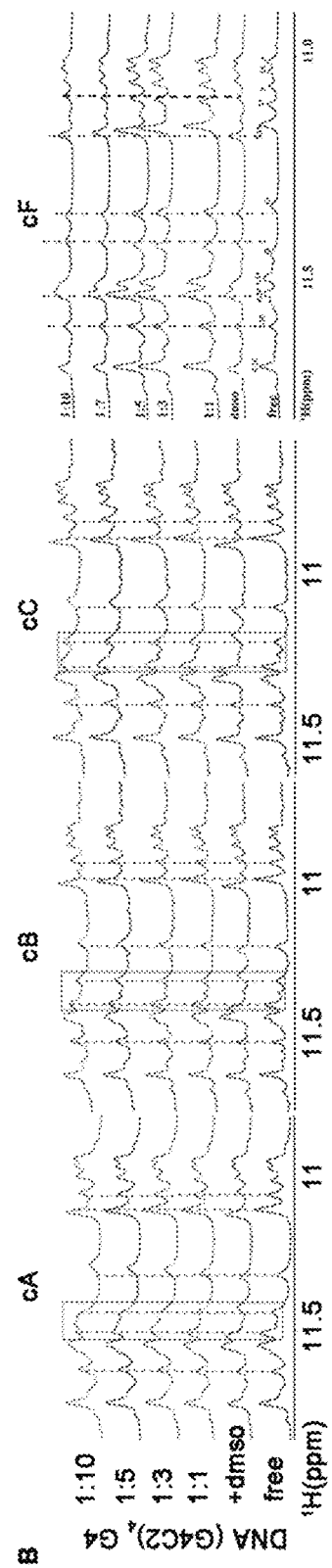
Figure 3D:
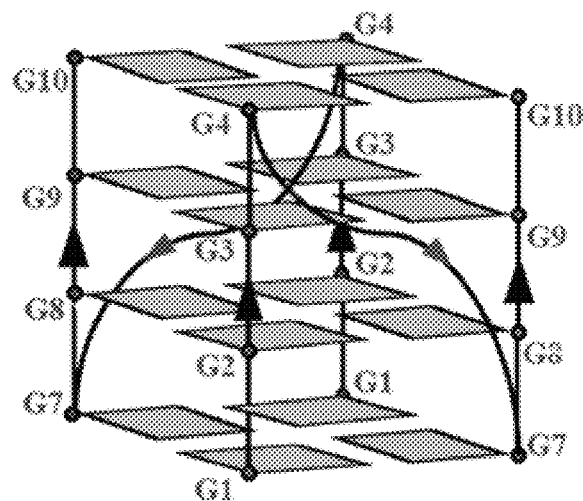
Figure 3E:
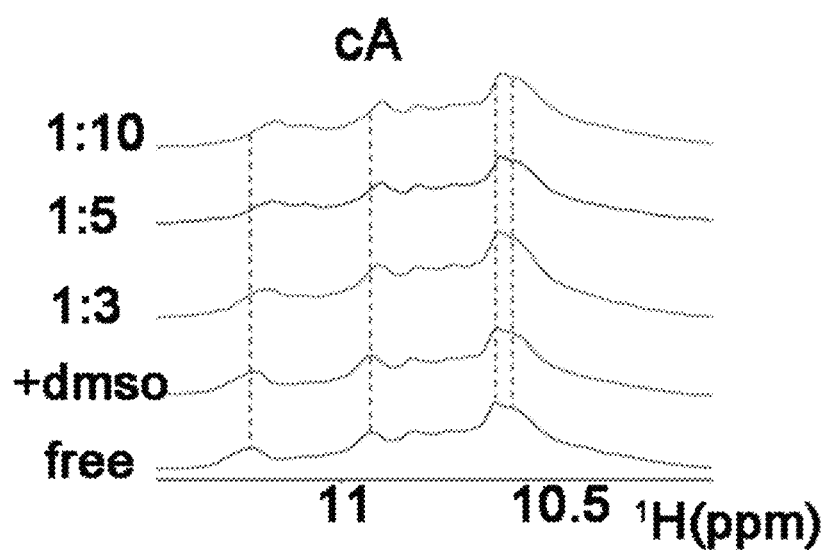
Figure 3F:
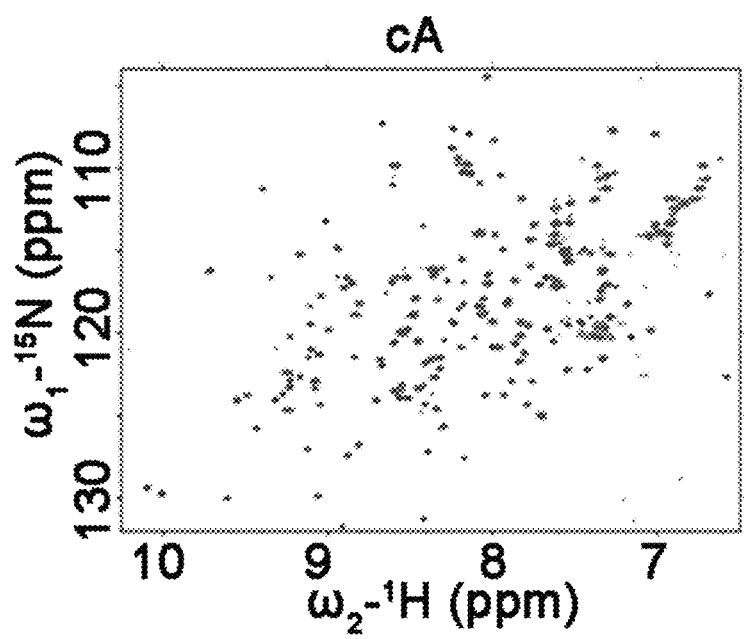
Figure 3G:
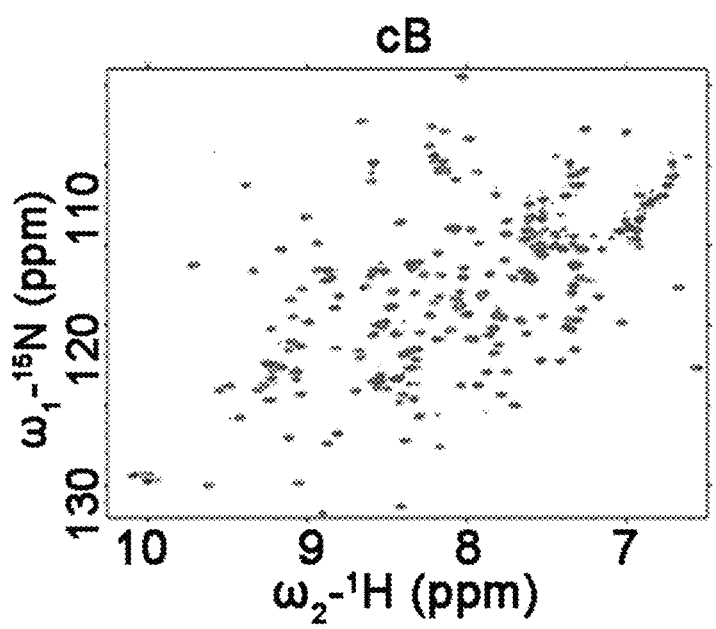
Figure 3H:
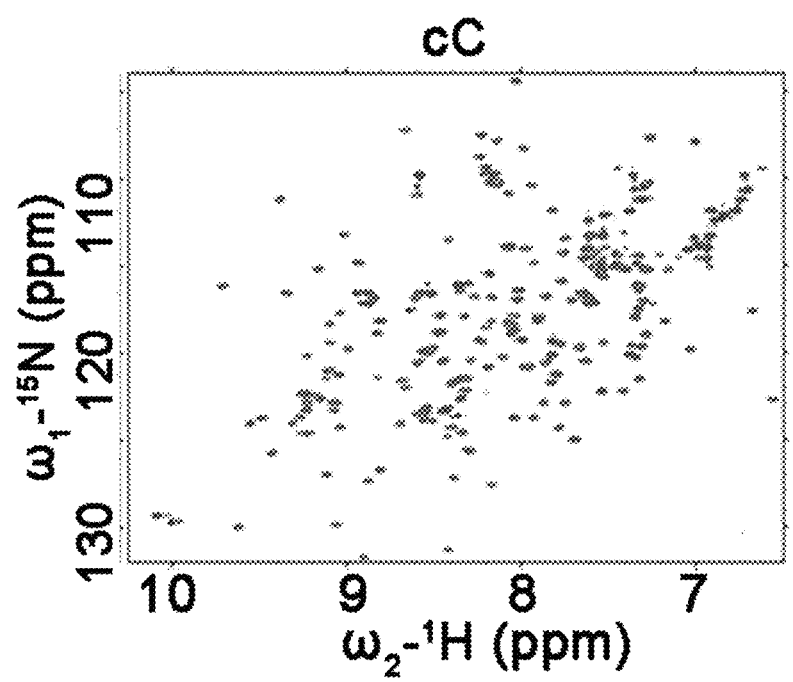
Figure 3I:
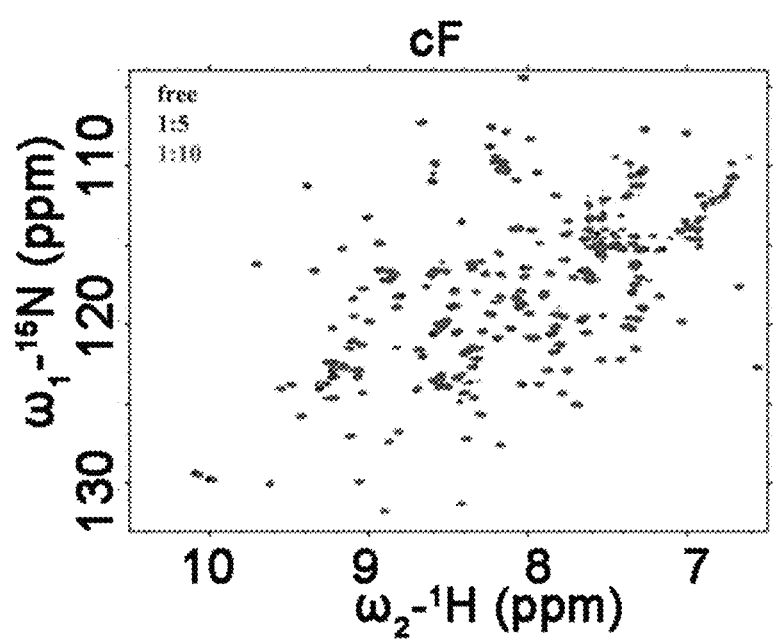

$R_1$: OH; $R_2$: OH; $R_3$: OH, OCH3, OCH2H5;
$R_4$: formula-II, formula-III; $R_5$: OH, OCH3, OC2H5;
$R_6$: OH; $R_7$: OH; $R_8$: OH; $R_9$: OH;

FIGS. 3A-3I cA, cB, cC and cF selectively bind to DNA (G4C2)$_4$ (SEQ ID NO: 5) G4 and hnRNP H. FIG. 3A. Schematic structure of DNA (G4C2)$_4$ (SEQ ID NO: 5) G4. FIG. 3B Models of predicted atomic interactions between DNA (G4C2)$_4$ (SEQ ID NO: 5) G4 (surface view) and compounds cA, cB and cC (sticks views). FIG. 3C. Imino region of 1D $^1$H-NMR spectra of DNA (G4C2)$_4$ (SEQ ID NO: 5) G4 and that titrated with compounds cA, cB, cC and cF at different ratios from 1:1 (light brown) to 1:10 (pink). FIG. 3D. Predicted schematic structure of RNA (G4C2)$_2$ (SEQ ID NO: 8) G4. FIG. 3E: Imino region of 1D $^1$H-NMR spectra of RNA (G4C2)$_2$ (SEQ ID NO: 8) G4 and that titrated with compound cA at 1:3 (green), 1:5 (blue) and 1:10 (pink) titration. Overlaid $^1$H-$^{15}$N HSQC spectra of hnRNP H RRM domain titrated with compounds cA (FIG. 3F), cB (FIG. 3G), cC (FIG. 3H) and cF (FIG. 3I) at ratios 1:0 (blue), 1:5 (green) and 1:10 (red).

Figure 4A:
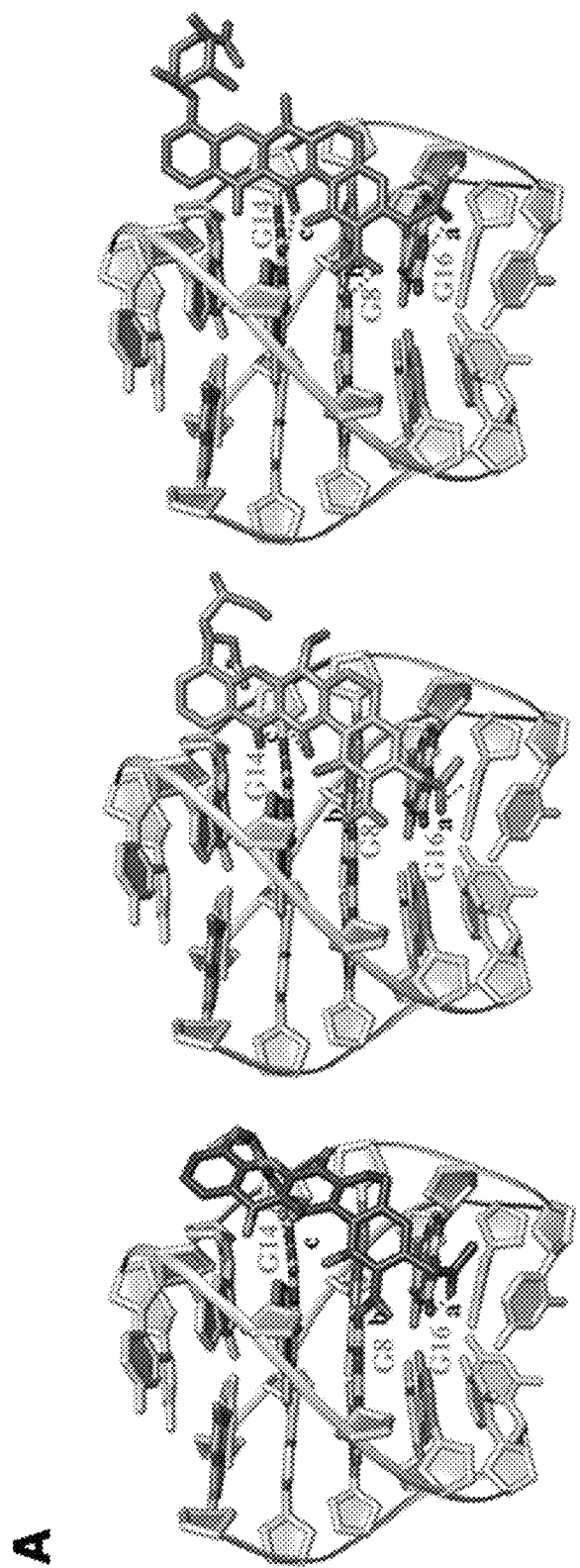
Figure 4B:
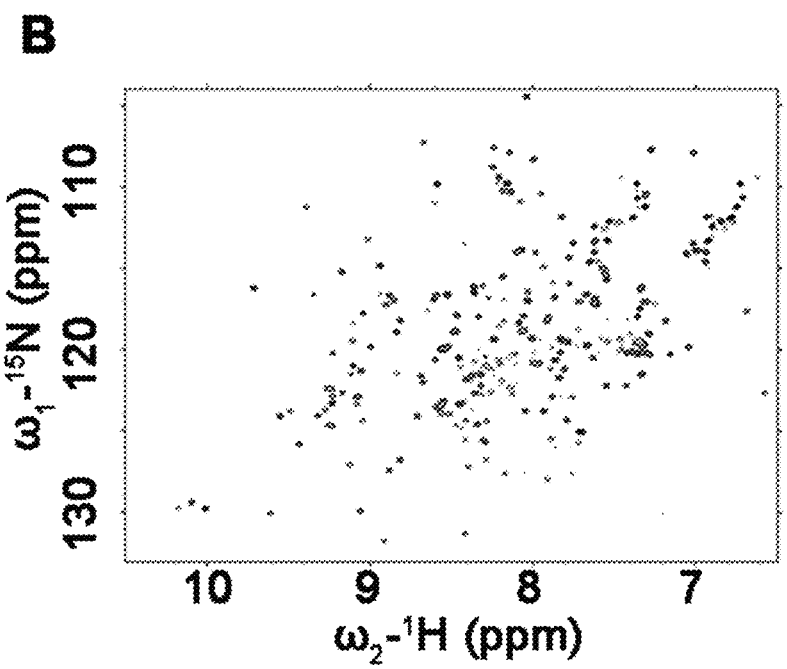
Figure 4C:
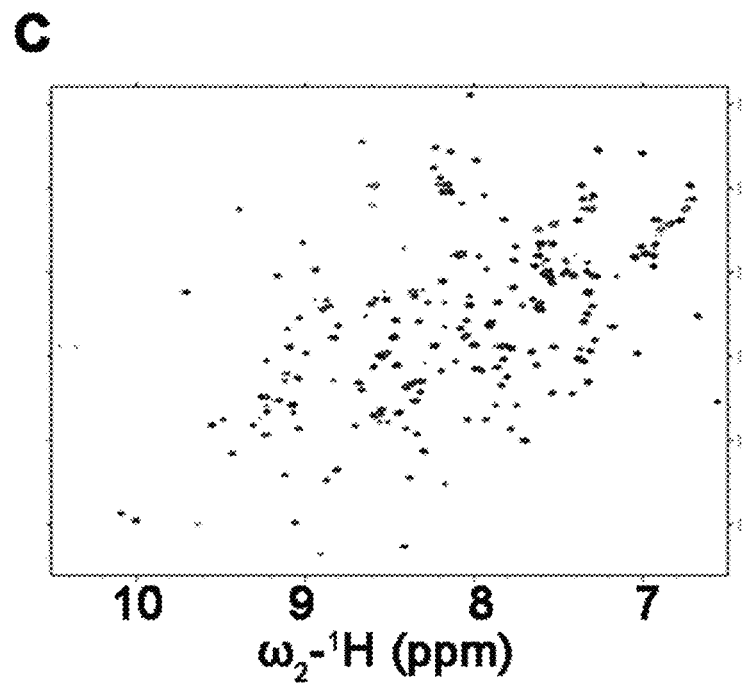

FIGS. 4A-4C Predicated interaction models and NMR titration of hnRNP H and G4s. FIG. 4A. Models of the predicted atomic interactions between DNA (G4C2)$_4$ (SEQ ID NO: 5) G4 (ribbon view) and cA (left, sticks view), cB (middle, sticks view) and cC (right, sticks view), shown with intermolecular hydrogen bonds (red dashed lines). Overlaid $^1$H-$^{15}$N HSQC spectra of hnRNP H RRM (black) and that with RNA (G4C2)$_2$ (SEQ ID NO: 8) G4 (red) (FIG. 4B) or with DNA (G4C2)$_4$ (SEQ ID NO: 5) G4 (red) (FIG. 4C) at 1:0.5 titration.

Figure 5A:
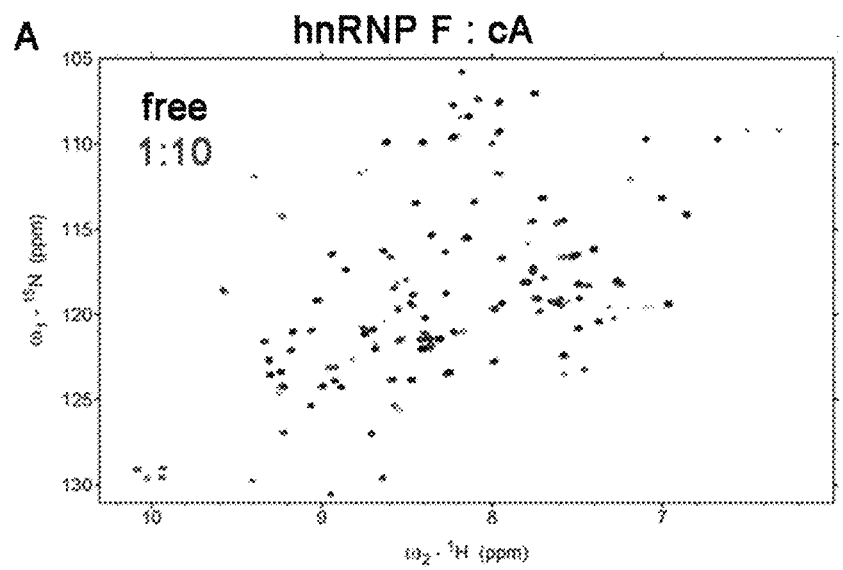
Figure 5B:
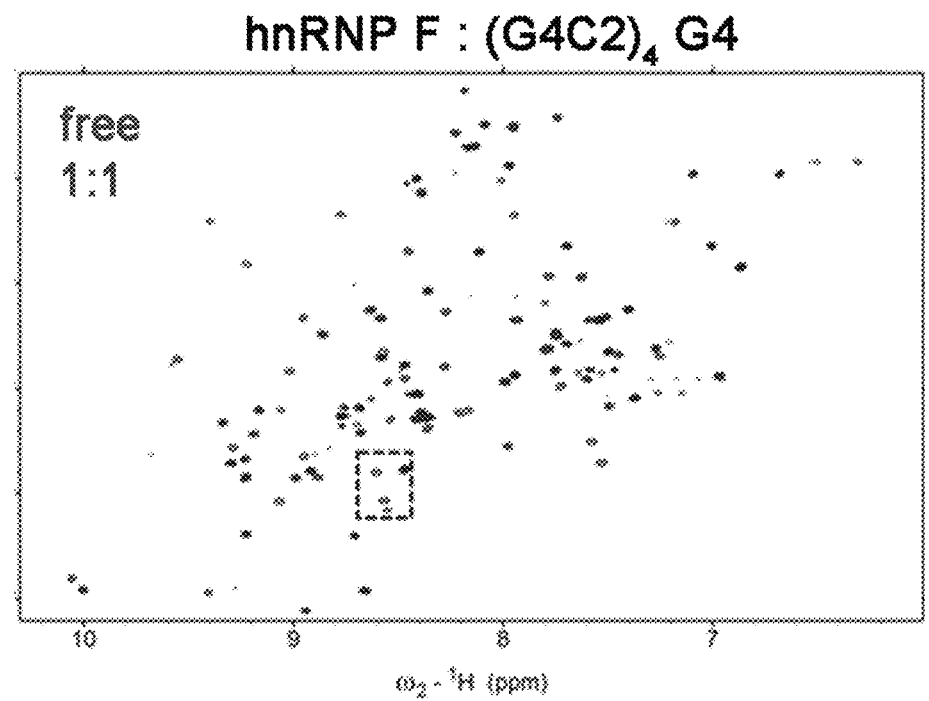
Figure 5C:
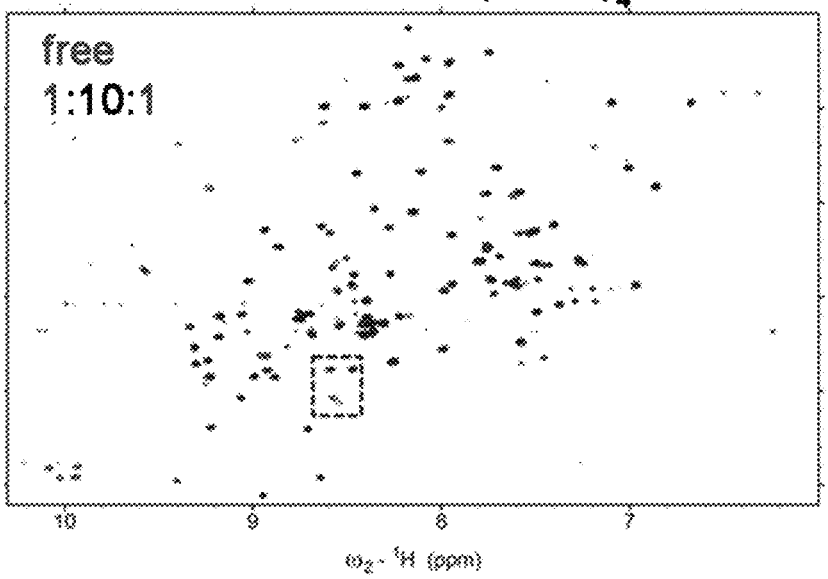
Figure 5D:
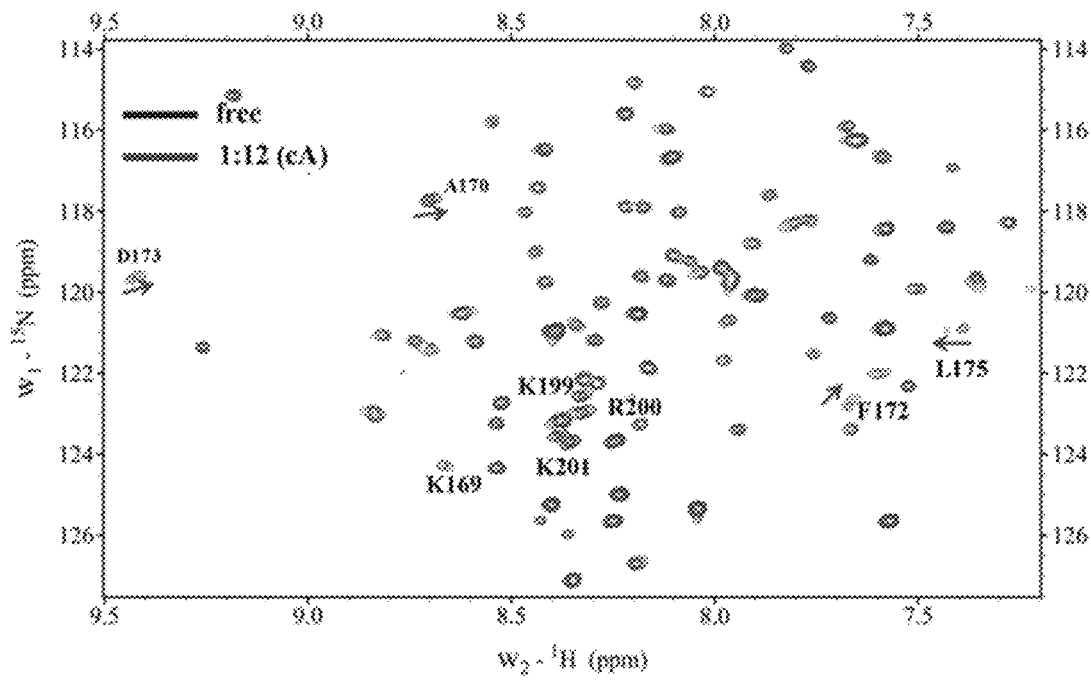

FIGS. 5A-5E cA also binds to hnRNP F and hOrc6 proteins Overlaid $^1$H-$^{15}$N HSQC spectra of hnRNP F RRM and with cA (FIG. 5A) at a 1:10 titration, with DNA (G4C2)$_4$ (SEQ ID NO: 5) G4 (FIG. 5B) at a 1:1 titration, or with cA and DNA (G4C2)$_4$ (SEQ ID NO: 5) G4 (FIG. 5C) at a 1:10:1 titration. FIG. 5D. Overlaid $^1$H-$^{15}$N HSQC spectra of human Orc6 (aa94-207) and that with cA at 1:12 titration FIG. 5E. Predicted binding sites of human Orc6 (aa94-207) for cA.

Figure 6A:
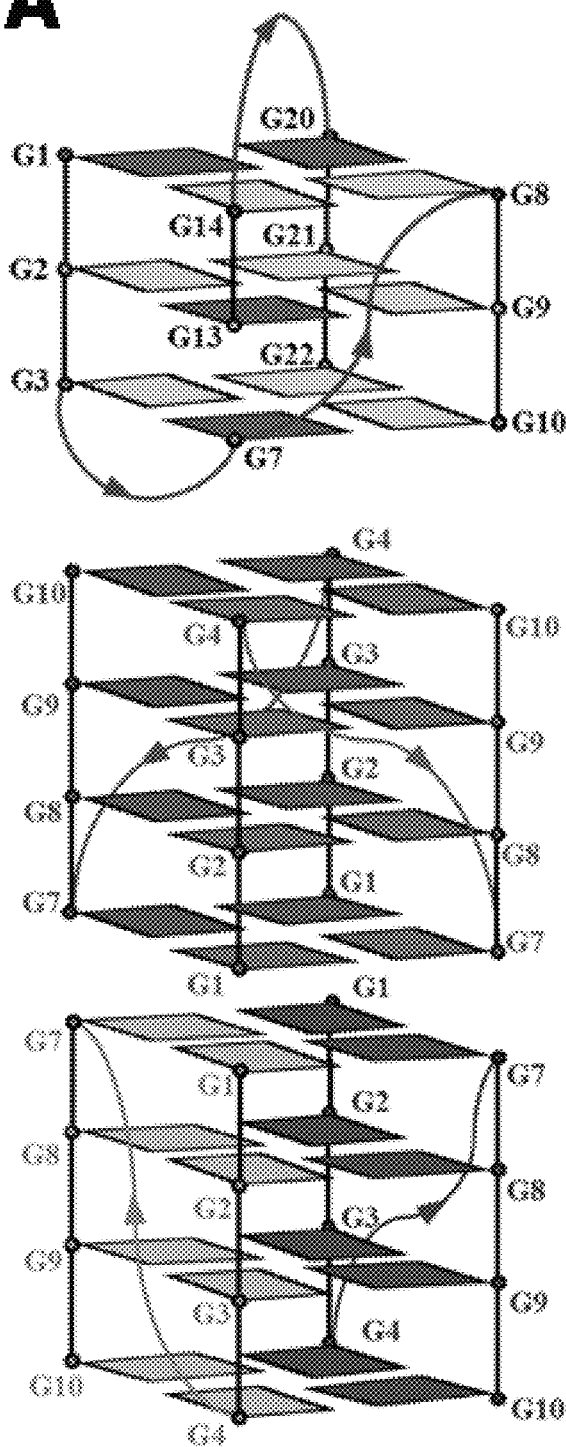
Figure 6B:
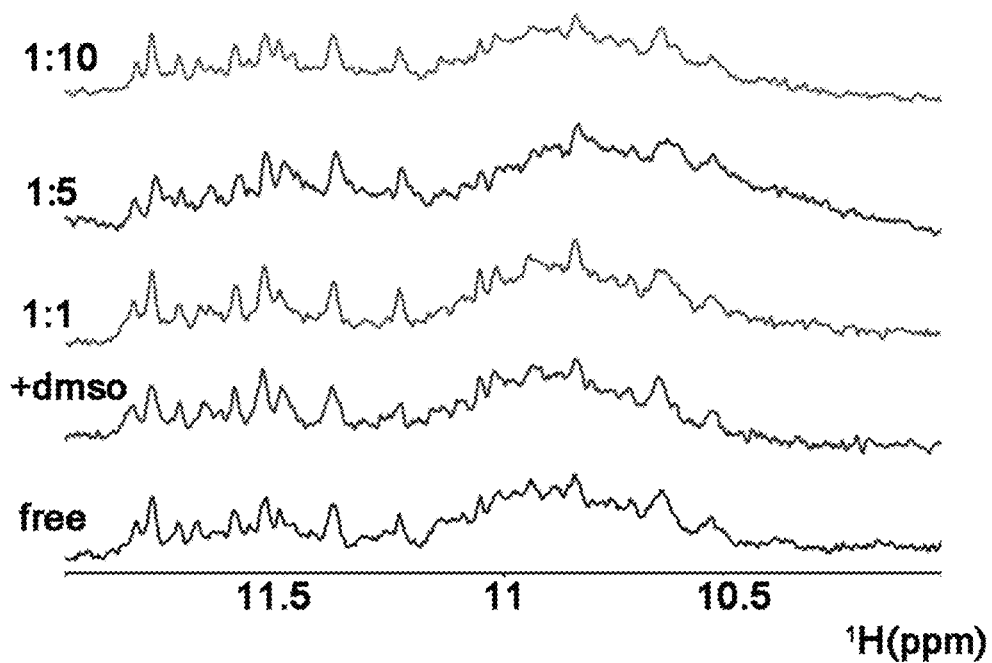
Figure 6C:
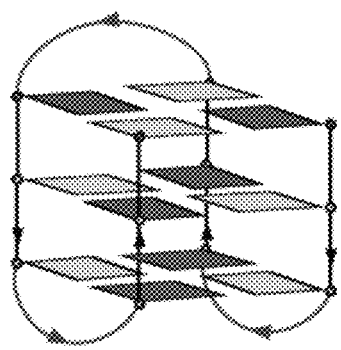
Figure 6D:
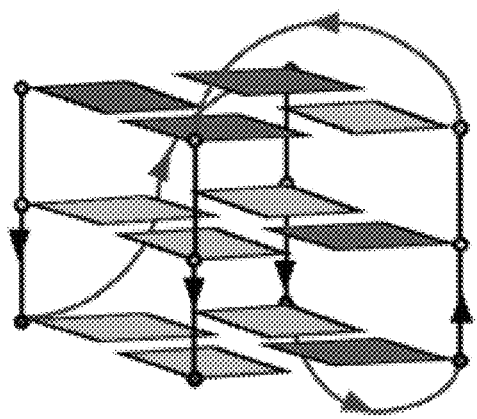
Figure 6E:
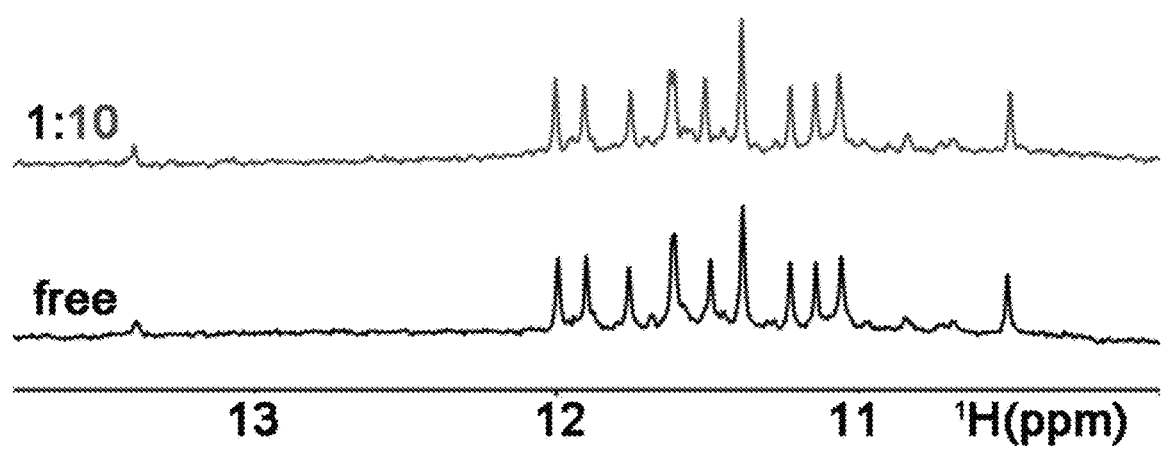
Figure 6F:
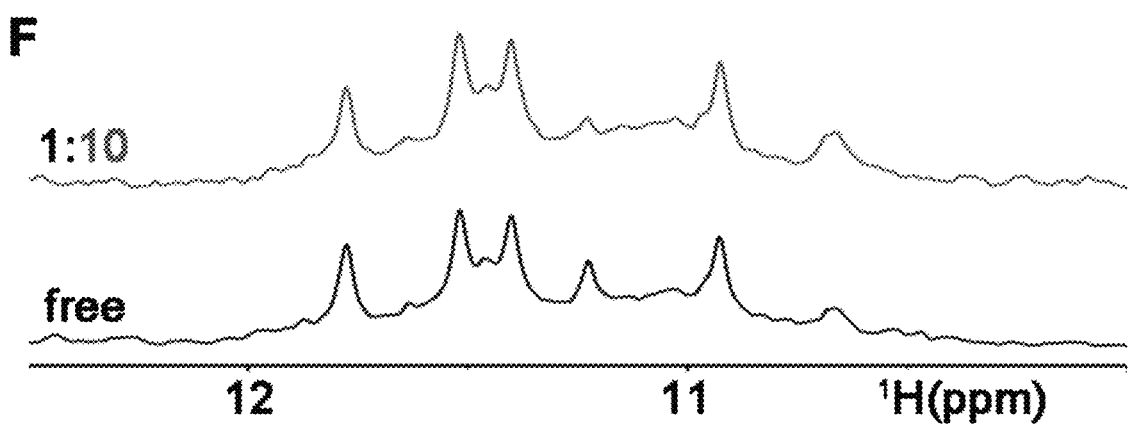
Figure 6G:
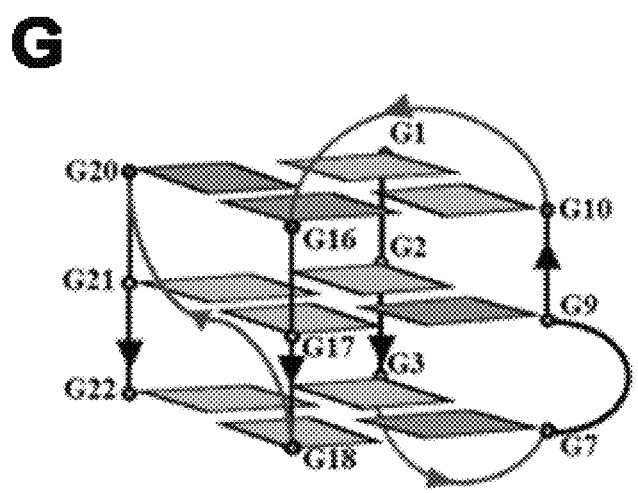
Figure 6H:
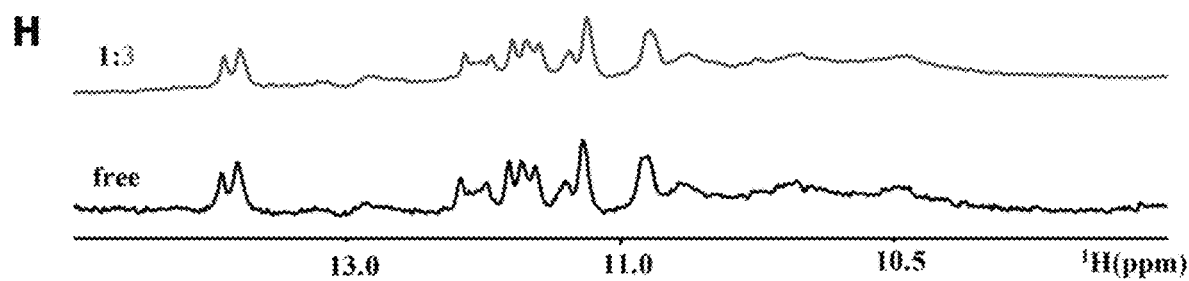

FIGS. 6A-6H Compound cA does not bind to DNA (G4C2)$_2$ (SEQ ID NO: 4) G4, human telomeric G4s or chicken G4. FIG. 6A. Predicted two types of schematic structures of DNA (G4C2)$_2$ (SEQ ID NO: 4) G4. FIG. 6B. Imino region of 1D $^1$H-NMR spectra of DNA (G4C2)$_2$ (SEQ ID NO: 4) G4 titrated with cA at 1:1 (light brown), 1:5 (blue) and 1:10 (pink) ratios. Schematic structures of human telomeric variant htel21_T18 d[(GGGTTA)$_2$GGGTTTGGG] (SEQ ID NO: 3) G4 (FIG. 6C) and human telomeric htel23 d[TA(GGGTTA)$_3$GGG] (SEQ ID NO: 7) G4 (FIG. 6D). Imino region of 1D $^1$H-NMR spectra of htel21_T18 G4 (FIG. 6E), htel23 G4 (FIG. 6F) and titrated with cA at the ratio of 1:10. FIG. 6G. Schematic structure of chicken DNA G-quadruplex. FIG. 6H. Imino region of the 1D $^1$H-NMR spectra of chicken DNA G-quadruplex and that titrated with compound cA at the ratio of 1:3.

Figure 7A:
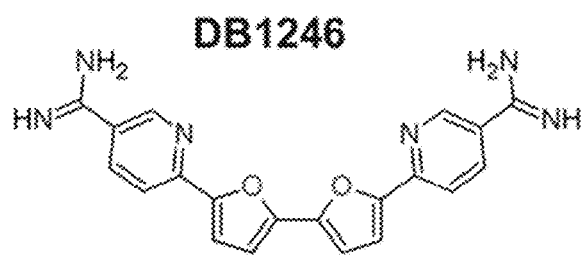
Figure 7B:
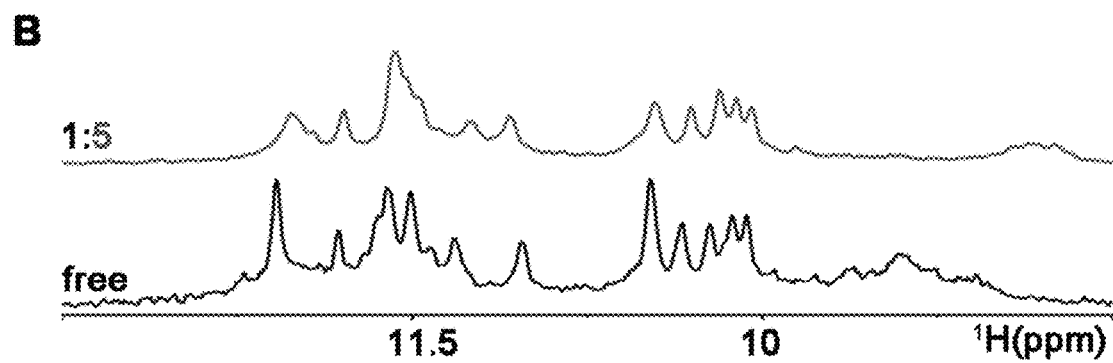
Figure 7C:
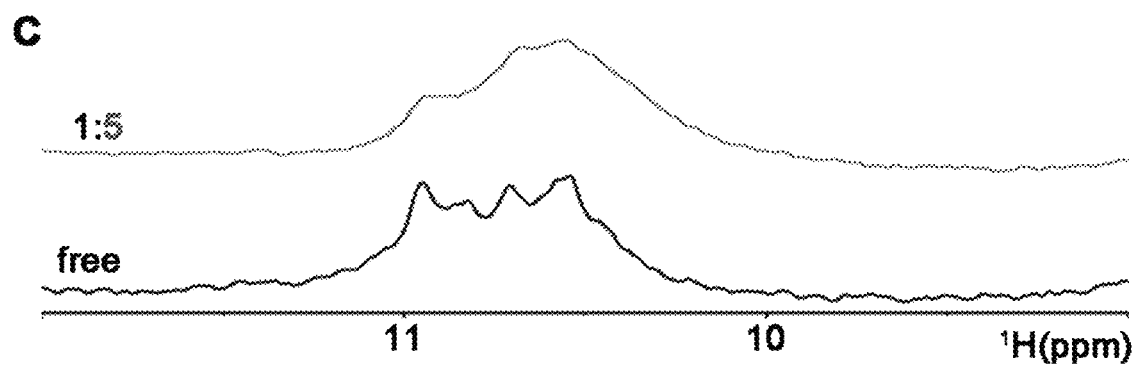
Figure 7D:
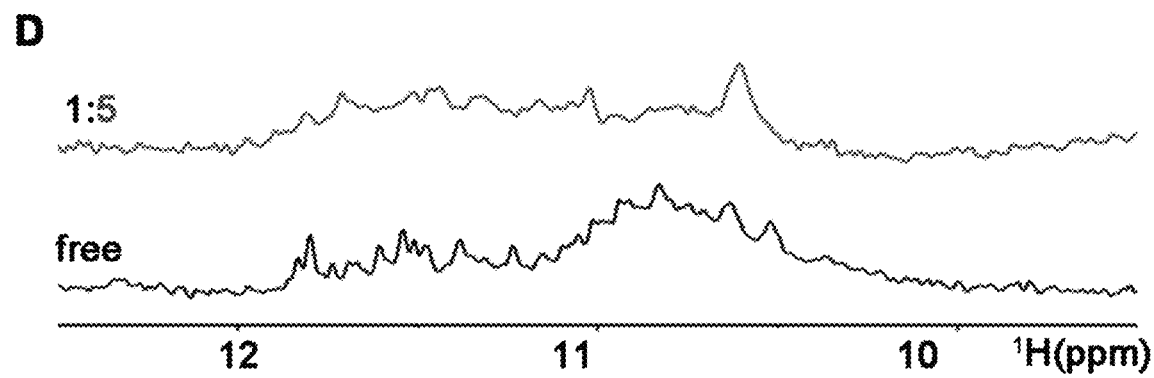
Figure 7E:
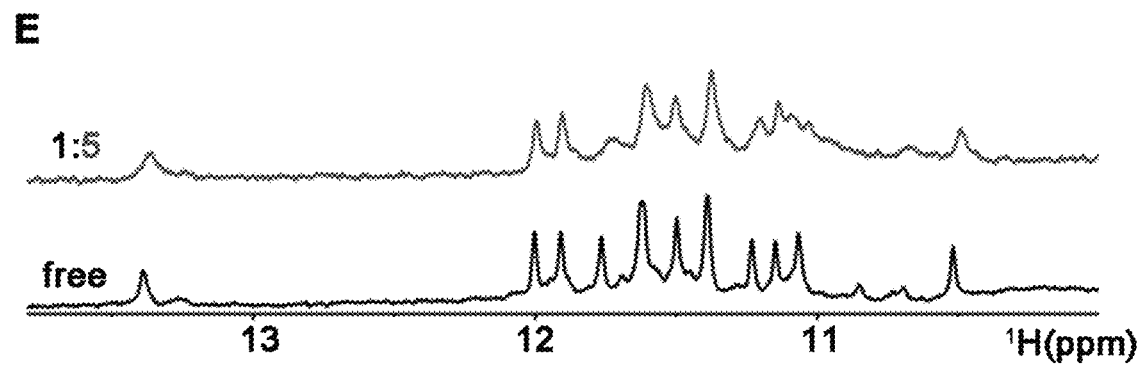

FIGS. 7A-7E DB1246 is a common ligand for all types of G4s. FIG. 7A. Chemical structure of small-molecule DB1246. Imino region of 1D $^1$H-NMR spectra of DNA (G4C2)$_4$ (SEQ ID NO: 5) G4 (FIG. 7B), RNA (G4C2)$_2$ (SEQ ID NO: 8) G4 (FIG. 7C), DNA (G4C2)$_2$ (SEQ ID NO: 4) G4 (FIG. 7D) and human telomeric htel21_T18 G4 (FIG. 7E) titrated with DB1246.

Figure 8A:
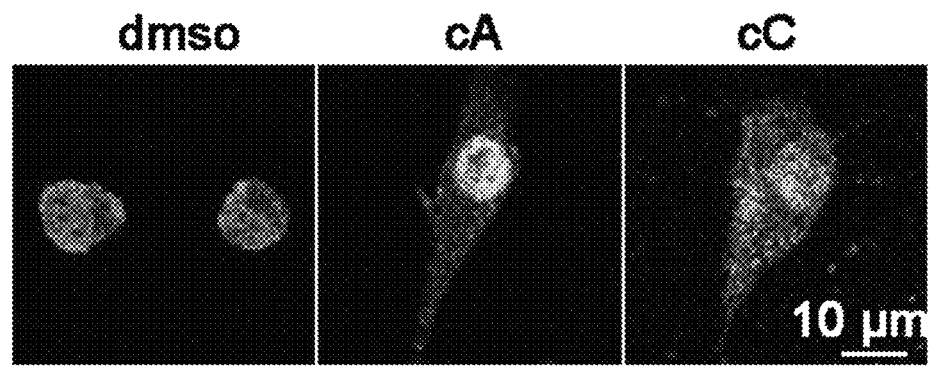
Figure 8B:
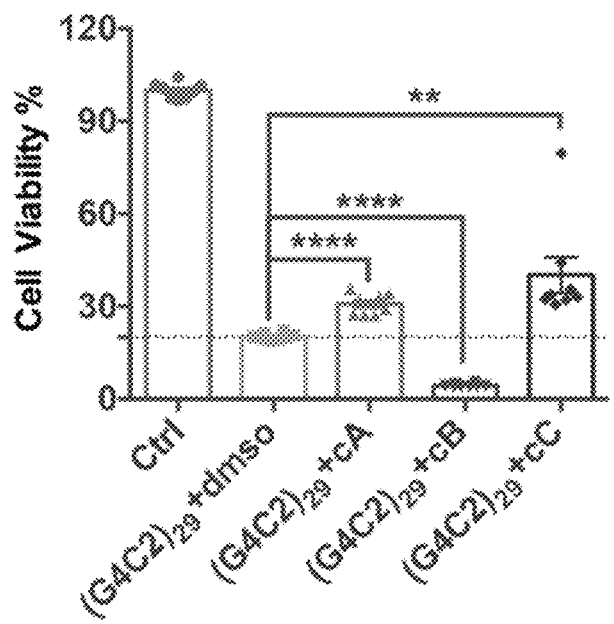
Figure 8C:
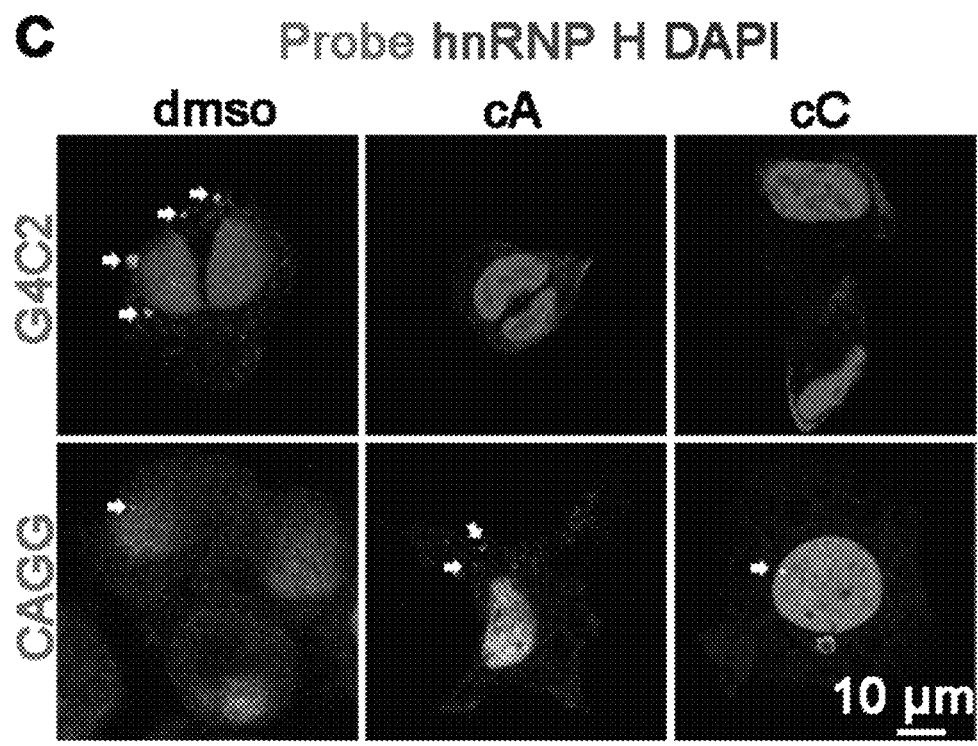
Figure 8D:
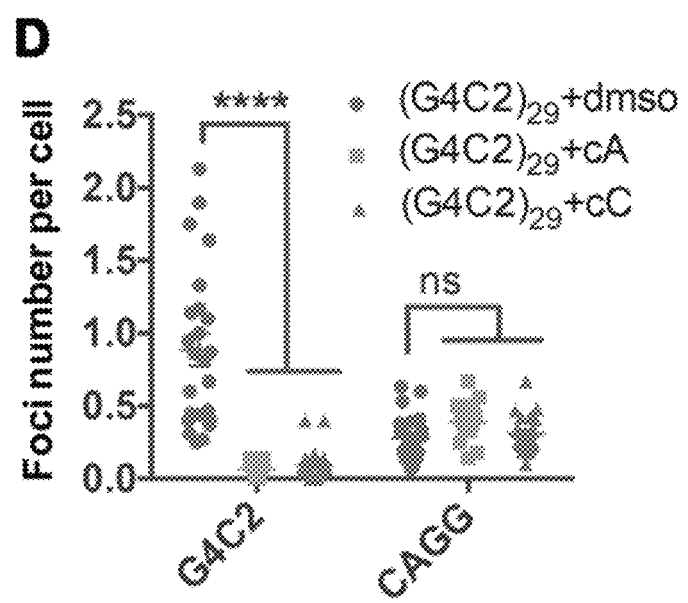
Figure 8E:
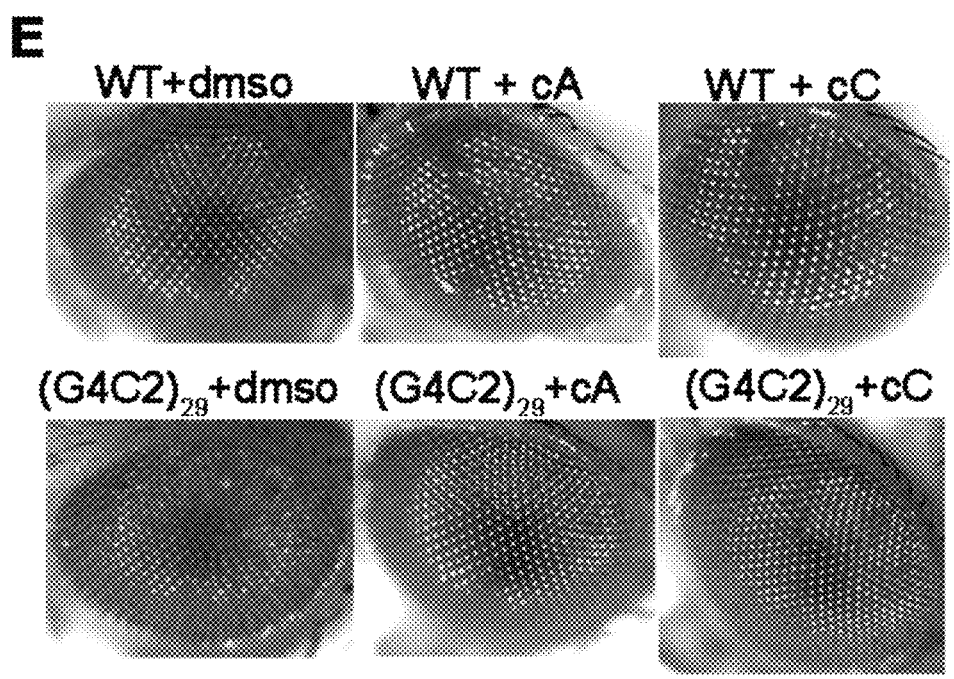
Figure 8F:
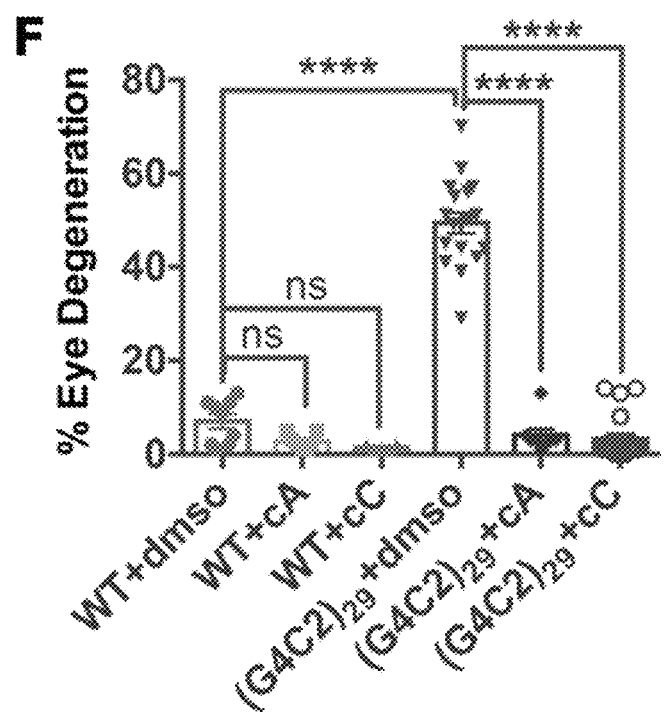

FIGS. 8A-8F Compounds cA and cC rescue G4C2 HRE-related pathologies in vitro and in vivo. FIG. 8A. Representative images of G4 antibody (green) labelled Neuro2a cells transfected with DNA (G4C2)$_{29}$ (SEQ ID NO: 6) without (left) or with cA (middle), cC (right) treatments. DAPI was used as counterstain (red). FIG. 8B. Cell viability of cA, cB and cC (1 µg/mL) treated Neuro2a cells transfected with DNA (G4C2)$_{29}$ (SEQ ID NO: 6). n=8 batches of cell cultures; p values were determined by unpaired two-tailed t-tests. FIG. 8C. Representative RNA fluorescent in situ hybridization (FISH) coupled hnRNP H (red) immunostaining images of Neuro2a cells transfected with DNA (G4C2)$_{29}$ (SEQ ID NO: 6) and that treated with cA or cC. The RNA foci of G4C2 and CAGG repeats were detected with corresponding fluorescent probes (green). DAPI was used as counterstain (blue). FIG. 8D. Quantification of G4C2 and CAGG RNA foci numbers per cell in (G4C2)$_{29}$ (SEQ ID NO: 6) expressed cells treated with cA or cC. n=17-25 coverslips from three batches of cell cultures; p values were determined by one-way ANOVA (Tukey's multiple comparisons test). FIG. 8E. Representative external eye images of 7 days after eclosion WT and GMR-GAL4-(G4C2)$_{29}$ (SEQ ID NO: 6) Drosophila fed with DMSO or compound cA, cC during the larval stage. FIG. 8F. Quantification of the eye degeneration percentage of Drosophila shown in panel e. n=7-18 animals; p values were determined by one-way ANOVA (Tukey's multiple comparisons test). All data are mean±s.e.m.

Figure 9A:
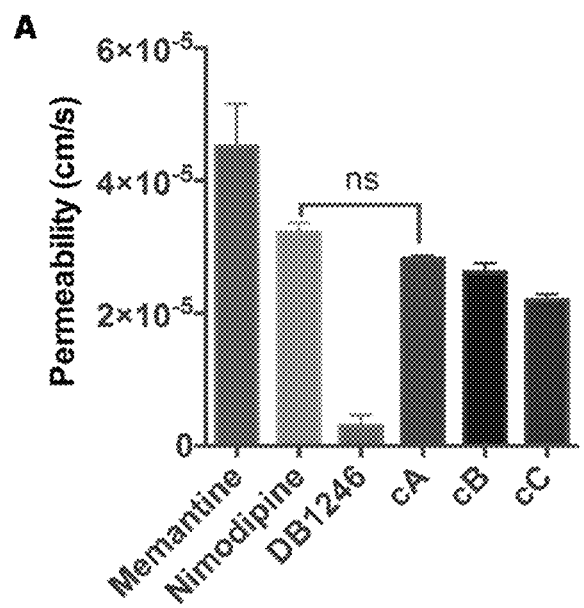
Figure 9B:
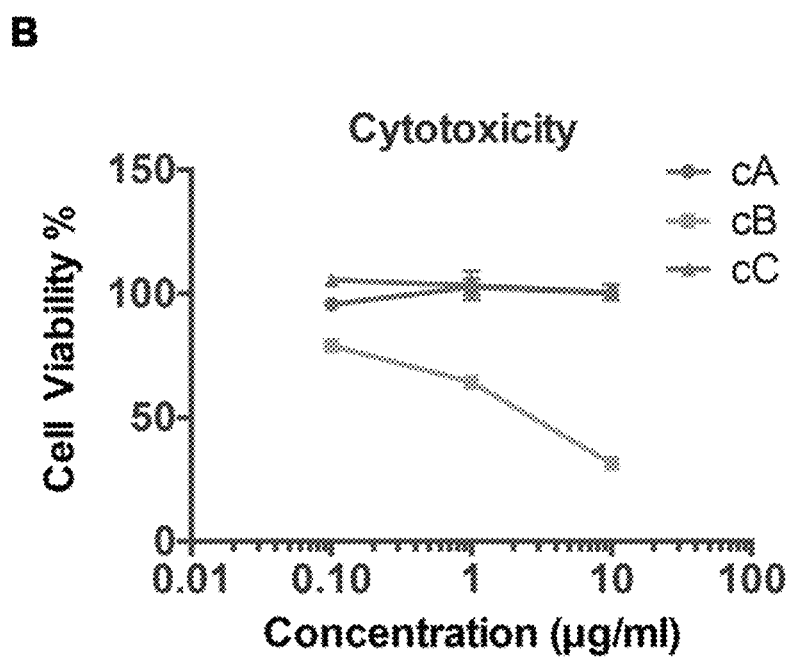
Figure 9C:
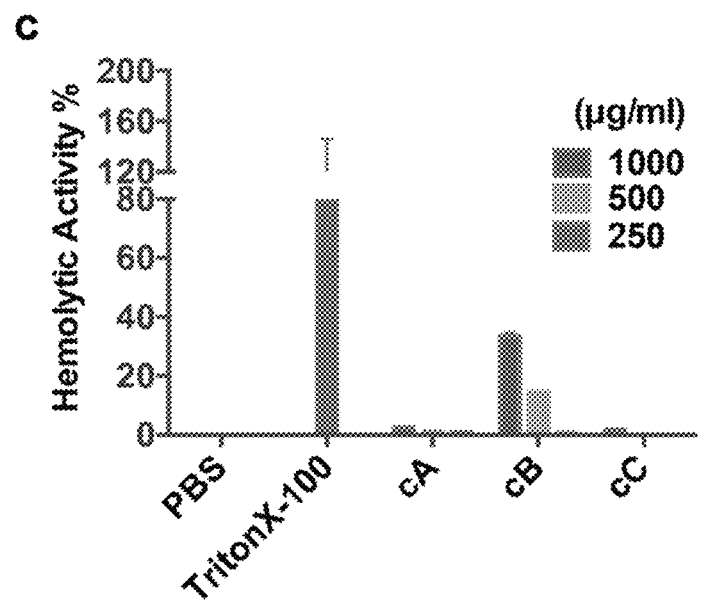

FIGS. 9A-9C Safety evaluations of cA, cB and cC. FIG. 9A. Permeability (cm/s) of memantine, nimodipine, DB1246, cA, cB and cC. n=5 batches of cell cultures; p values were determined by one-way ANOVA (Tukey's multiple comparisons test). FIG. 9B. Cytotoxicity of cA, cB and cC tested at concentrations of 0.1, 1 and 10 µg/mL on HEK293T cells. n=4 batches of cell cultures. FIG. 9C. Hemolytic activity of cA, cB and cC tested at 0, 250, 500 and 1000 µg/mL. PBS and TritonX-100 served as negative and positive controls, respectively. n=3 independent preparations. All data are mean±s.e.m.

Figure 10A:
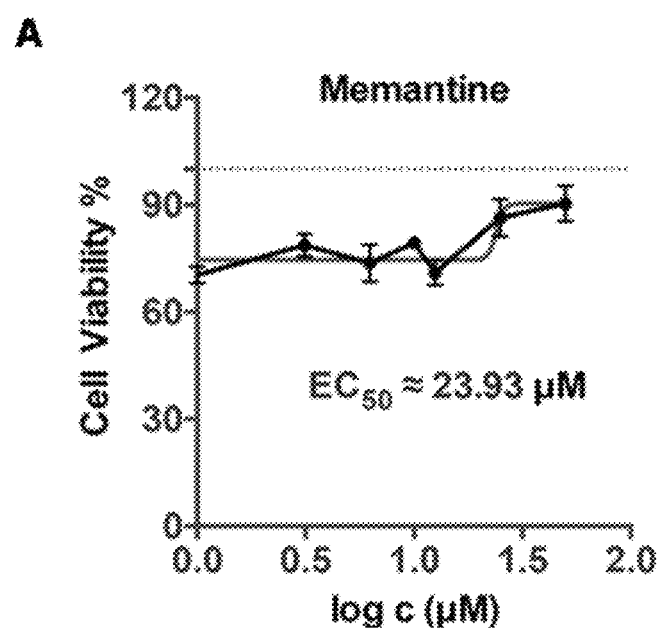
Figure 10B:
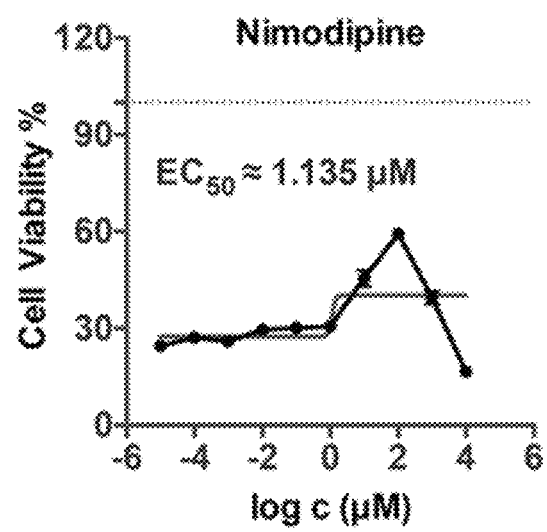
Figure 10C:
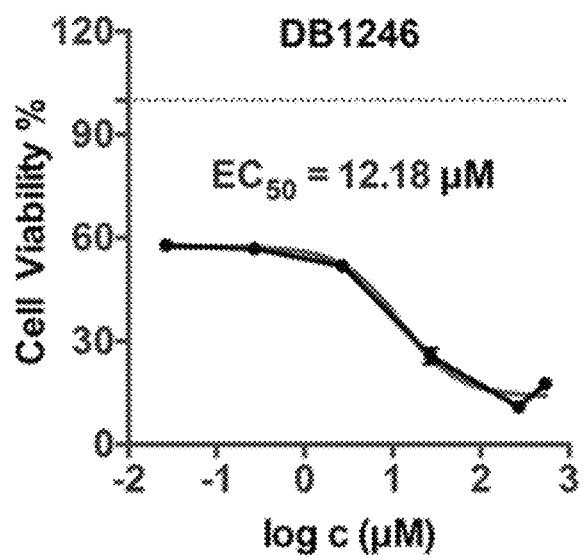
Figure 10D:
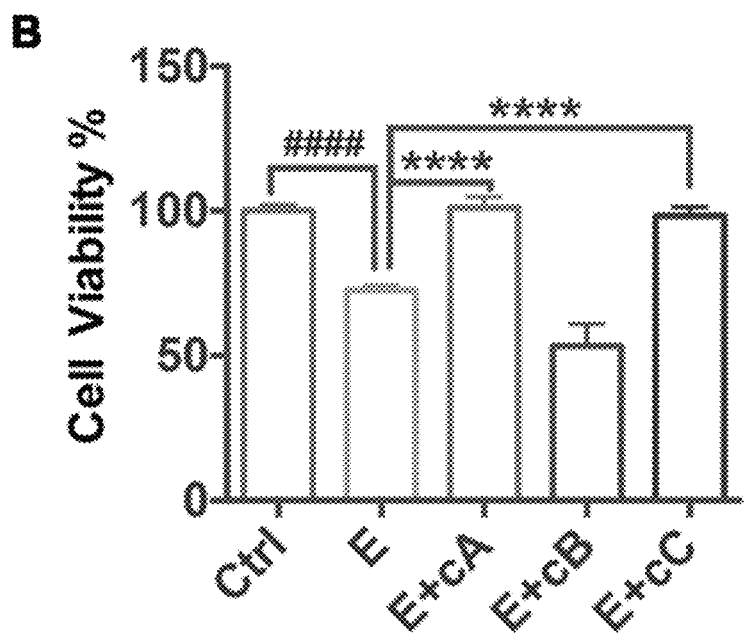
Figure 10E:
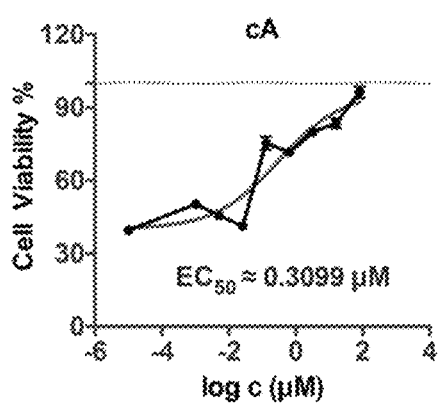
Figure 10F:
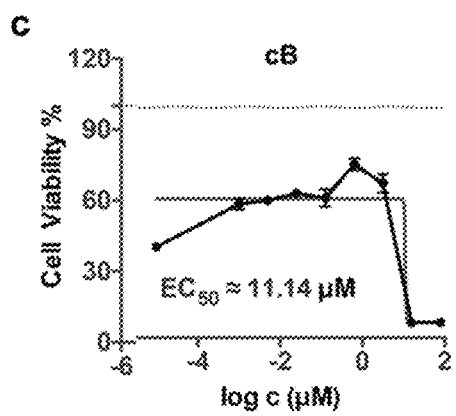
Figure 10G:
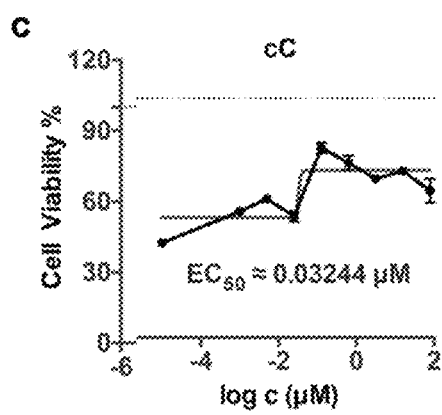
Figure 10H:
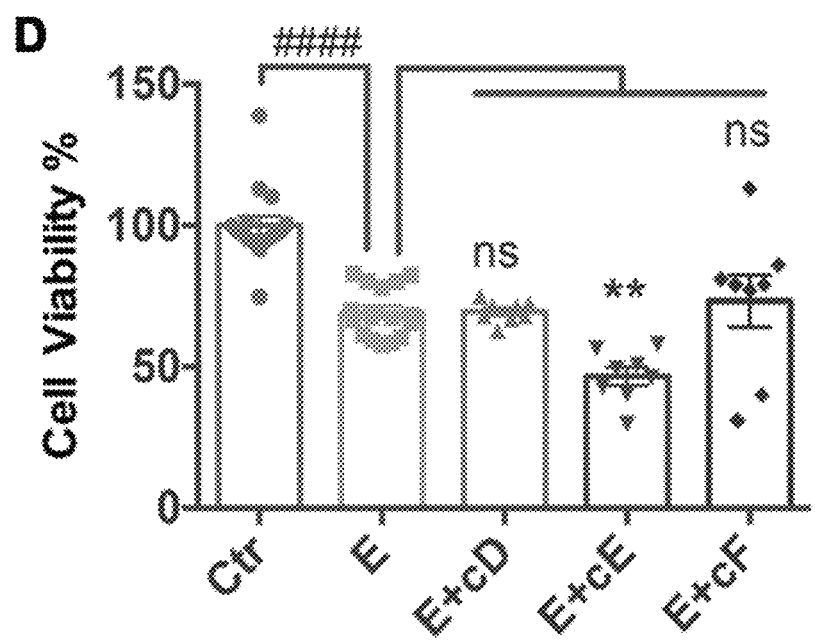
Figure 10I:
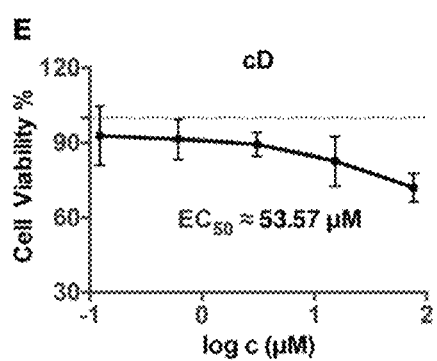
Figure 10J:
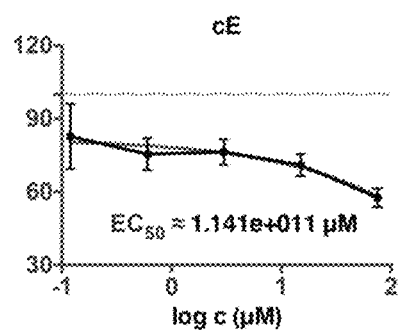
Figure 10K:
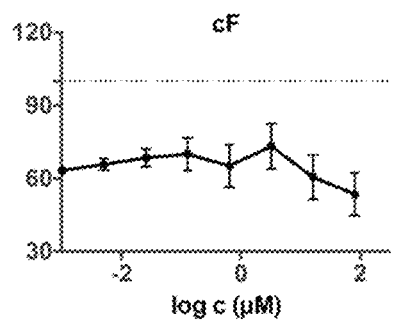

FIGS. 10A-10K Compounds cA and cC protect differentiated HT22 cells from glutamate-induced excitotoxicity. Dose-response curves (x: log concentration, y: cell viability) of memantine (FIG. 10A), nimodipine (FIG. 10B), and DB1246 (FIG. 10C) tested on differentiated HT22 cell cultures pre-treated with 5 mM L-glutamate. n=3-8 independent preparations; $EC_{50}$ values were calculated by non-linear regression (variable slope). FIG. 10D. Cell viability of compounds cA, cB and cC (1 µg/mL)-treated differentiated HT22 cells pre-treated with 5 mM L-glutamate. n=15-38 wells from three batches of cell cultures; p values were determined by one-way ANOVA (Tukey's multiple comparisons test). Dose-response curves (x: log concentration, y: cell viability) of cA (FIG. 10E), Cb (FIG. 10F), and cC (FIG. 10G) tested on differentiated HT22 cell cultures pre-treated with 5 mM L-glutamate. n=3-8 independent preparations; $EC_{50}$ values were calculated by non-linear regression (variable slope). FIG. 10H. Cell viability of compounds cD, cE and cF (1 µg/mL)-treated differentiated HT22 cells pre-treated with 5 mM L-glutamate. n=8-13 wells from three batches of cell cultures; p values were determined by one-way ANOVA (Tukey's multiple comparisons test). Dose-response curves (x: log concentration, y: cell viability) of cD (FIG. 10I), cE (FIG. 10J), and cF (FIG. 10K) tested on differentiated HT22 cell cultures pre-treated with 5 mM L-glutamate. n=3-8 independent preparations; $EC_{50}$ values were calculated by non-linear regression (variable slope).

Figure 11A:
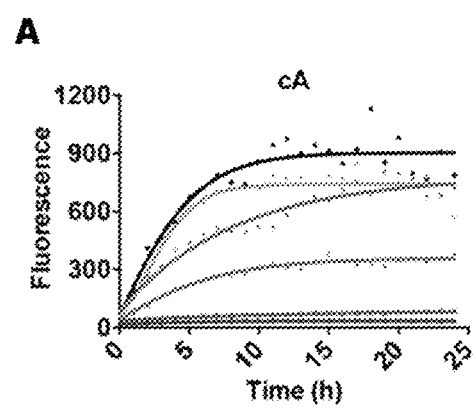
Figure 11B:
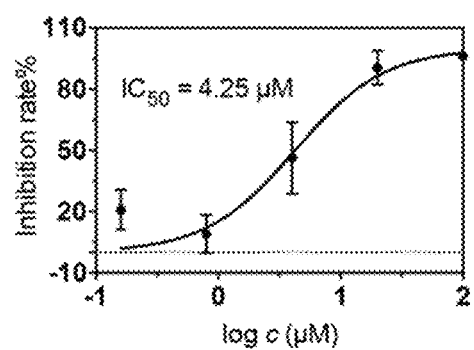
Figure 11C:
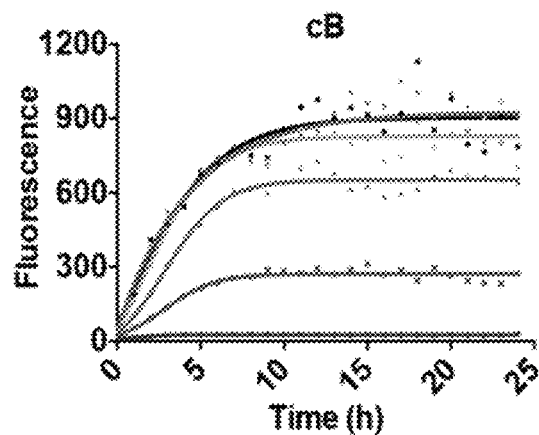
Figure 11D:
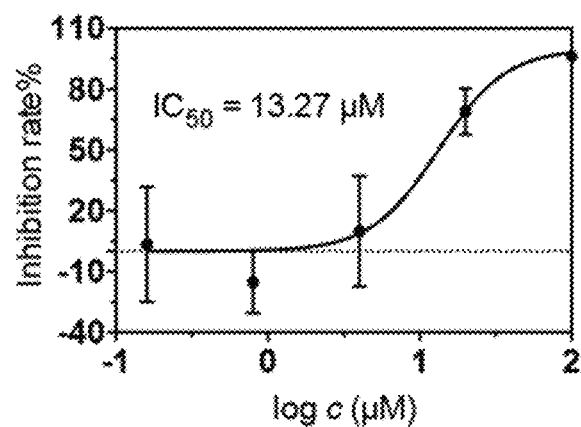
Figure 11E:
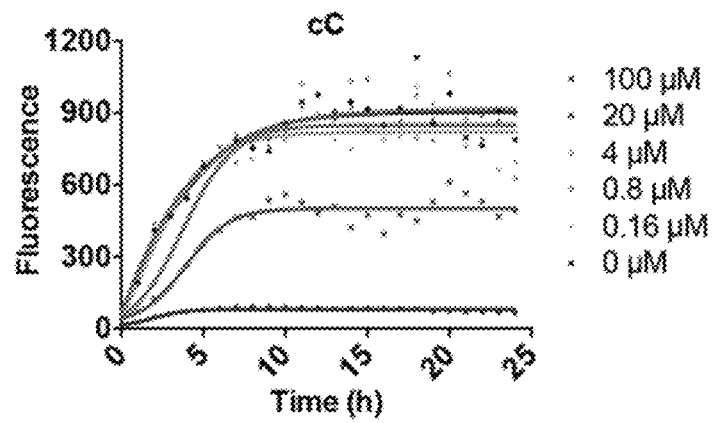
Figure 11F:
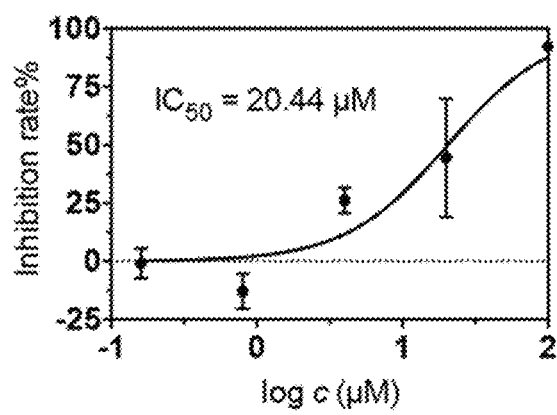
Figure 11G:
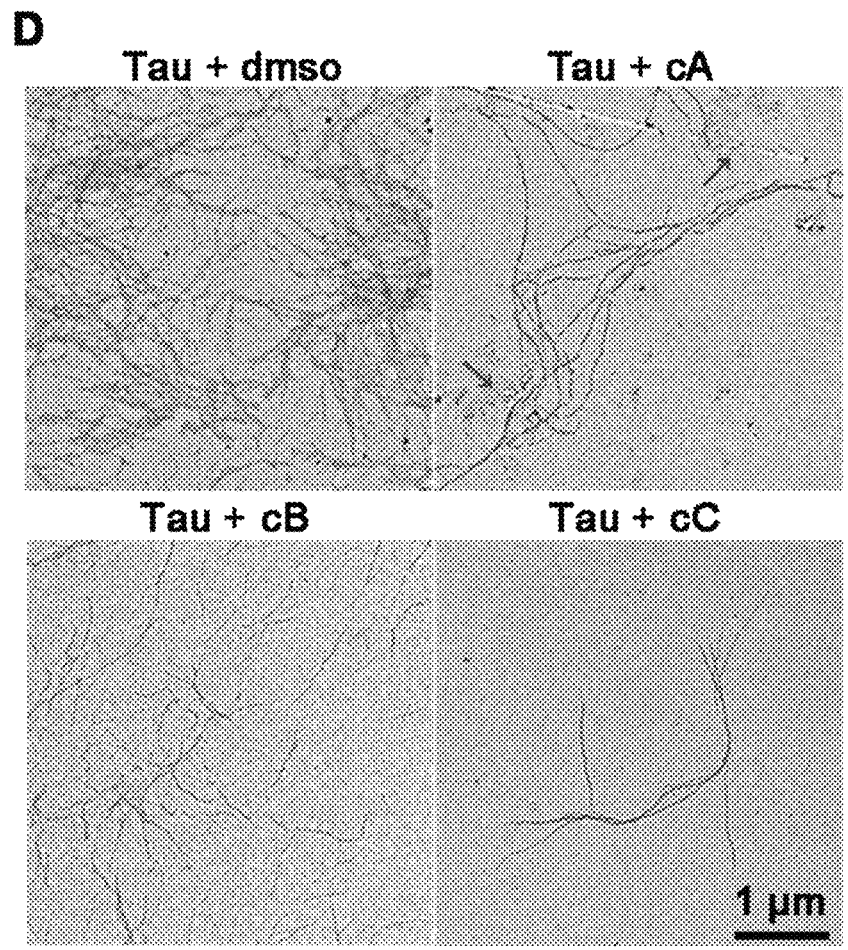
Figure 11H:
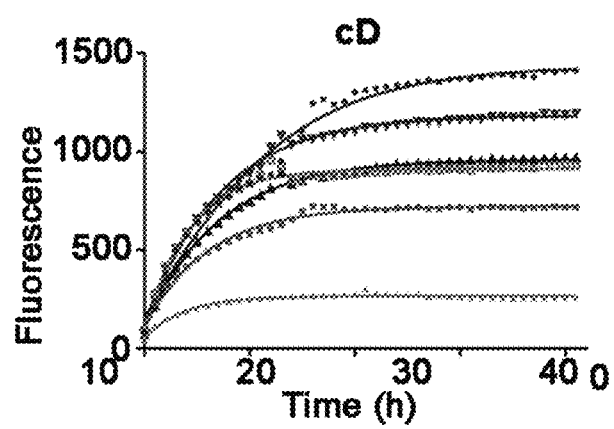
Figure 11I:
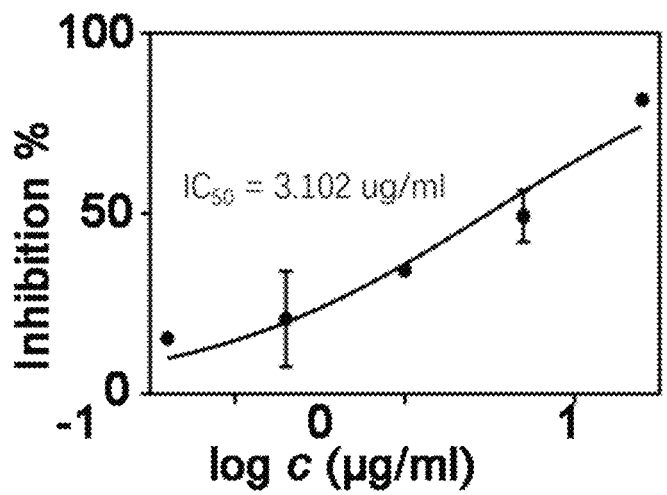
Figure 11J:
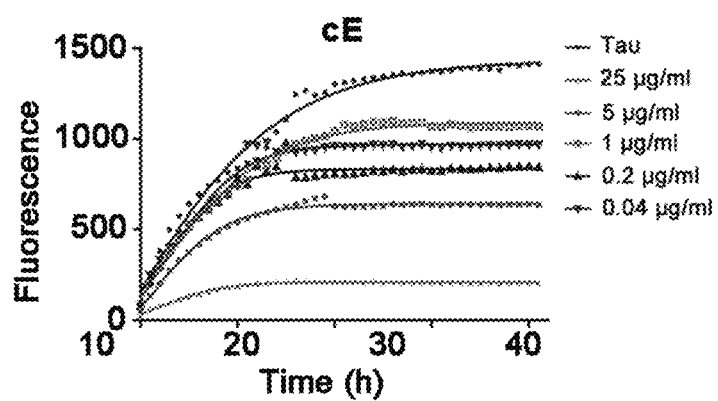
Figure 11K:
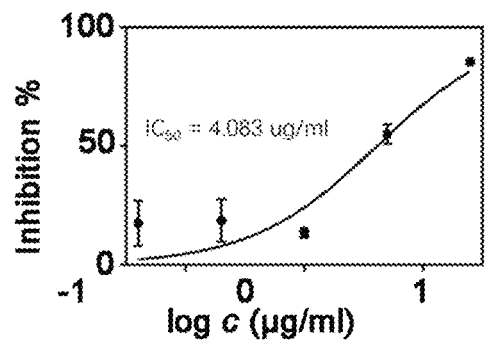
Figure 11L:
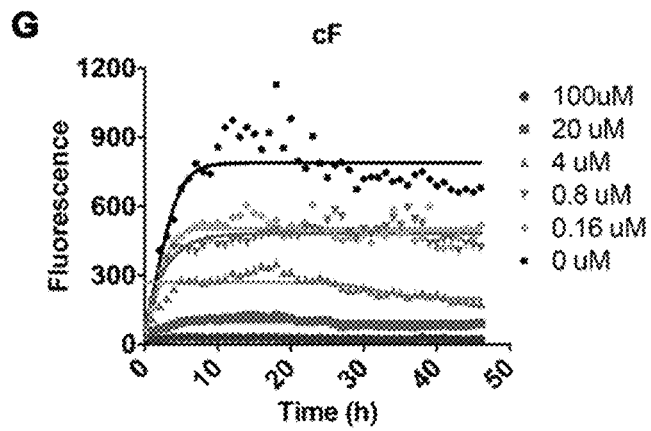
Figure 11M:
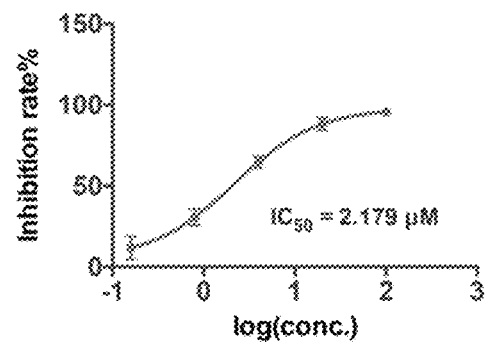

FIG. 11A-11M Compounds cA, cB, cC, cD, cE and cF all inhibit tau-R3 aggregation in vitro. Fluorescence change curves of tau-R3 aggregation with compounds cA (FIG. 11A), cB (FIG. 11C) and cC (FIG. 11E) at indicated concentrations. Inhibition rate curves of cA (FIG. 11B), cB (FIG. 11D) and cC (FIG. 11F) with $IC_{50}$ of 4.25, 13.27 and 20.44 µM, respectively. n=3 independent preparations; $IC_{50}$ were calculated by non-linear regression (variable slop). FIG. 11G. Representative TEM images of tau-R3 (top left), tau-R3 with cA (top right), tau-R3 with cB (bottom left) and tau-R3 with cC (bottom right). The scale bar was 1 m. All data are mean±s.e.m. Fluorescence change curves of tau-R3 aggregation with compounds cD (FIG. 11H), cE (FIG. 11J) and cF (FIG. 11L) at indicated concentrations. Inhibition rate curves of cD (FIG. 11I), cE (FIG. 11K) and cF (FIG. 11M) with $IC_{50}$ of 3.102 µg/ml, 4.083 µg/ml and 2.179 µM, respectively. n=3 independent preparations; $IC_{50}$ were calculated by non-linear regression (variable slop).

Figure 12:
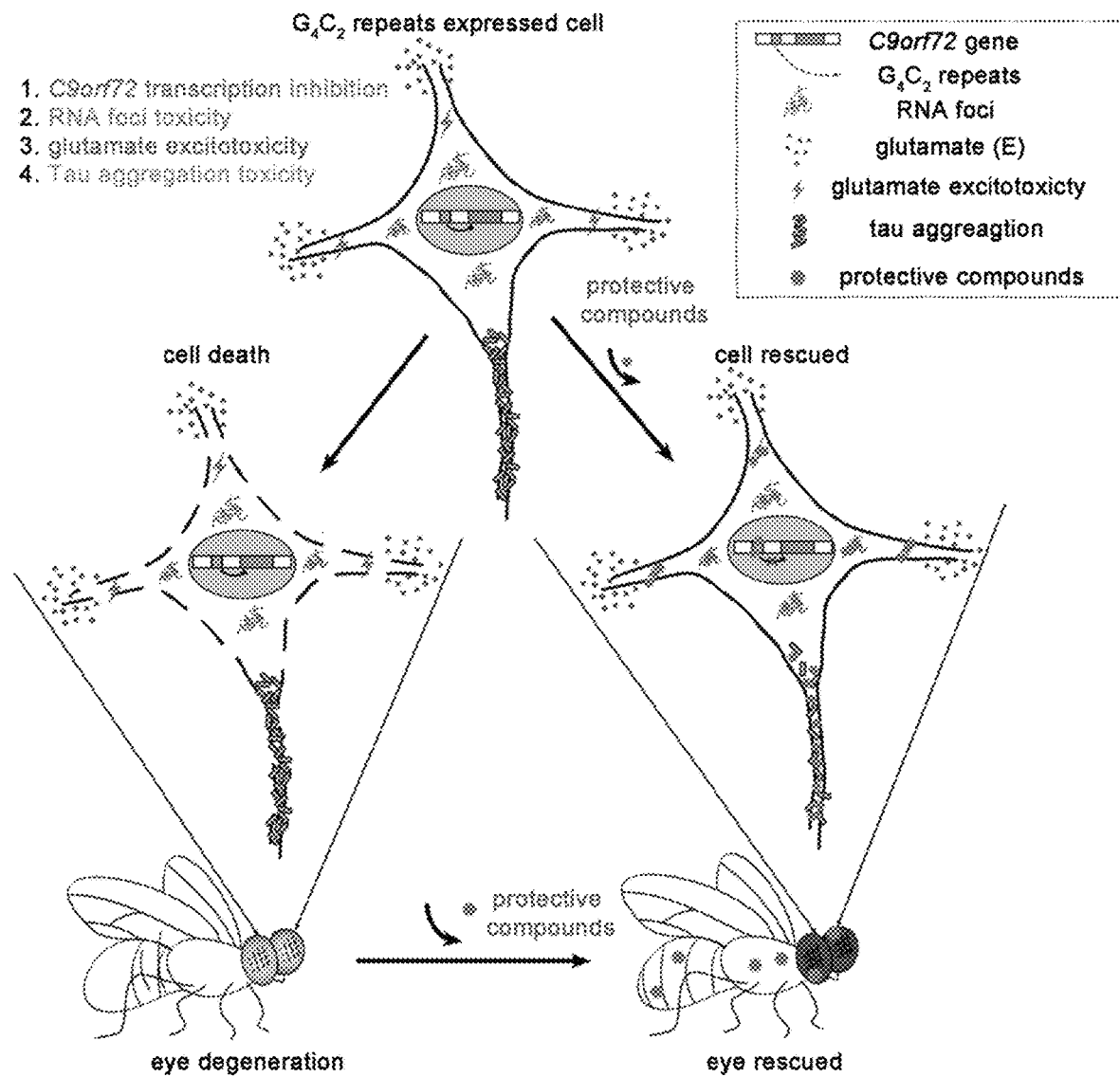

FIG. 12 Graphic summary. cA and cC play neuroprotective roles by targeting multiple pathways contributing to C9orf72 ALS/FTD, including 1) G4C2 DNA HRE-mediated toxicity, 2) G4C2 RNA foci-caused toxicity, 3) glutamate-induced excitotoxicity and 4) aberrant tau aggregation-induced toxicity.

Figure 13:
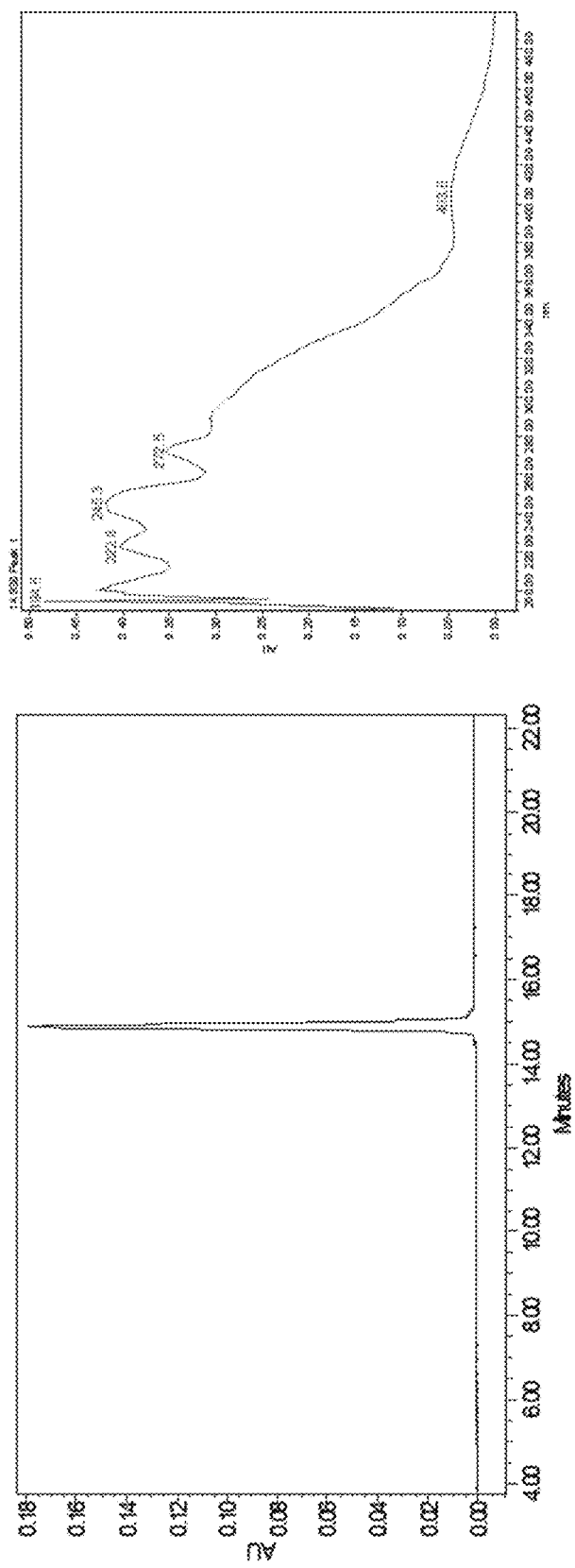

FIG. 13 Isolation of compound chrexanthomycin A (cA) and its UV spectrum.

Figure 14:
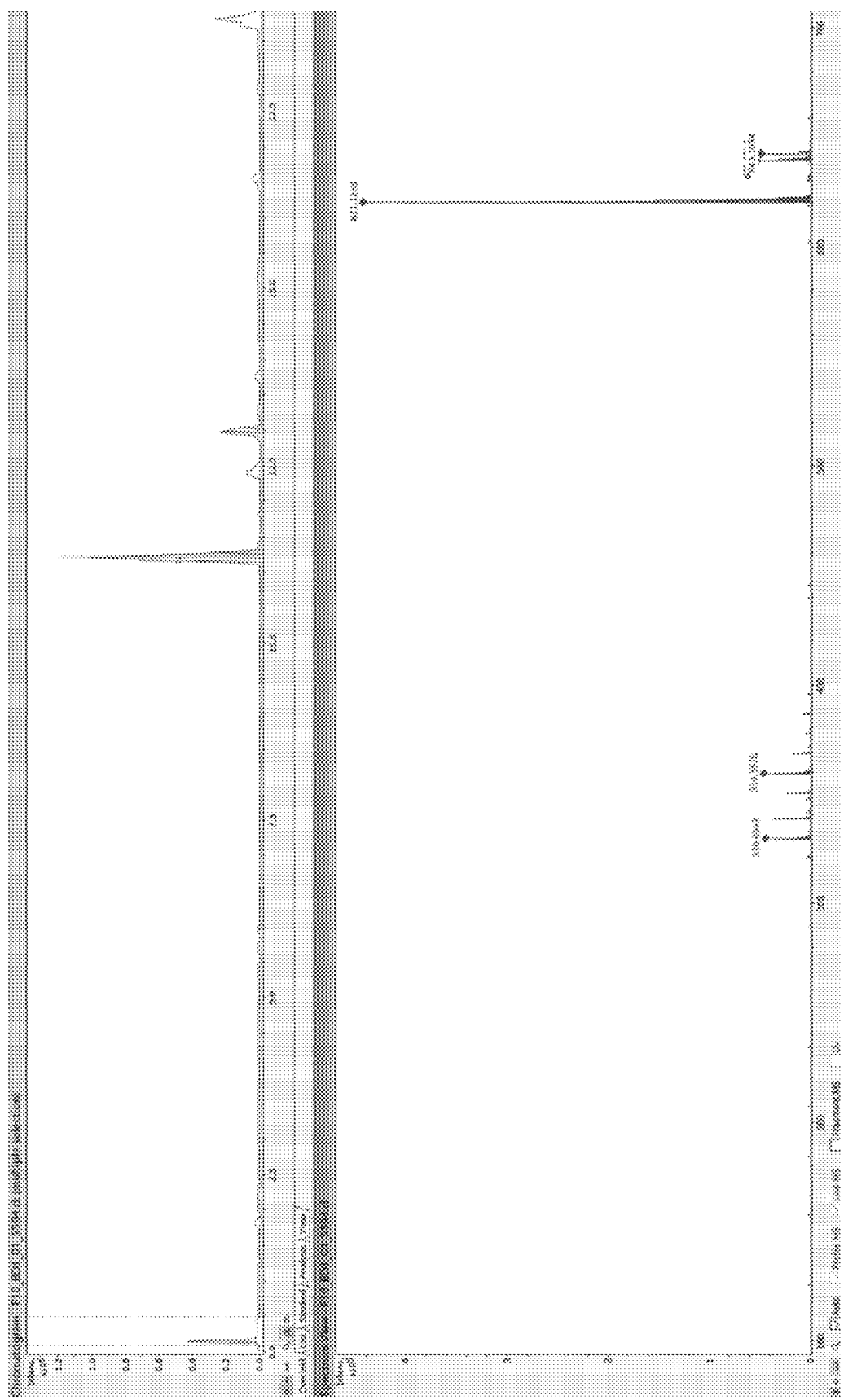

FIG. 14 Positive ion HRMS spectrum of cA (Calcd: 621.1239, found: 621.1235).

Figure 1A:
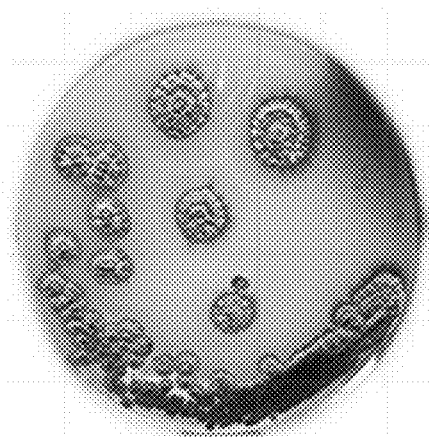
FIGS. 1A-1K Isolation, cytotoxicity test and preliminary neuroprotective test of potential fractions.
Figure 1B:
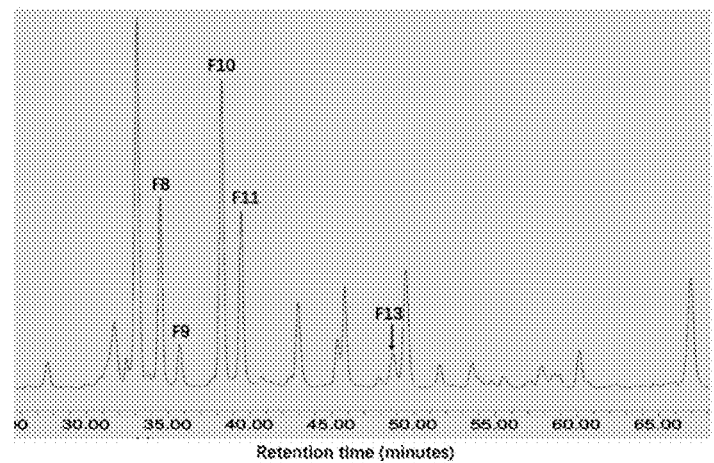
Figure 1C:
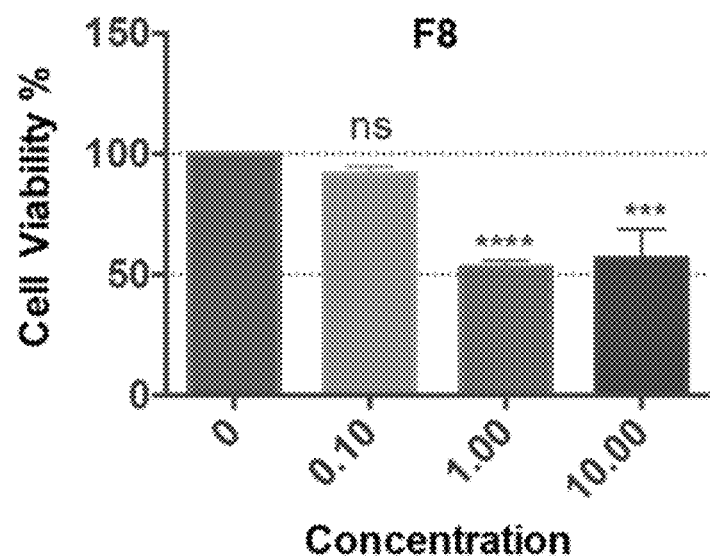
Figure 1D:
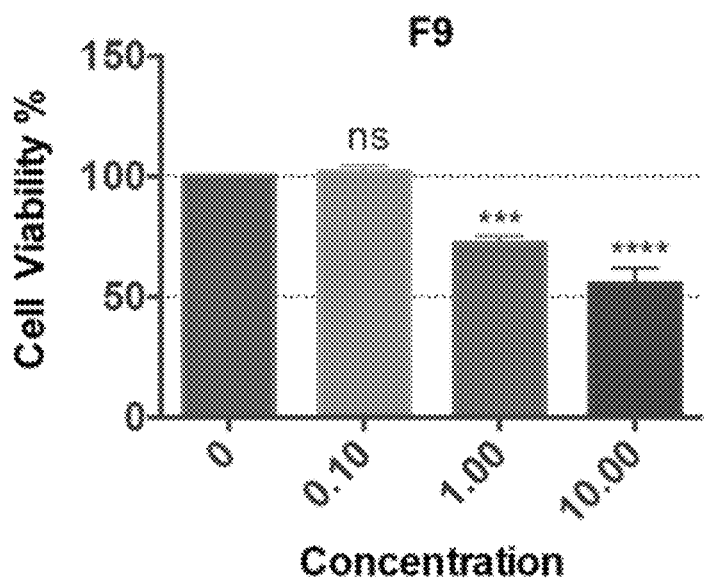
Figure 1E:
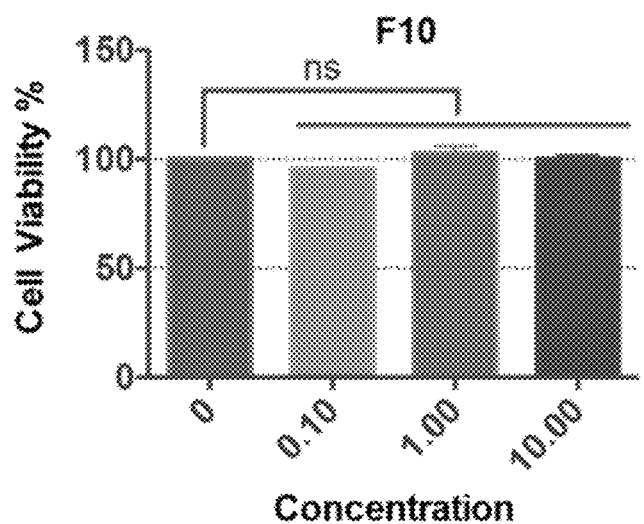
Figure 1F:
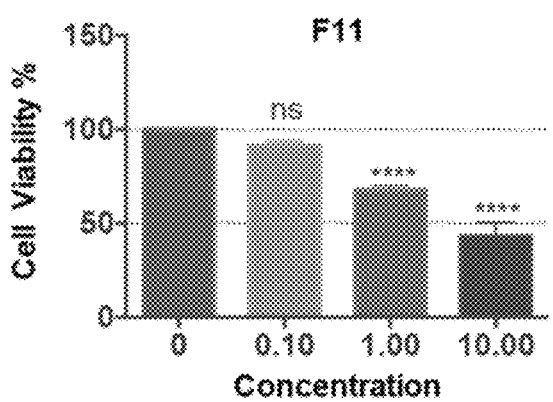
Figure 1G:
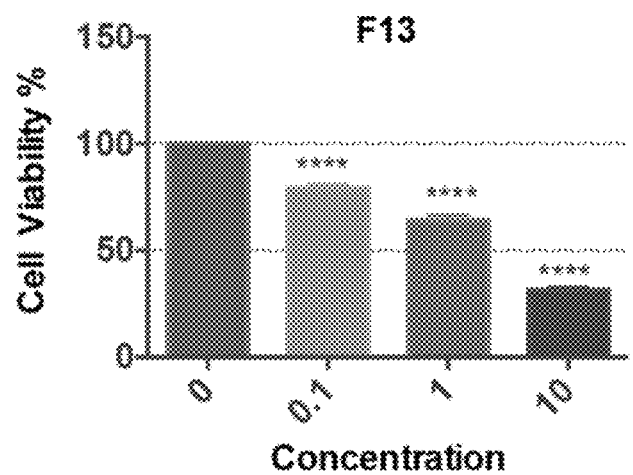
Figure 1H:
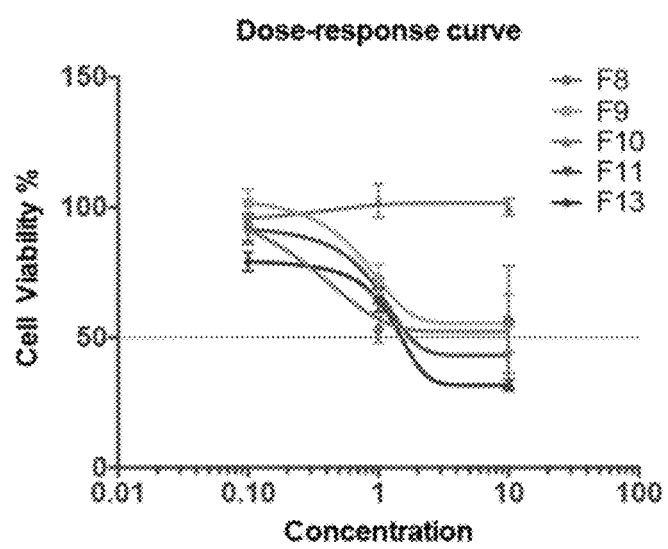
Figure 15:
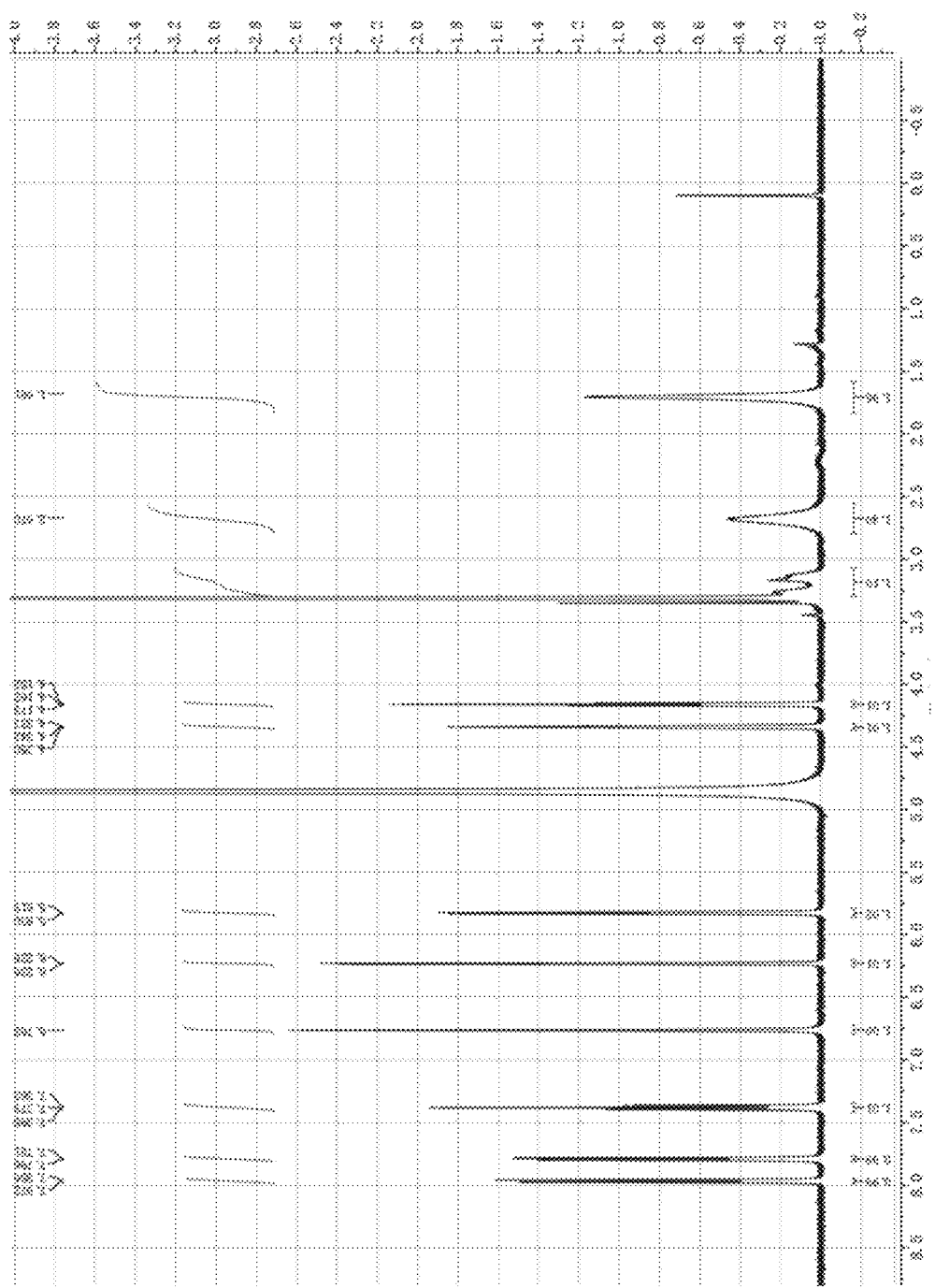

FIG. 15 1H NMR spectrum of cA (800 MHz, CD3OD).

Figure 16:
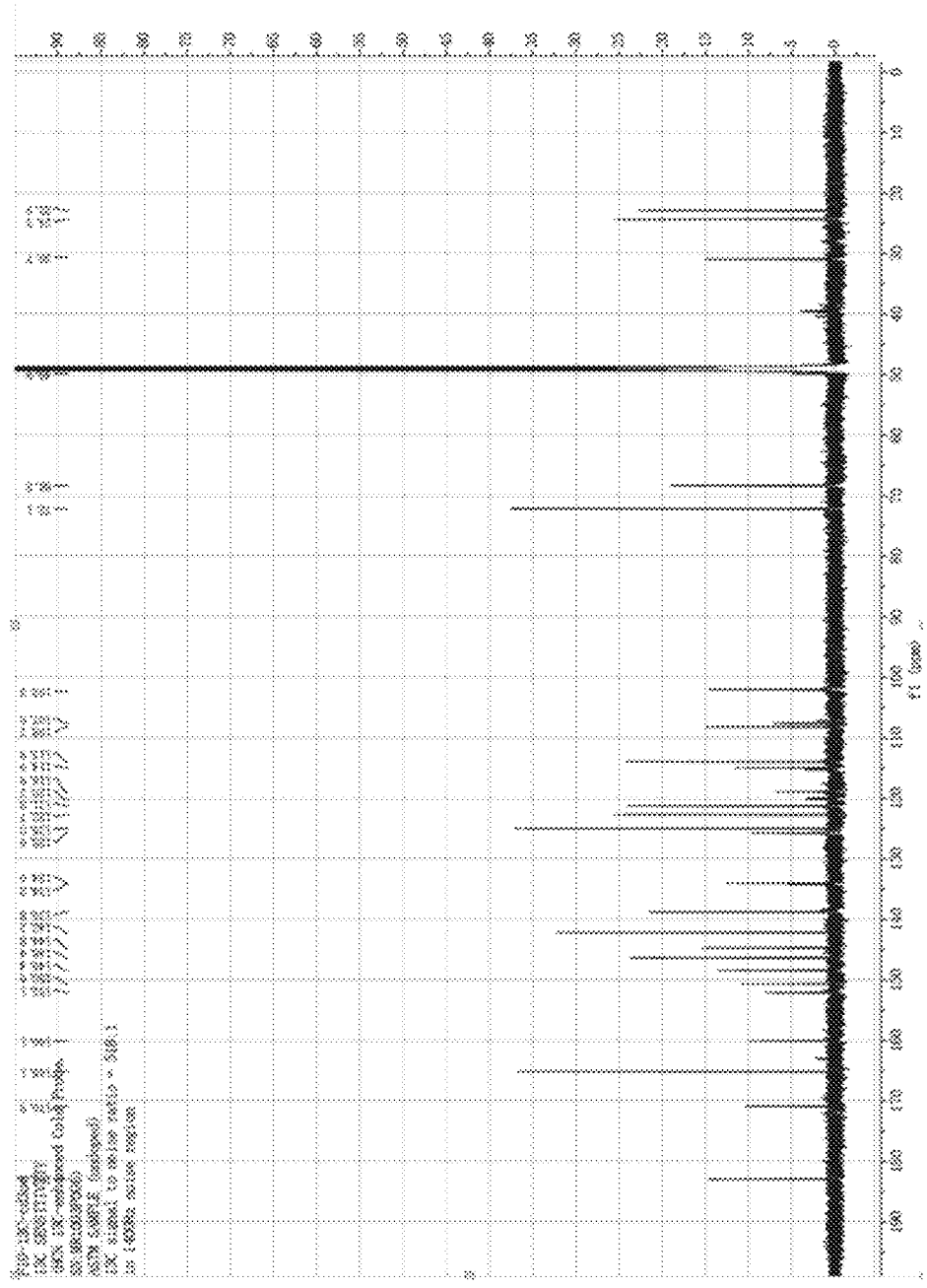

FIG. 16 13C NMR spectrum of cA (200 MHz, CD3OD).

Figure 17:
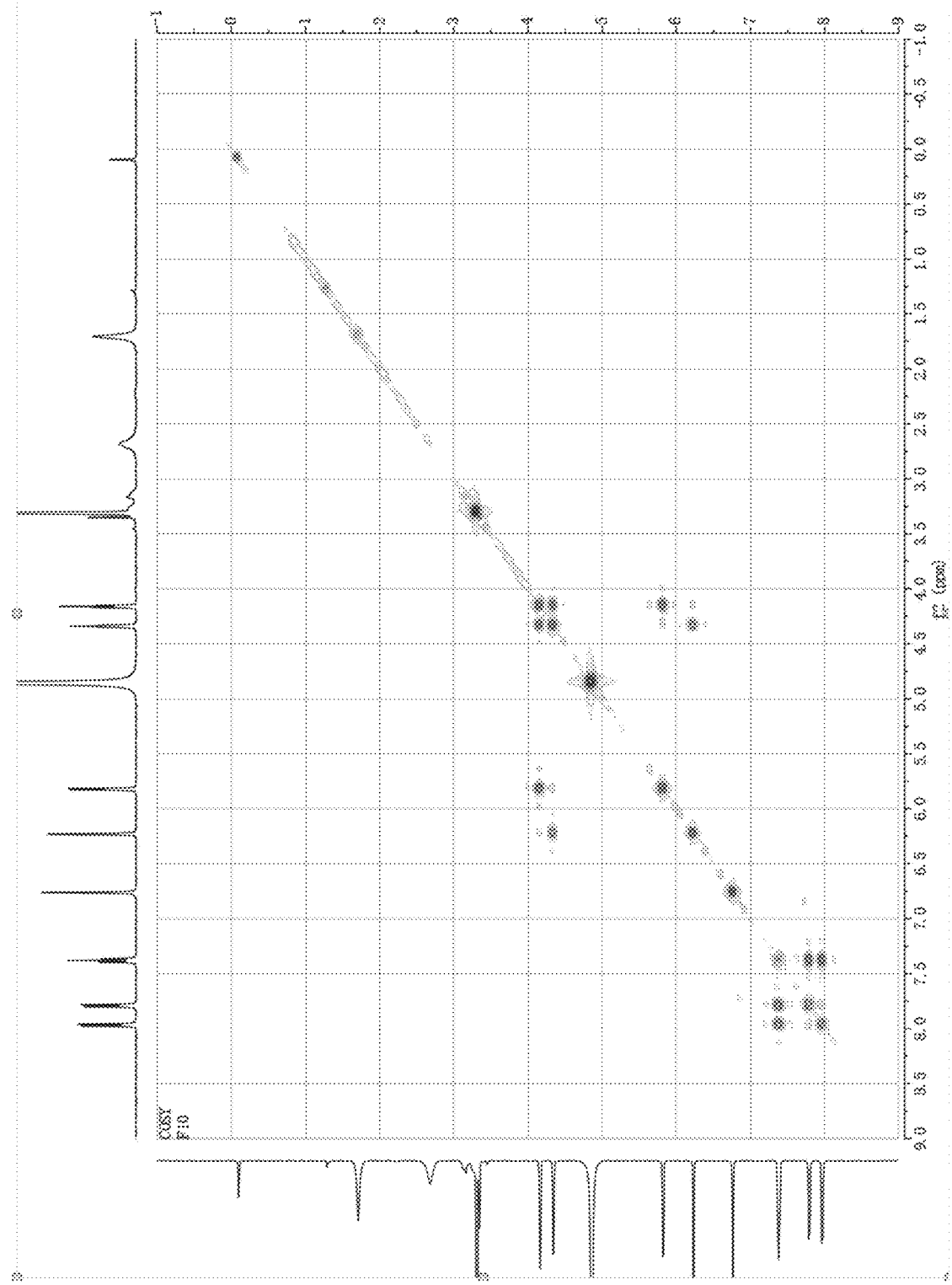

FIG. 17 COSY spectrum of cA (800 MHz, CD3OD).

Figure 18:
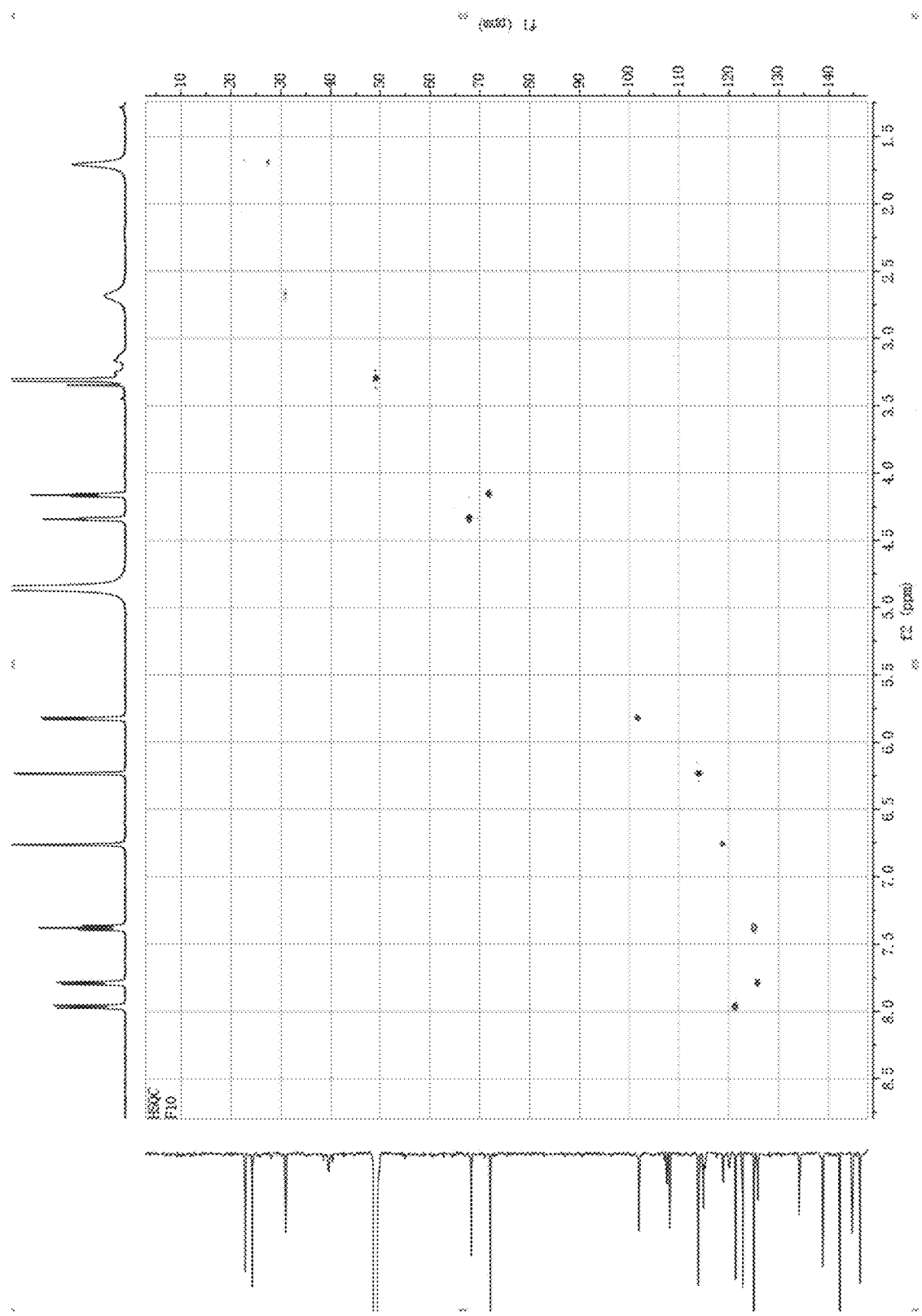

FIG. 18 HSQC spectrum of cA (800 MHz, CD3OD).

Figure 19:
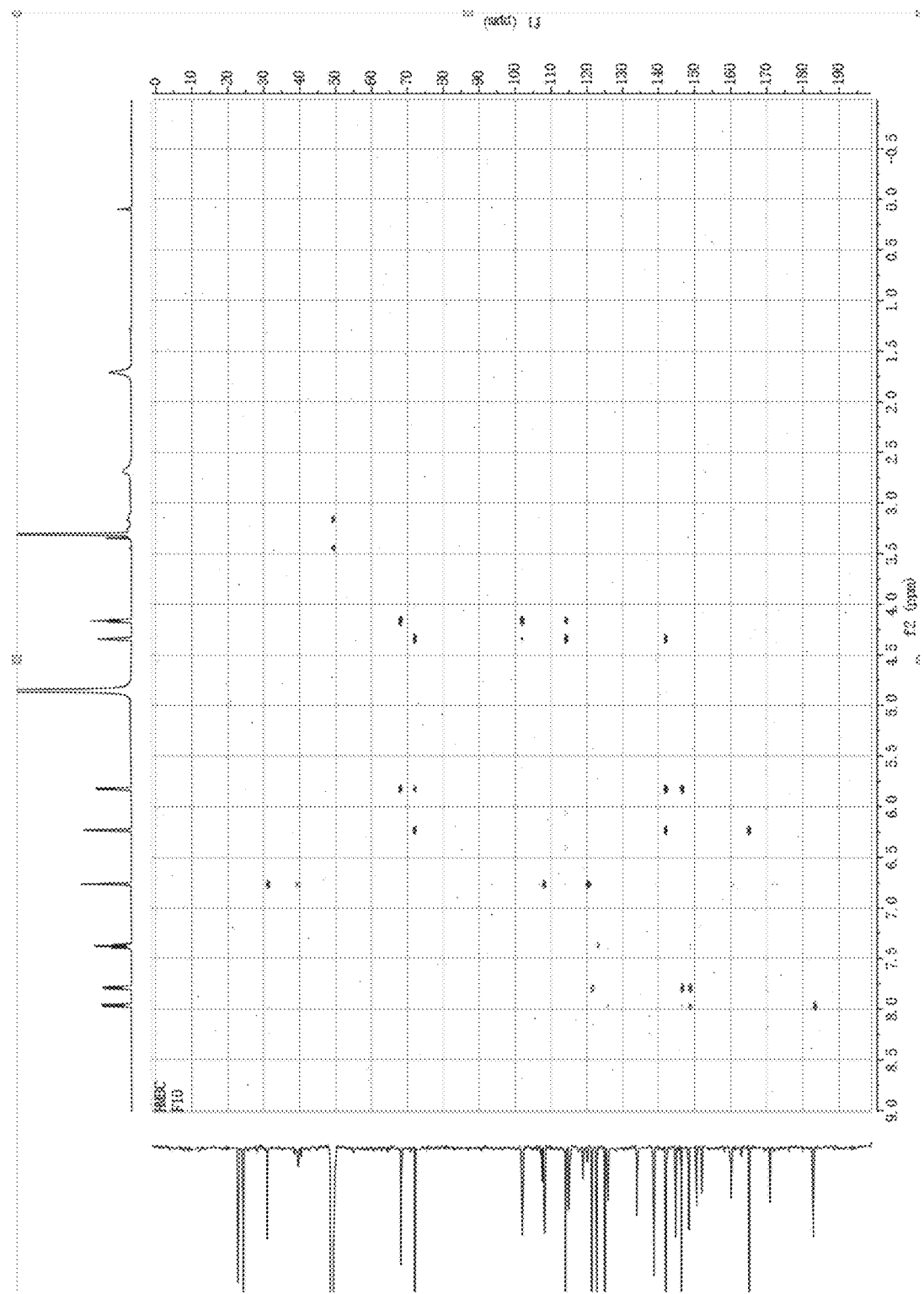

FIG. 19 HMBC spectrum of cA (800 MHz, CD3OD).

Figure 20:
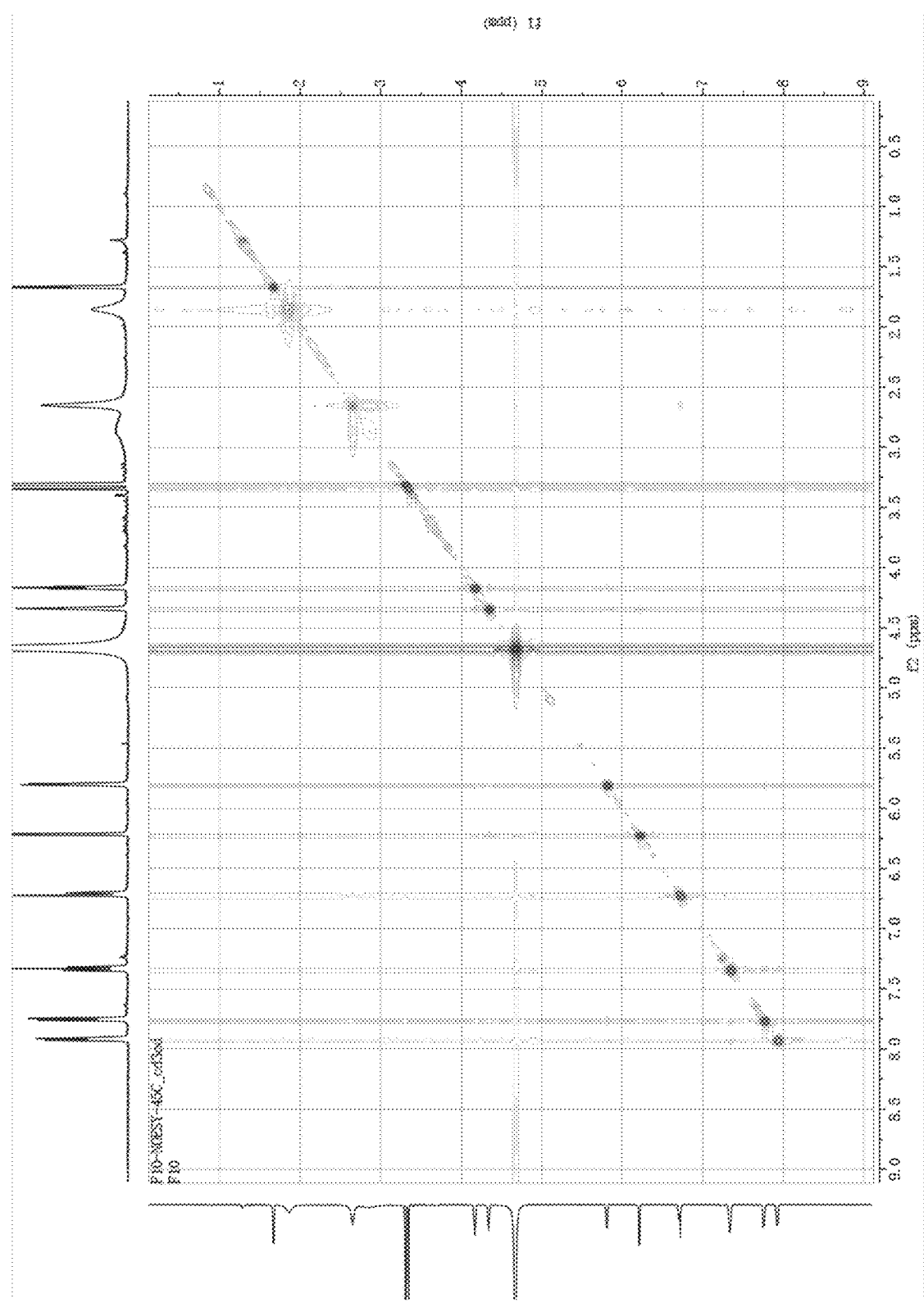

FIG. 20 NOESY spectrum of cA (800 MHz, CD3OD).

Figure 21:
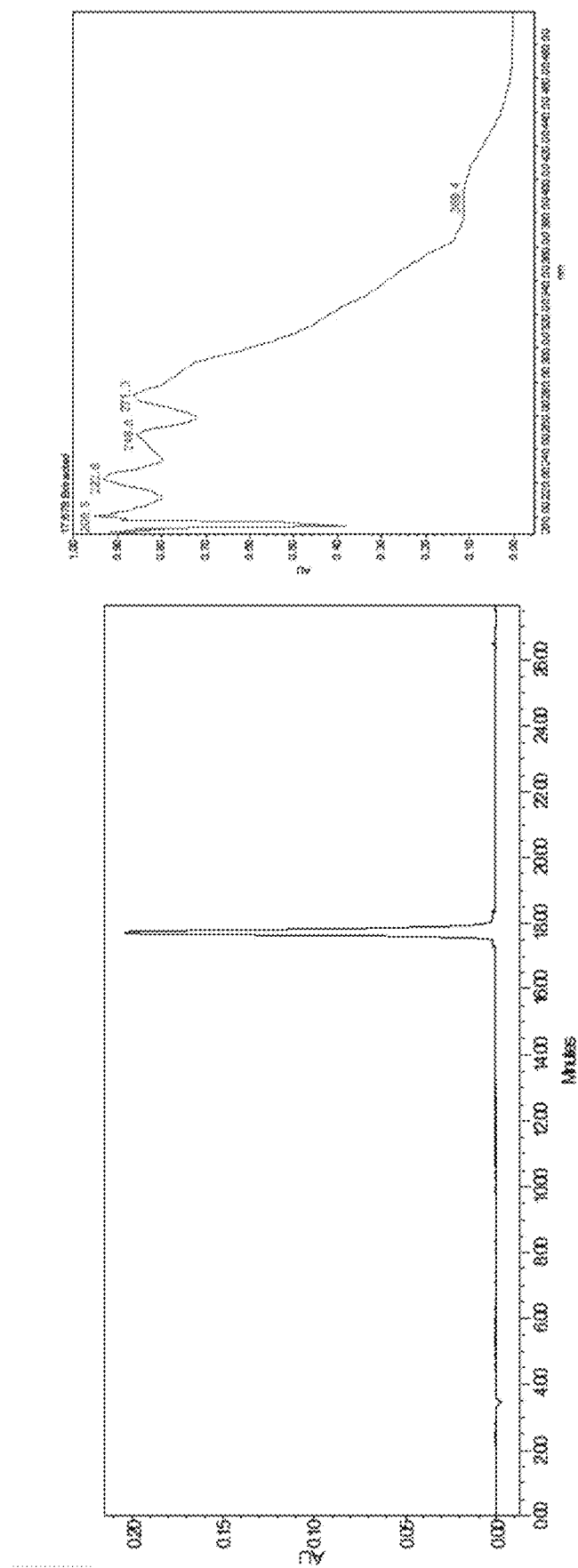

FIG. 21 Isolation of compound chrexanthomycin B (cB) and its UV spectrum.

Figure 22:
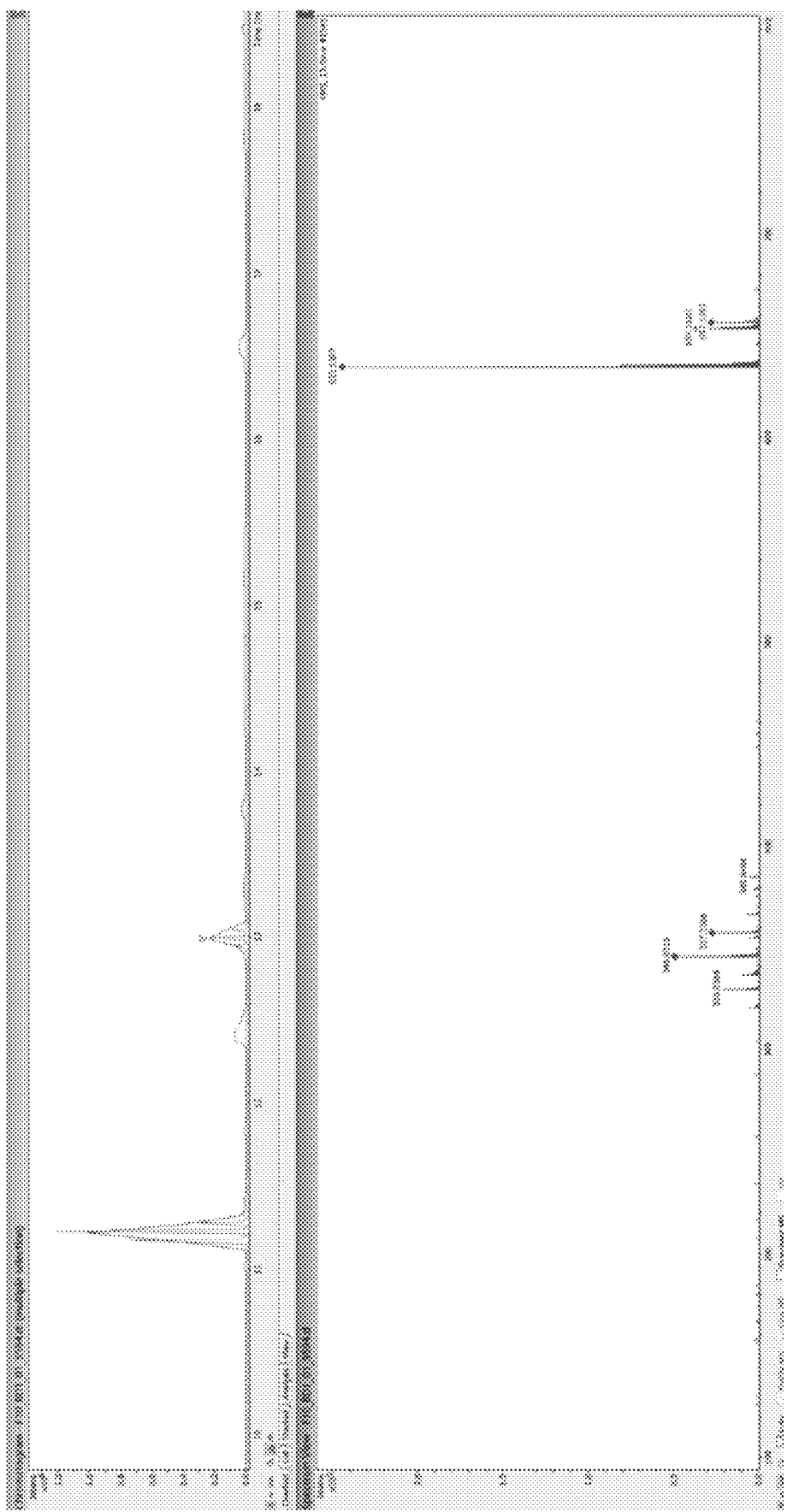

FIG. 22 Positive ion HRMS spectrum of cB (Calcd: 635.1395, found: 635.1387).

Figure 23:
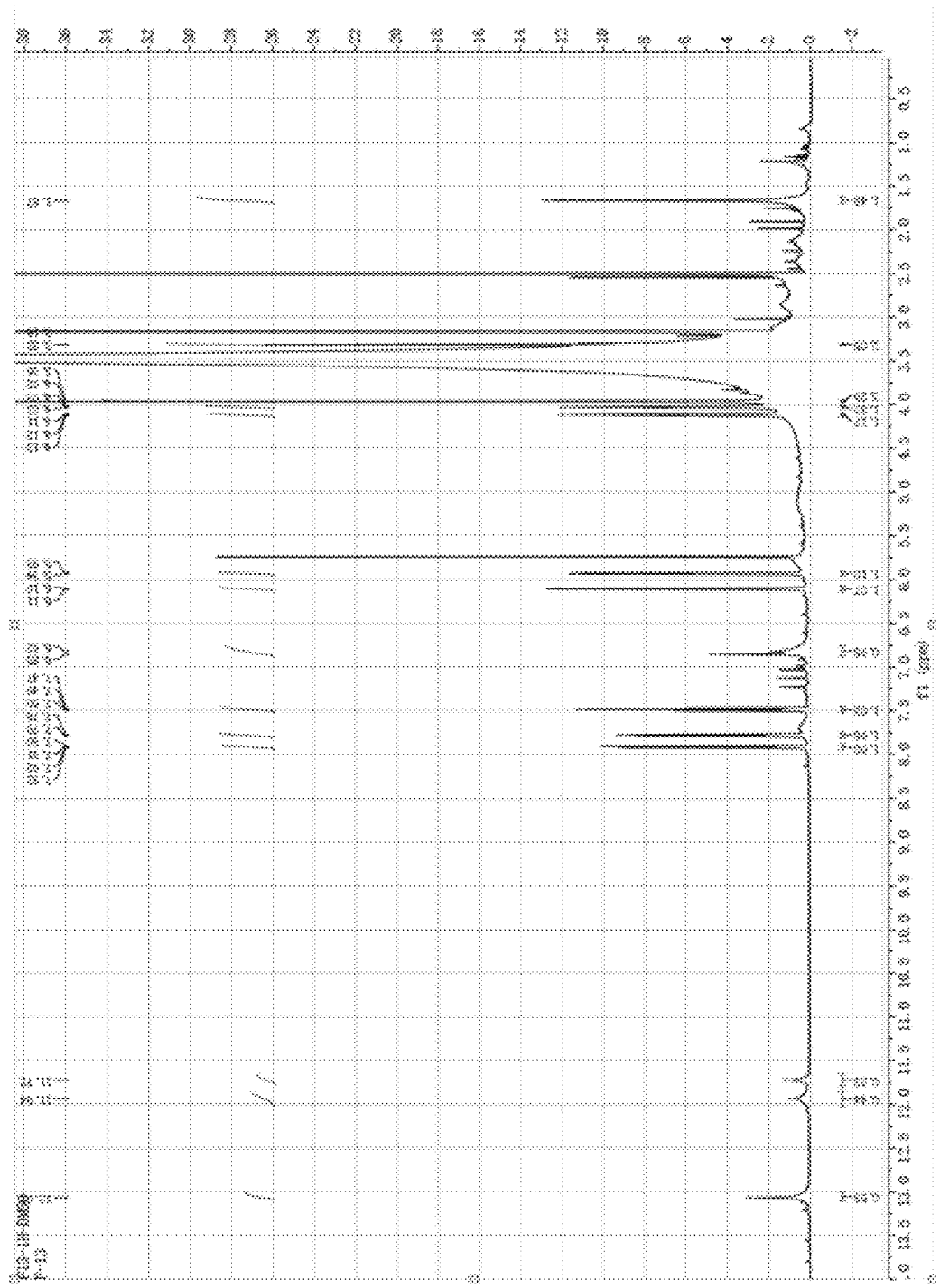

FIG. 23 1H NMR spectrum of cB (800 MHz, DMSO-d6).

Figure 24:
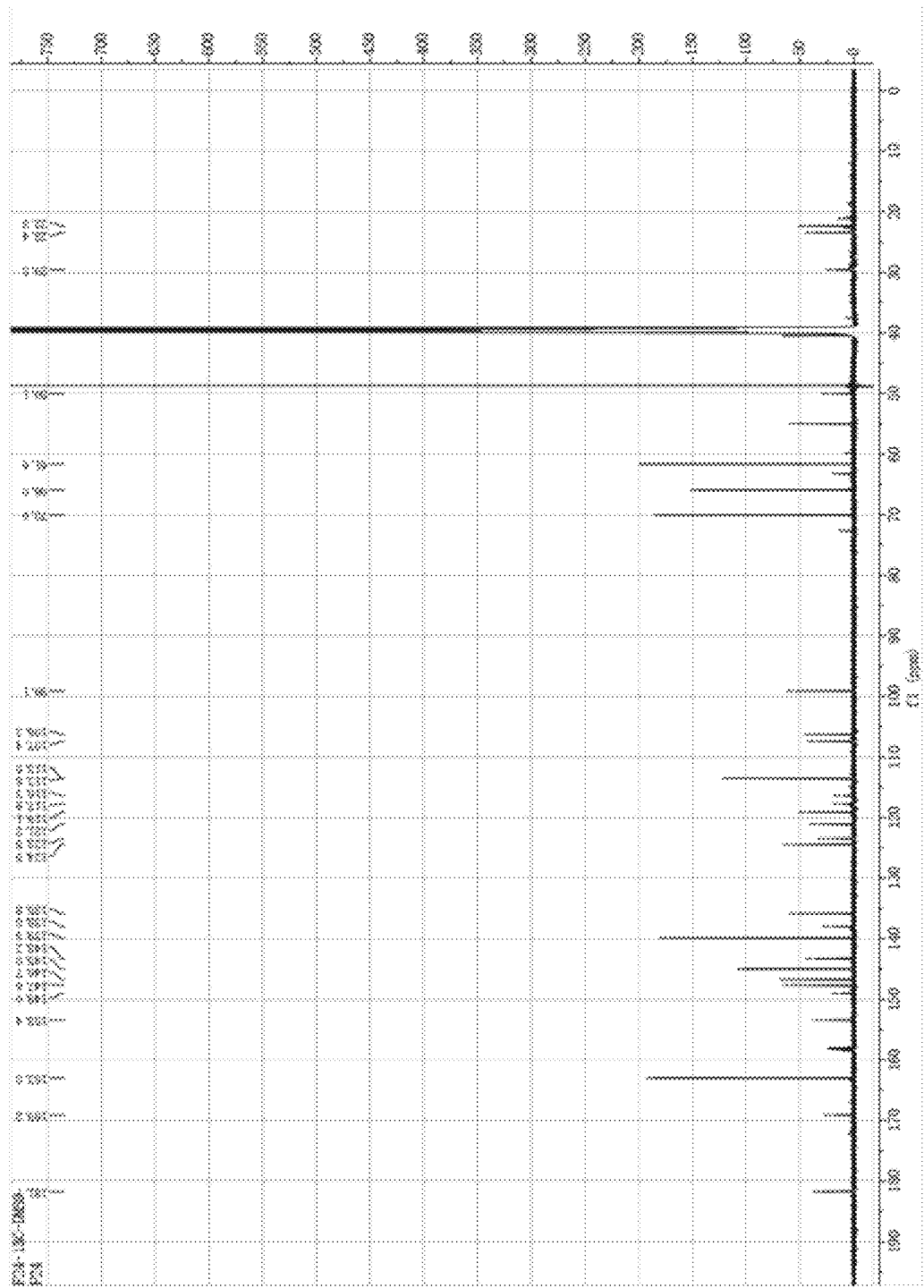

FIG. 24 13C NMR spectrum of cB (200 MHz, DMSO-d6).

Figure 25:
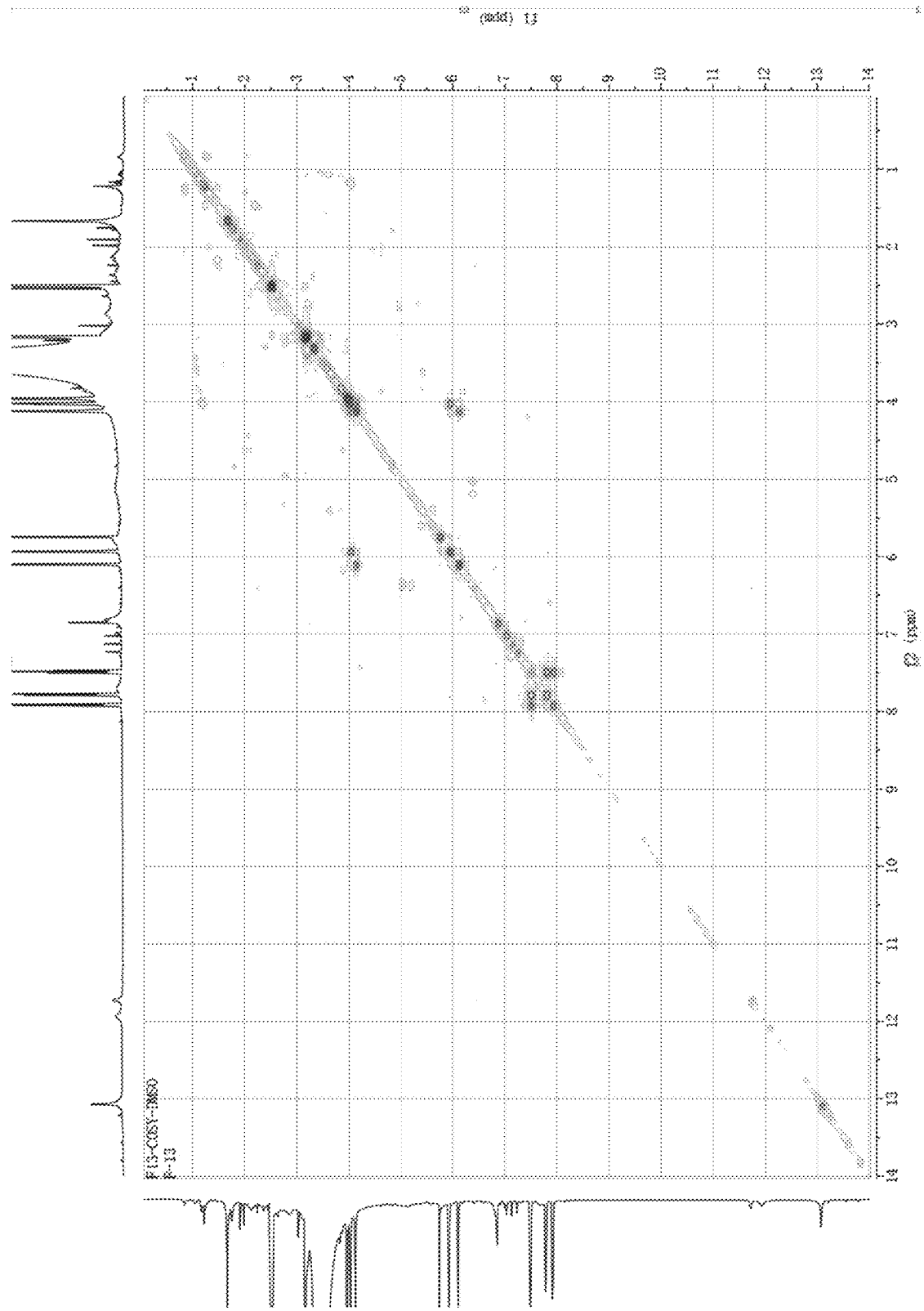

FIG. 25 COSY spectrum of cB (800 MHz, DMSO-d6).

Figure 26:
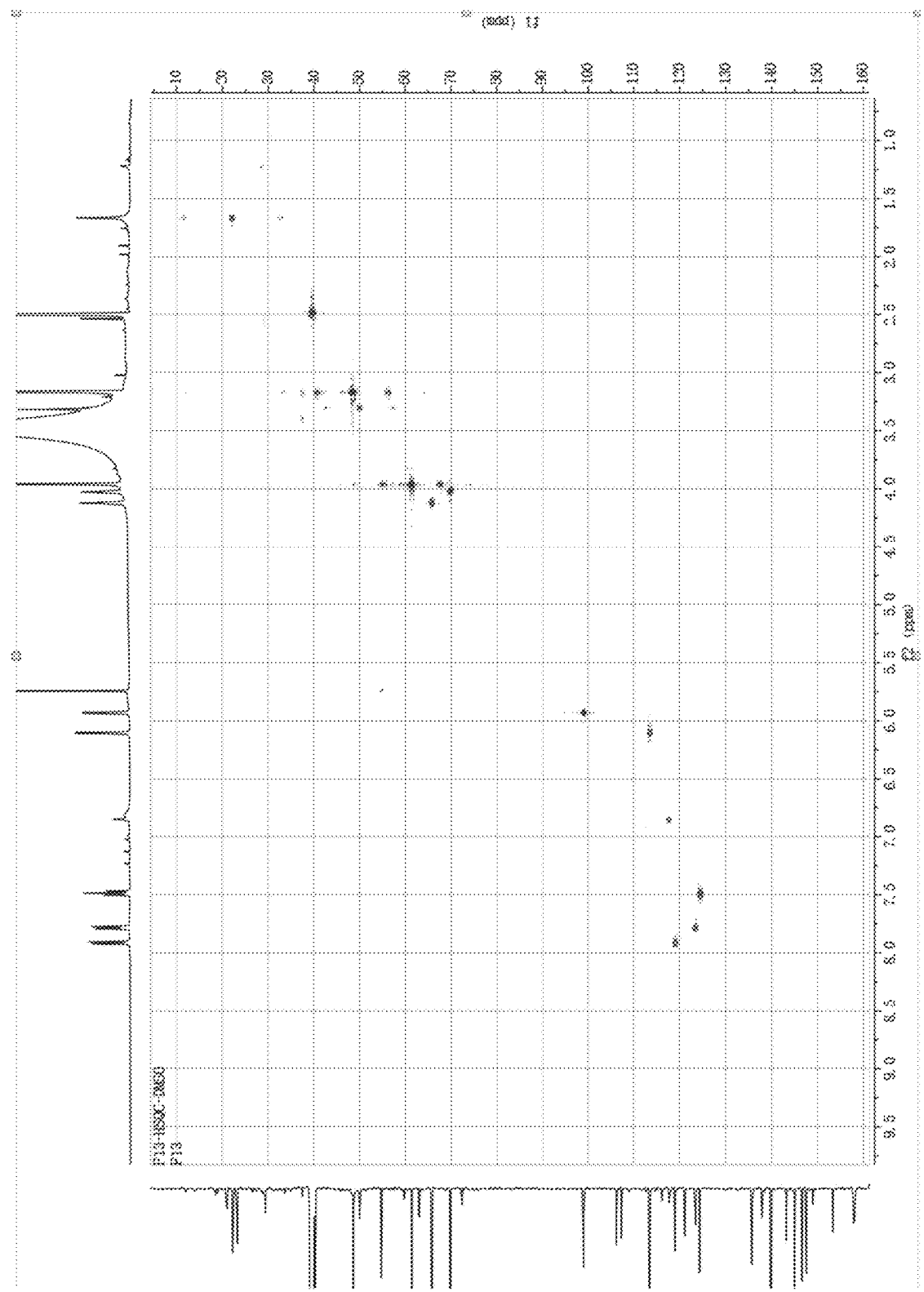

FIG. 26 HSQC spectrum of cB (800 MHz, DMSO-d6).

Figure 27:
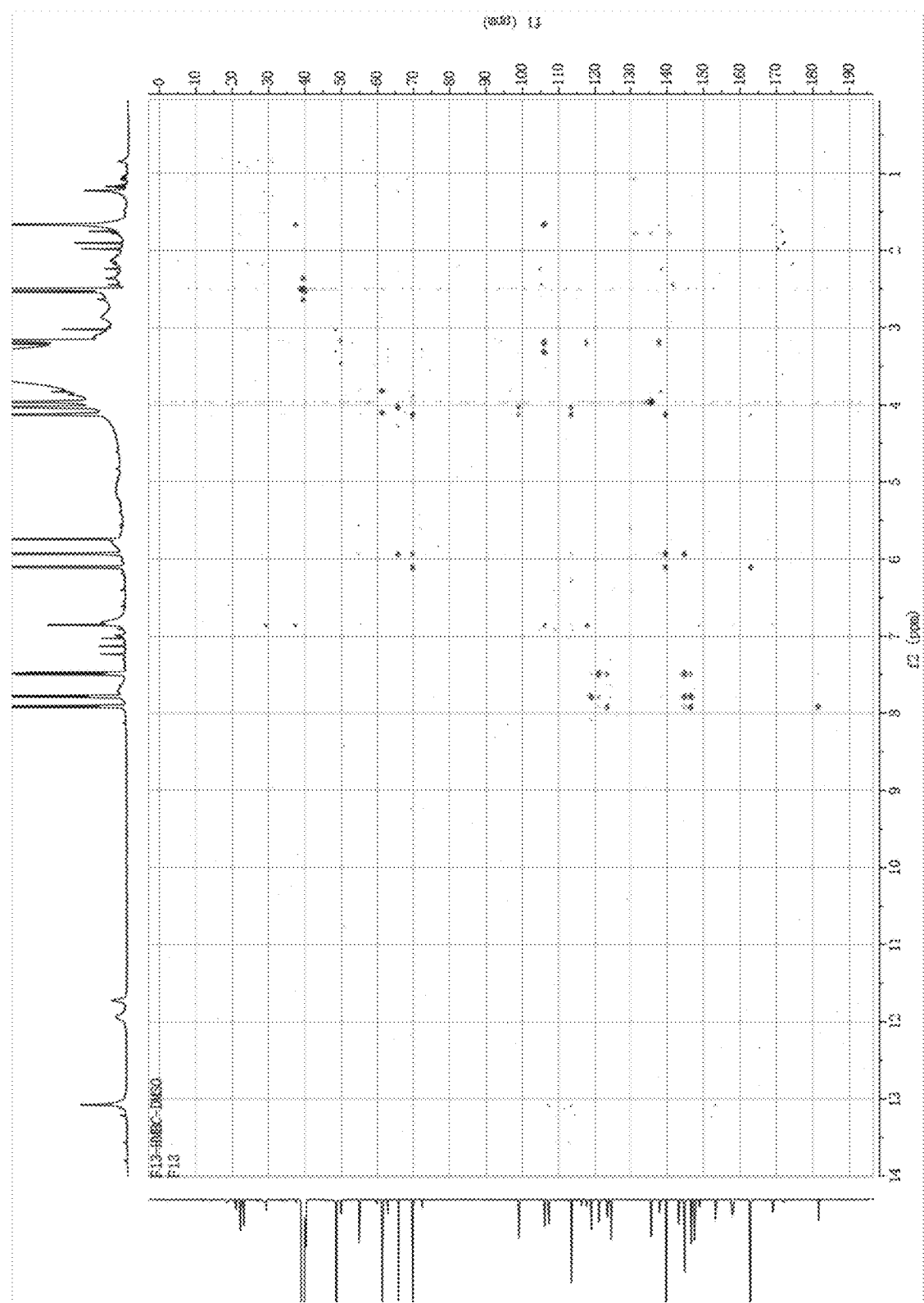

FIG. 27 HMBC spectrum of cB (800 MHz, DMSO-d6).

Figure 28:
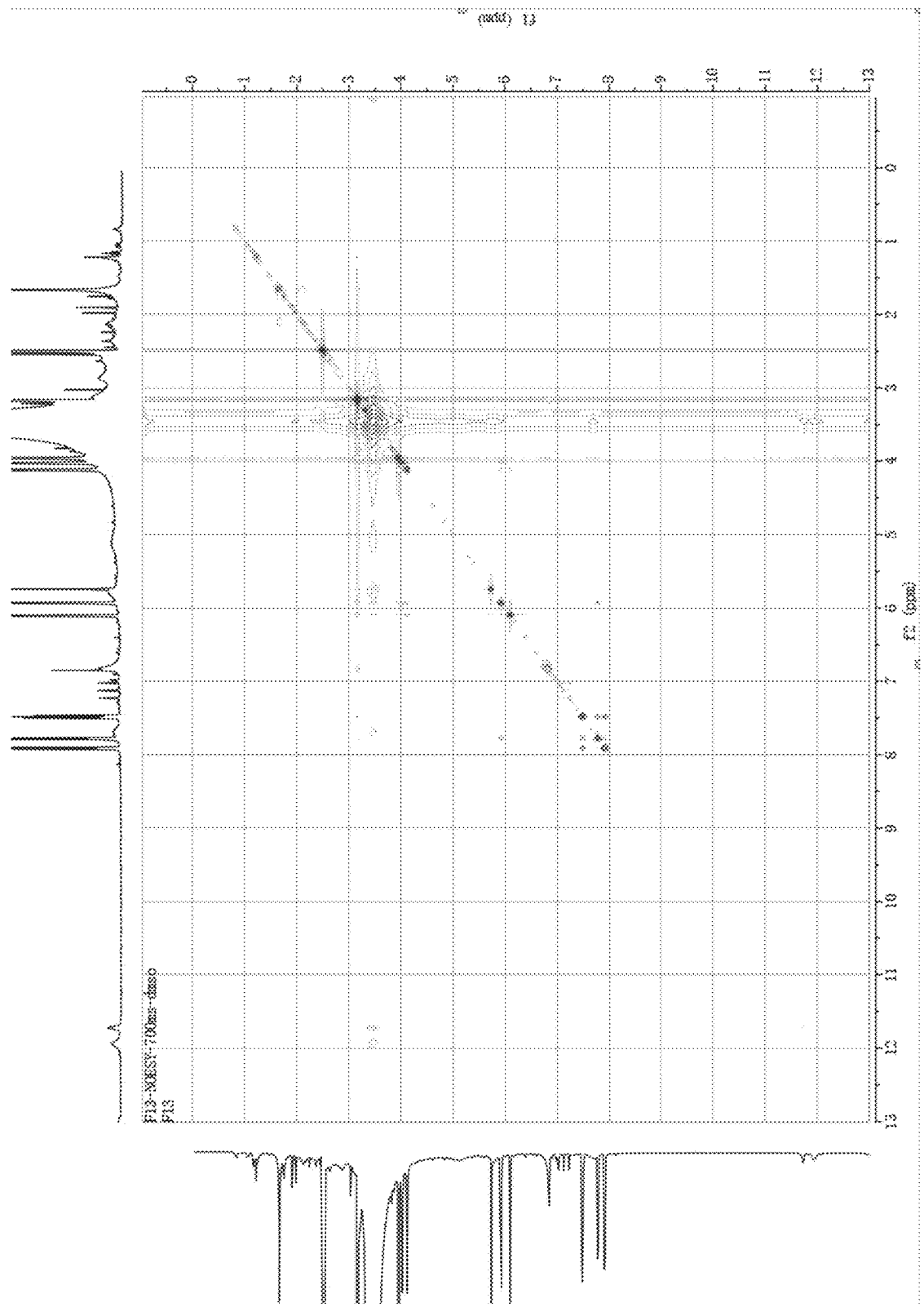

FIG. 28 NOESY spectrum of cB (800 MHz, DMSO-d6).

Figure 29:
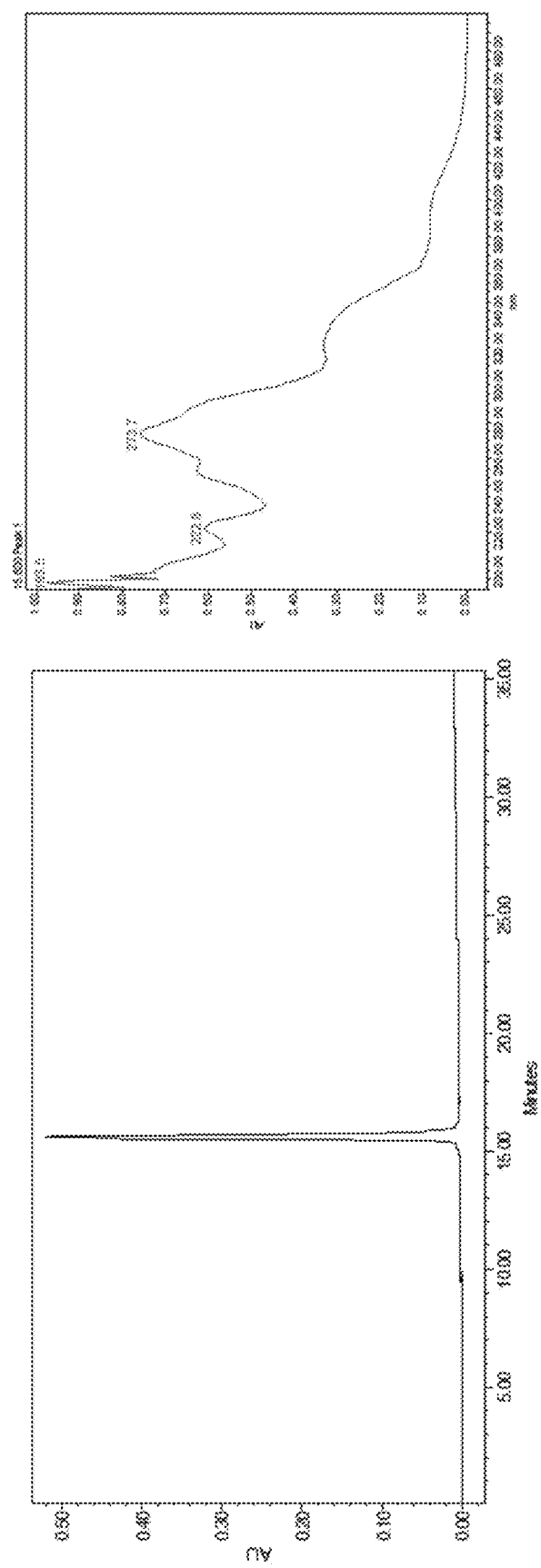

FIG. 29 Isolation of compound chrexanthomycin C (cC) and its UV spectrum.

Figure 30:
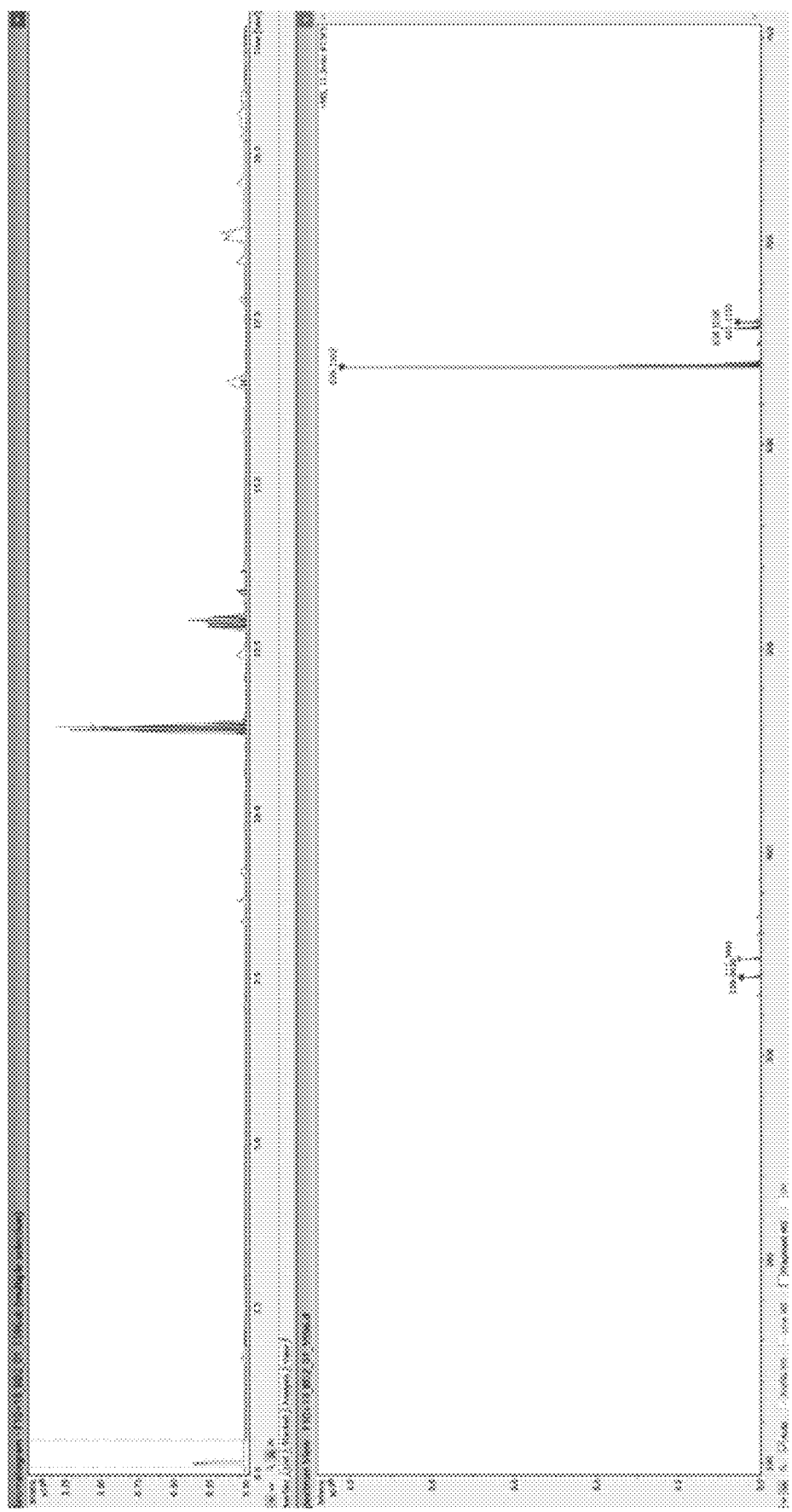

FIG. 30 Positive ion HRMS spectrum of cC (Calcd: 639.1344, found: 639.1332).

Figure 31:
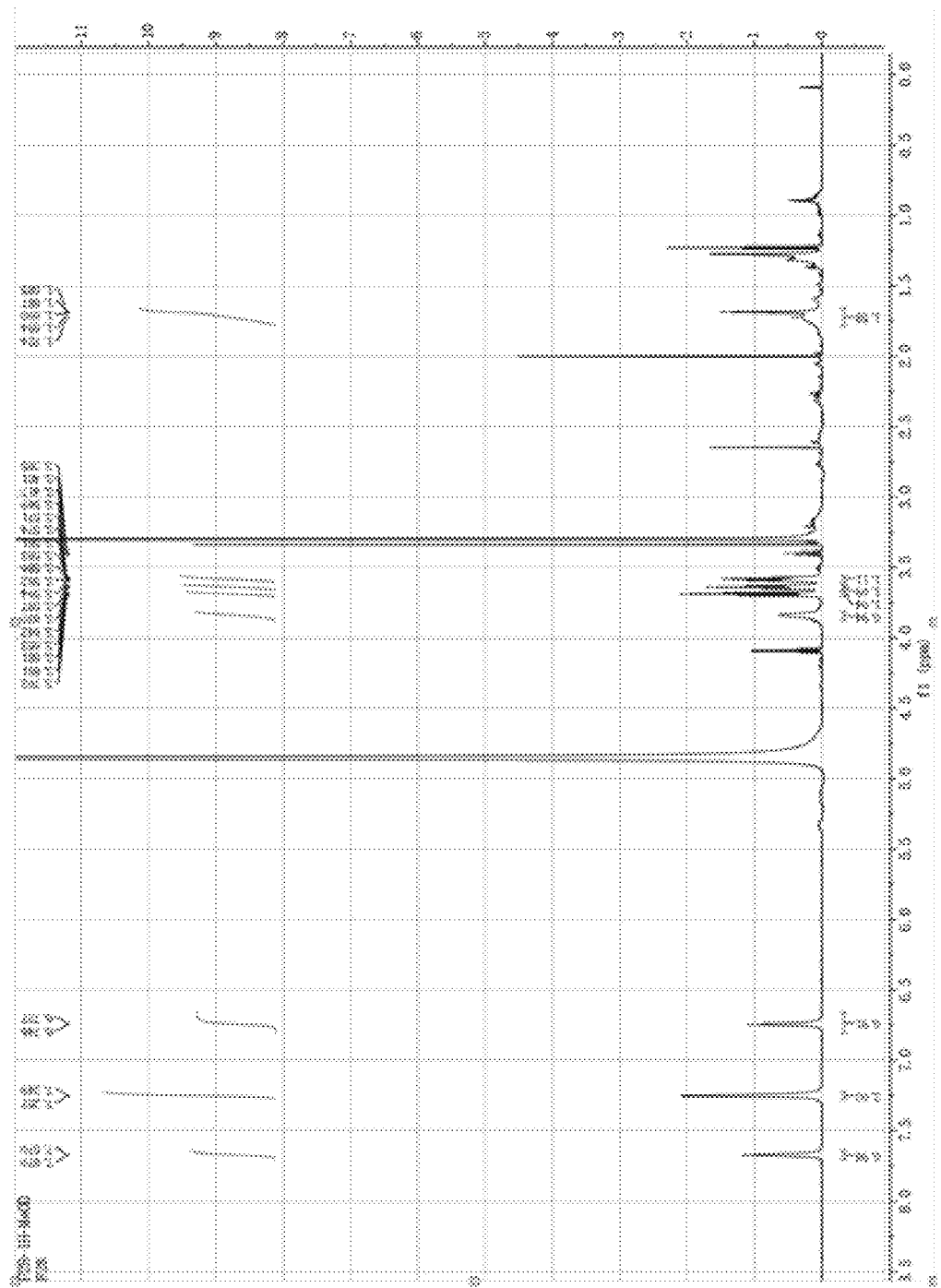

FIG. 31 1H NMR spectrum of cC (800 MHz, CD3OD).

Figure 32:
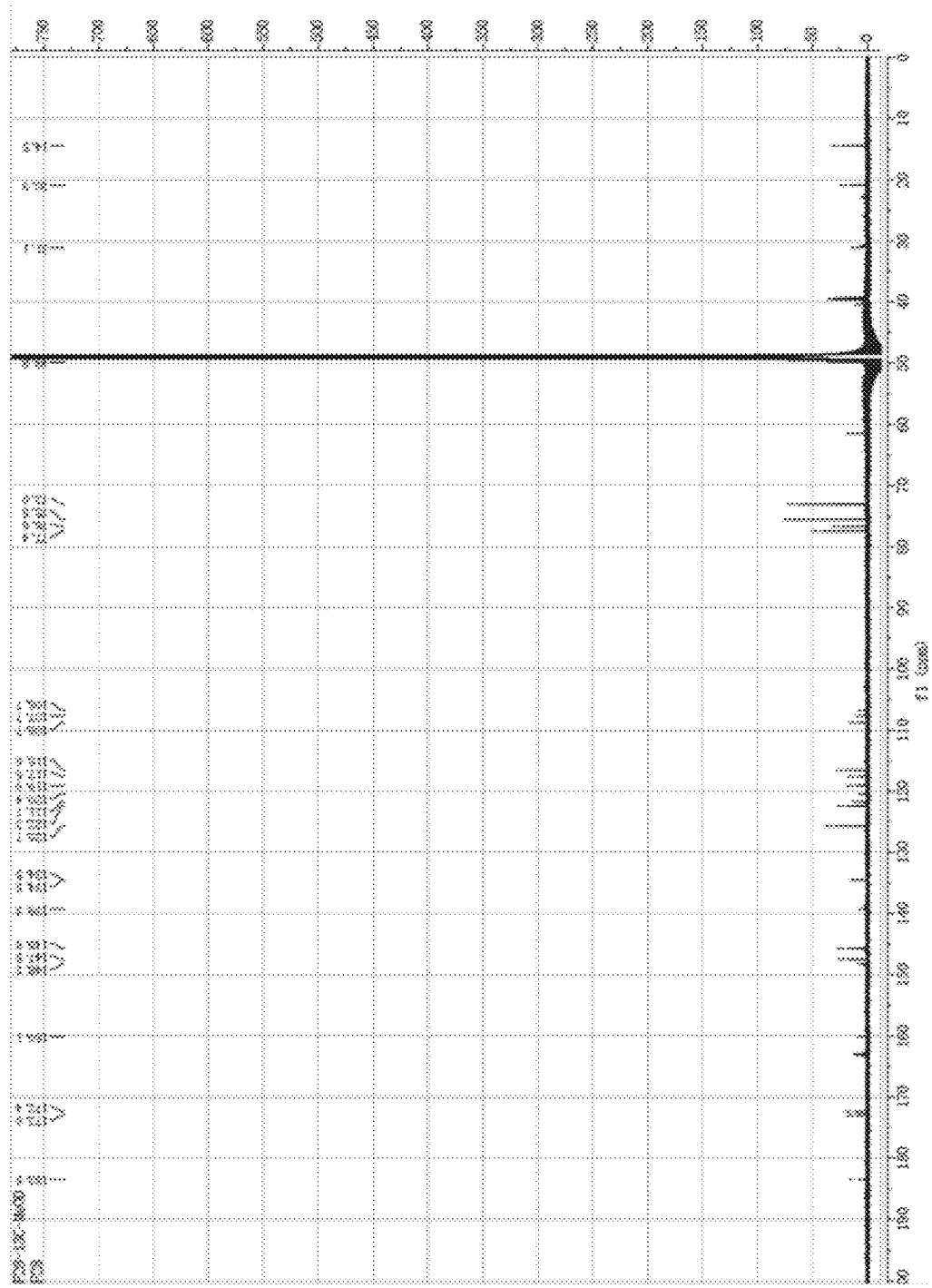

FIG. 32 13C NMR spectrum of cC (200 MHz, CD3OD).

Figure 33:
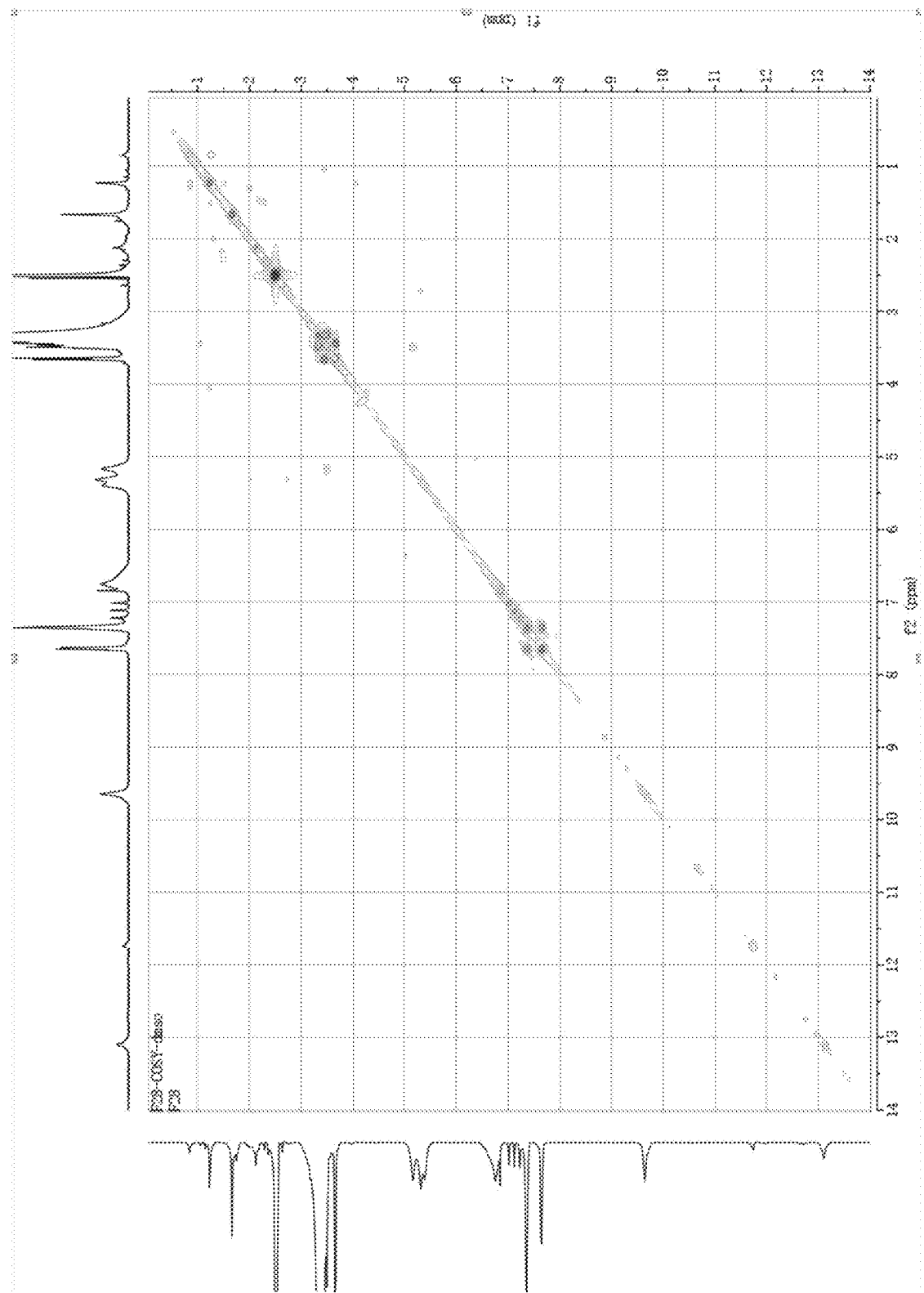

FIG. 33 COSY spectrum of cC (800 MHz, DMSO-d6).

Figure 34:
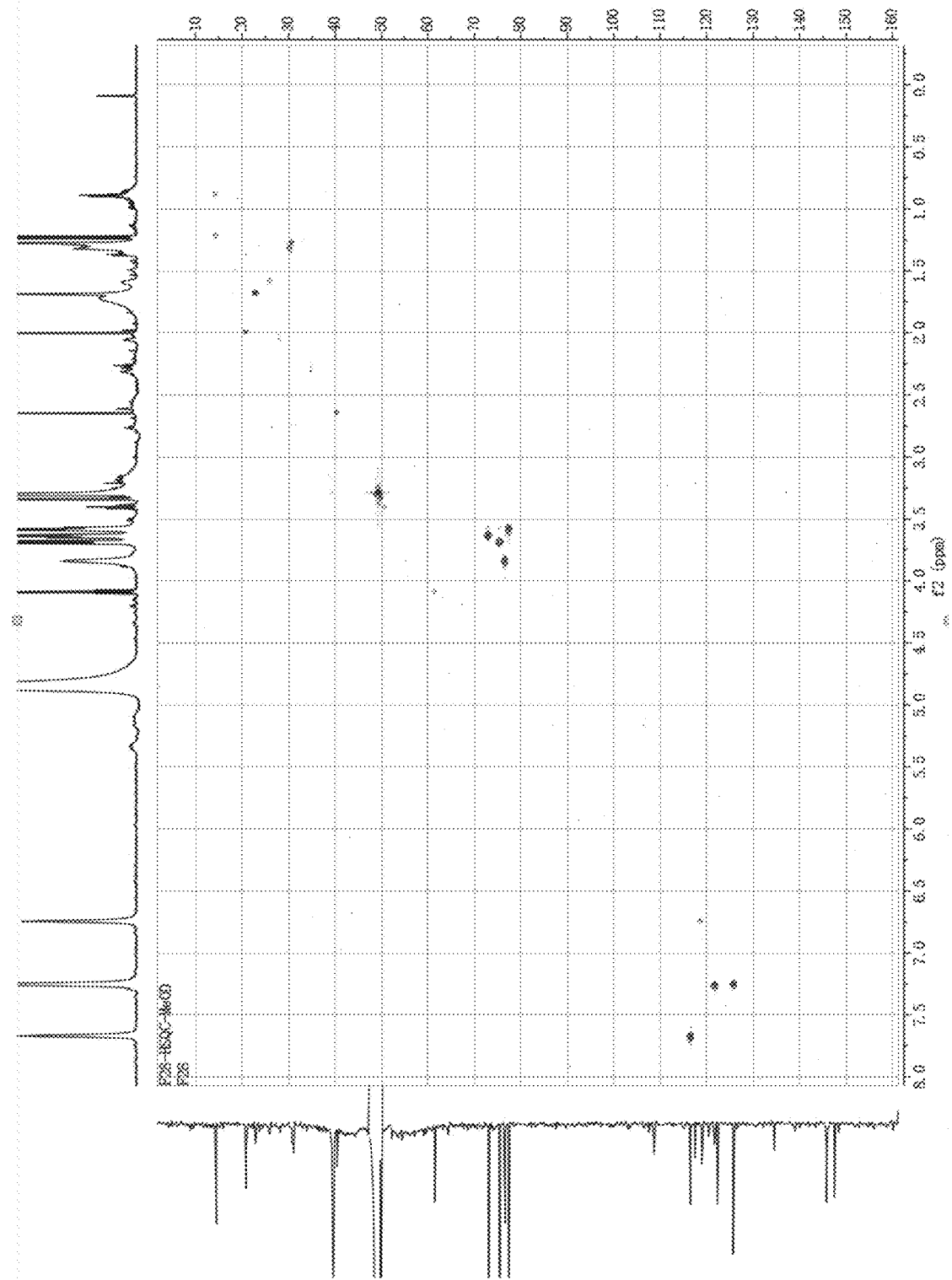

FIG. 34 HSQC spectrum of cC (800 MHz, CD3OD).

Figure 35:
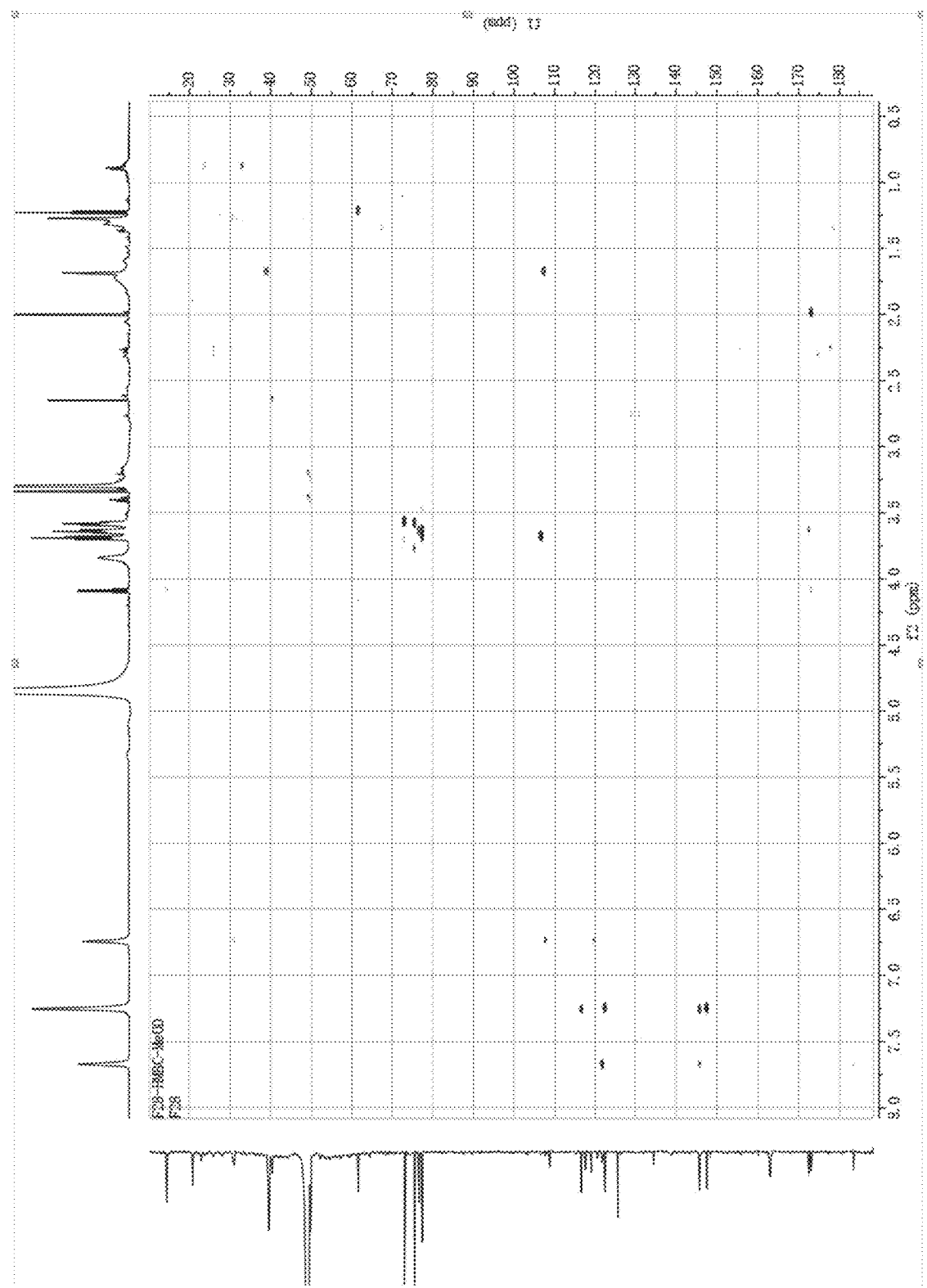

FIG. 35 HMBC spectrum of cC (800 MHz, CD3OD).

Figure 36:
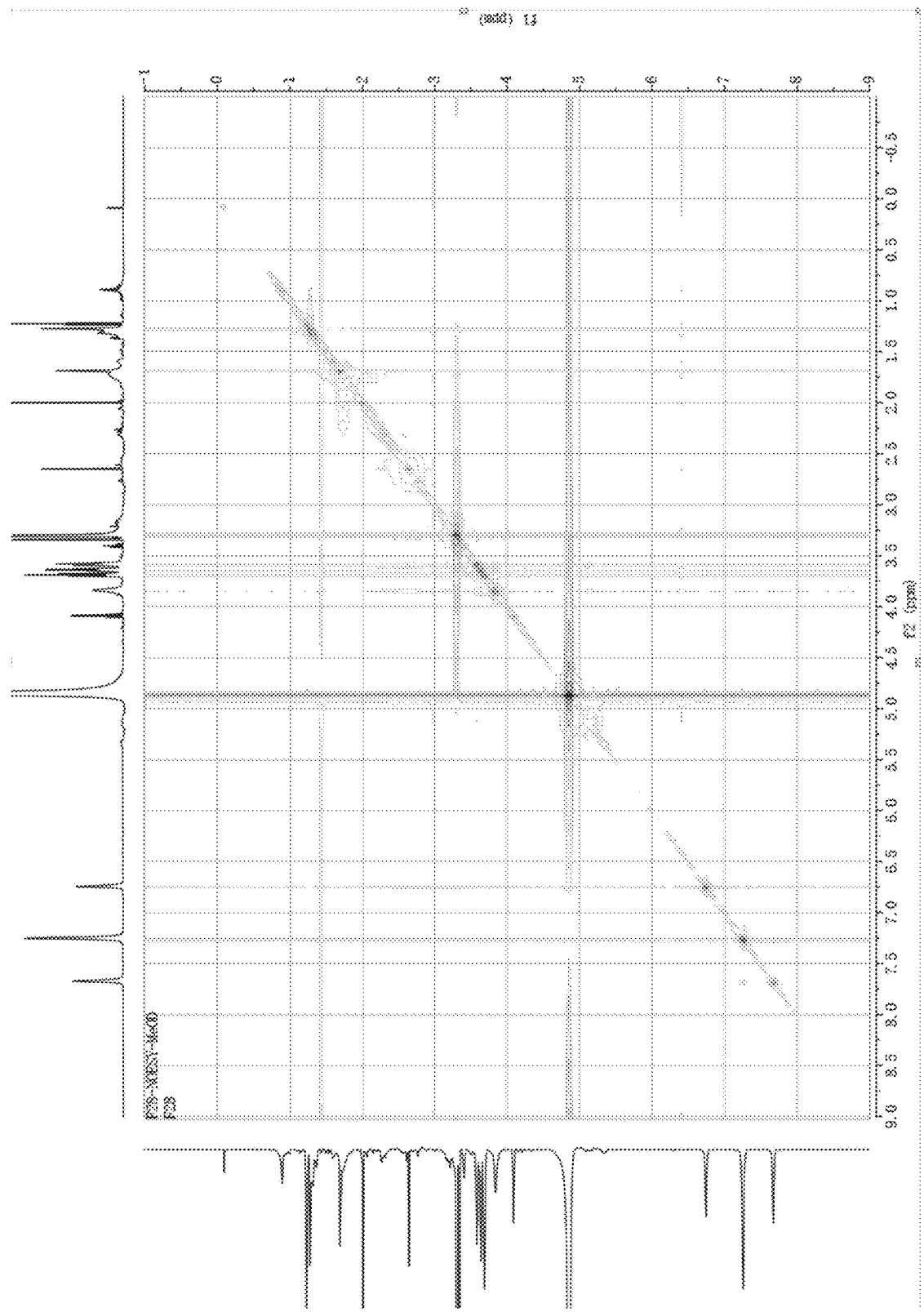

FIG. 36 NOESY spectrum of cC (800 MHz, CD3OD).

Figure 37:
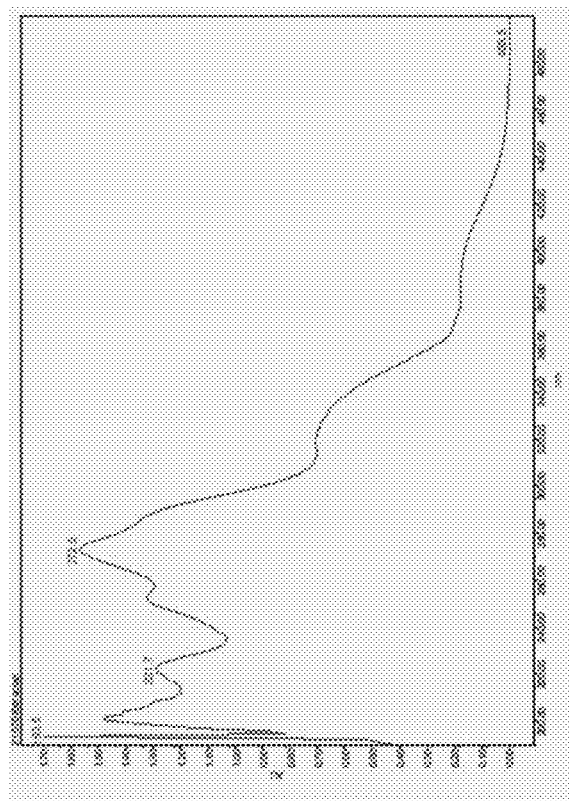
Figure 37:
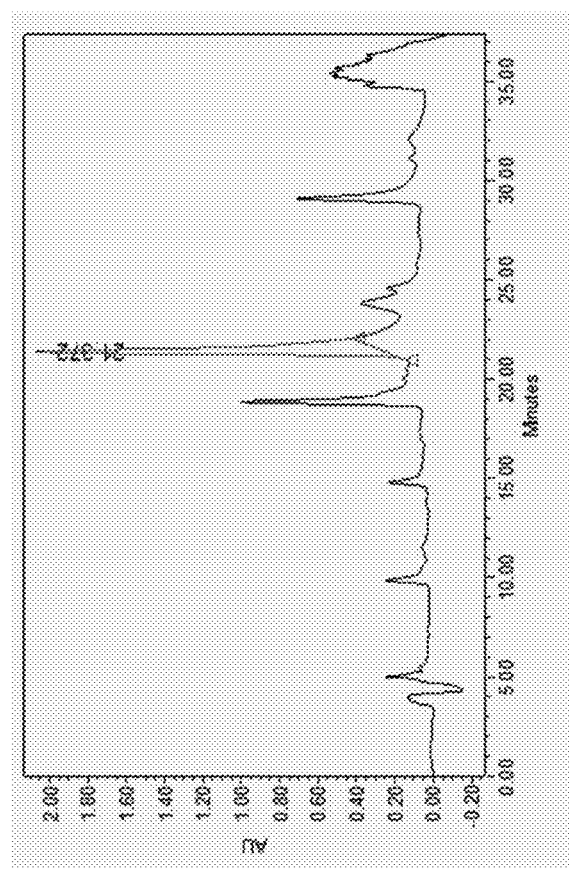

FIG. 37 Isolation of compound chrexanthominc D (cD) and its UV spectrum.

Figure 38:
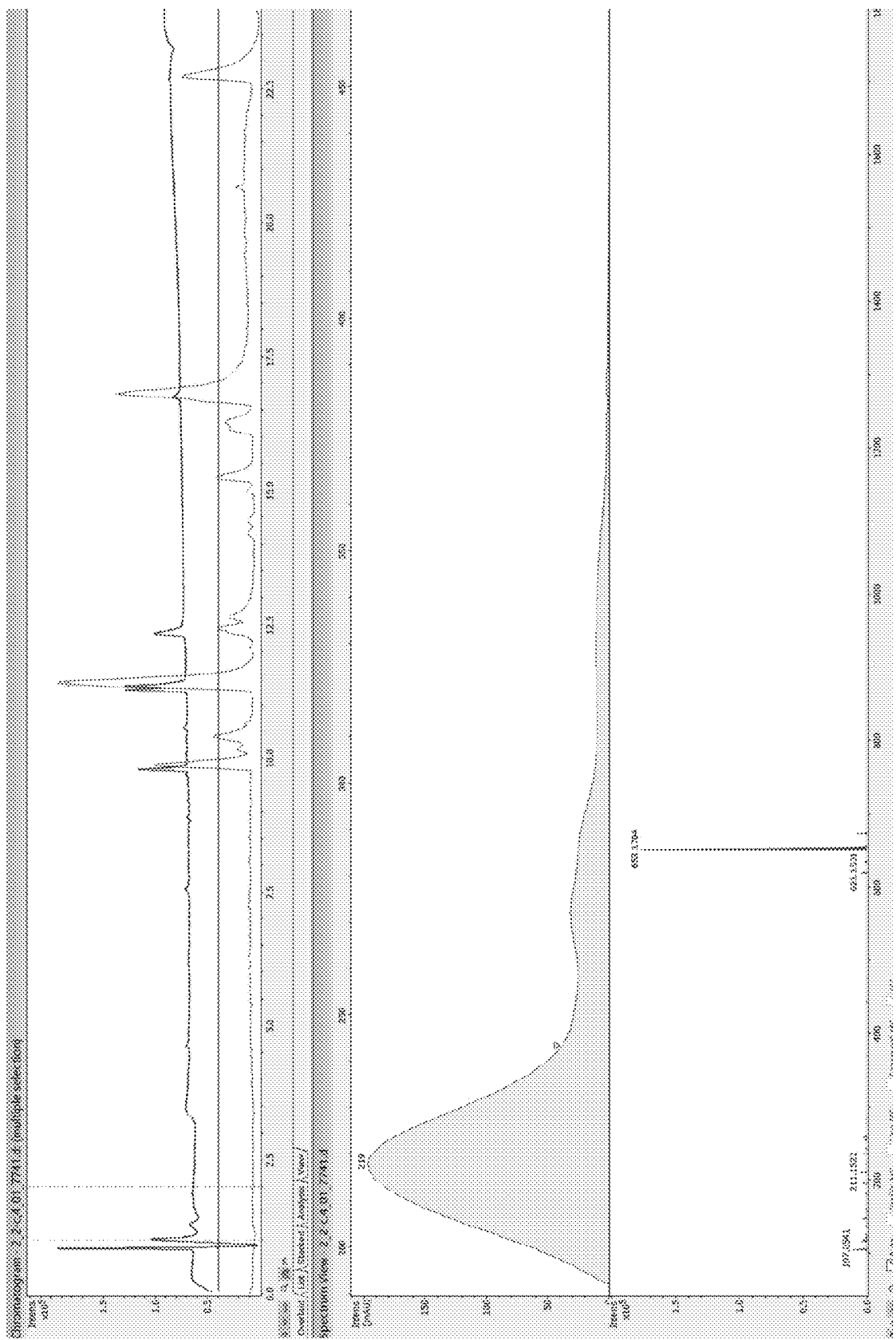

FIG. 38 Positive ion LCMS spectrum of cD (found: 653.1784)

Figure 39:
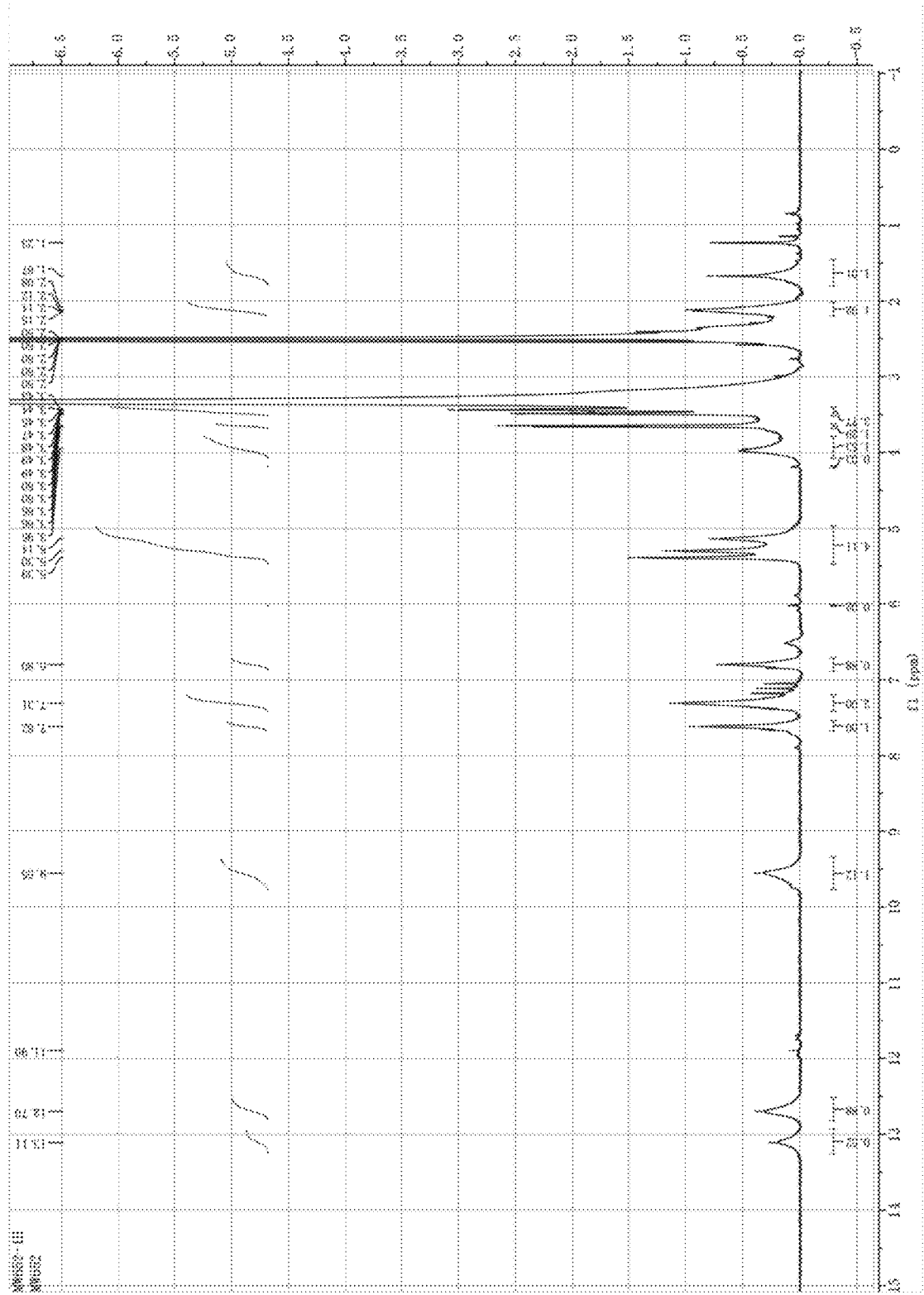

FIG. 39 1H NMR spectrum of cD (800 MHz, DMSO-d6)

Figure 40:
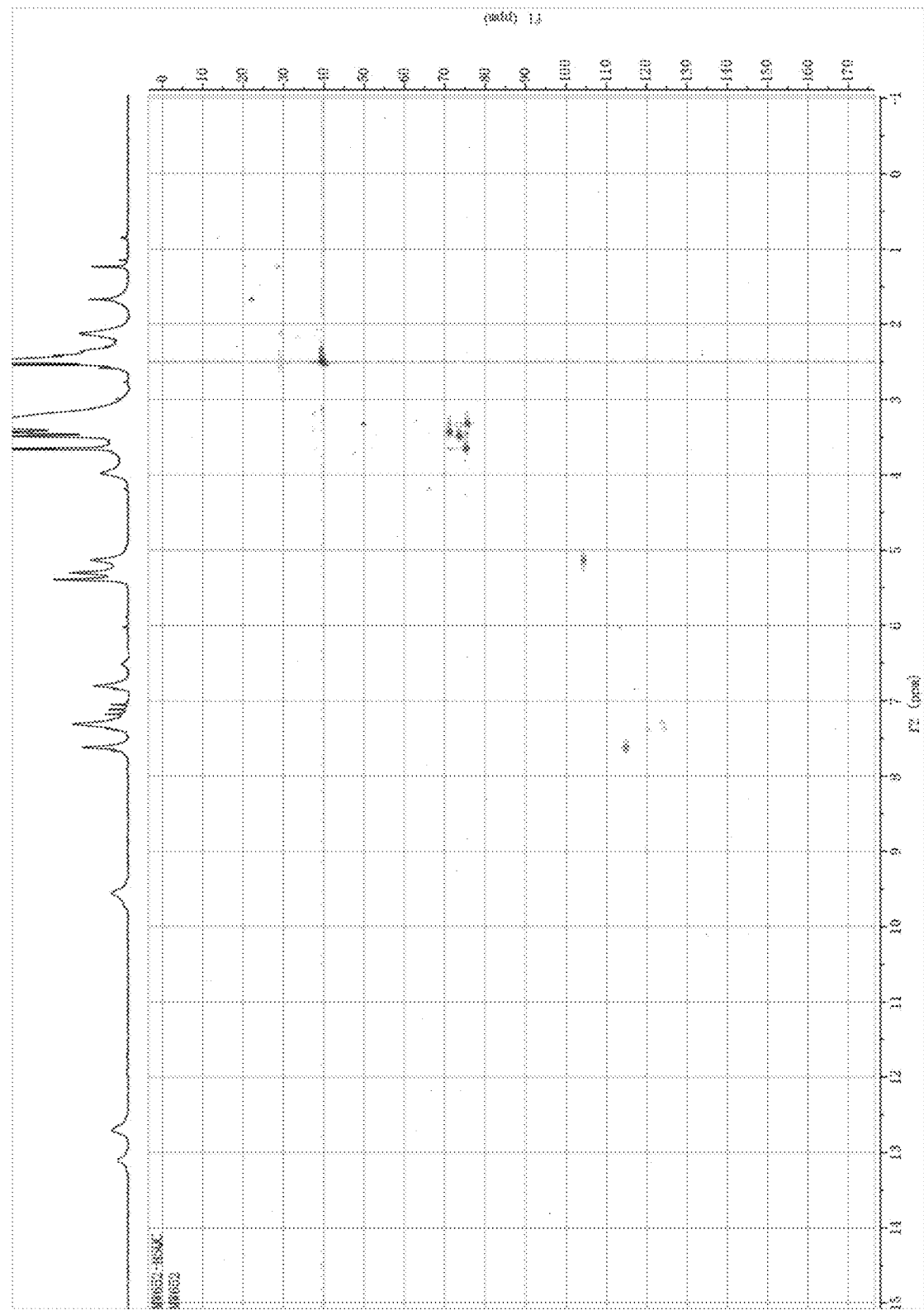

FIG. 40 HSQC spectrum of cD (800 MHz, DMSO-d6)

Figure 41:
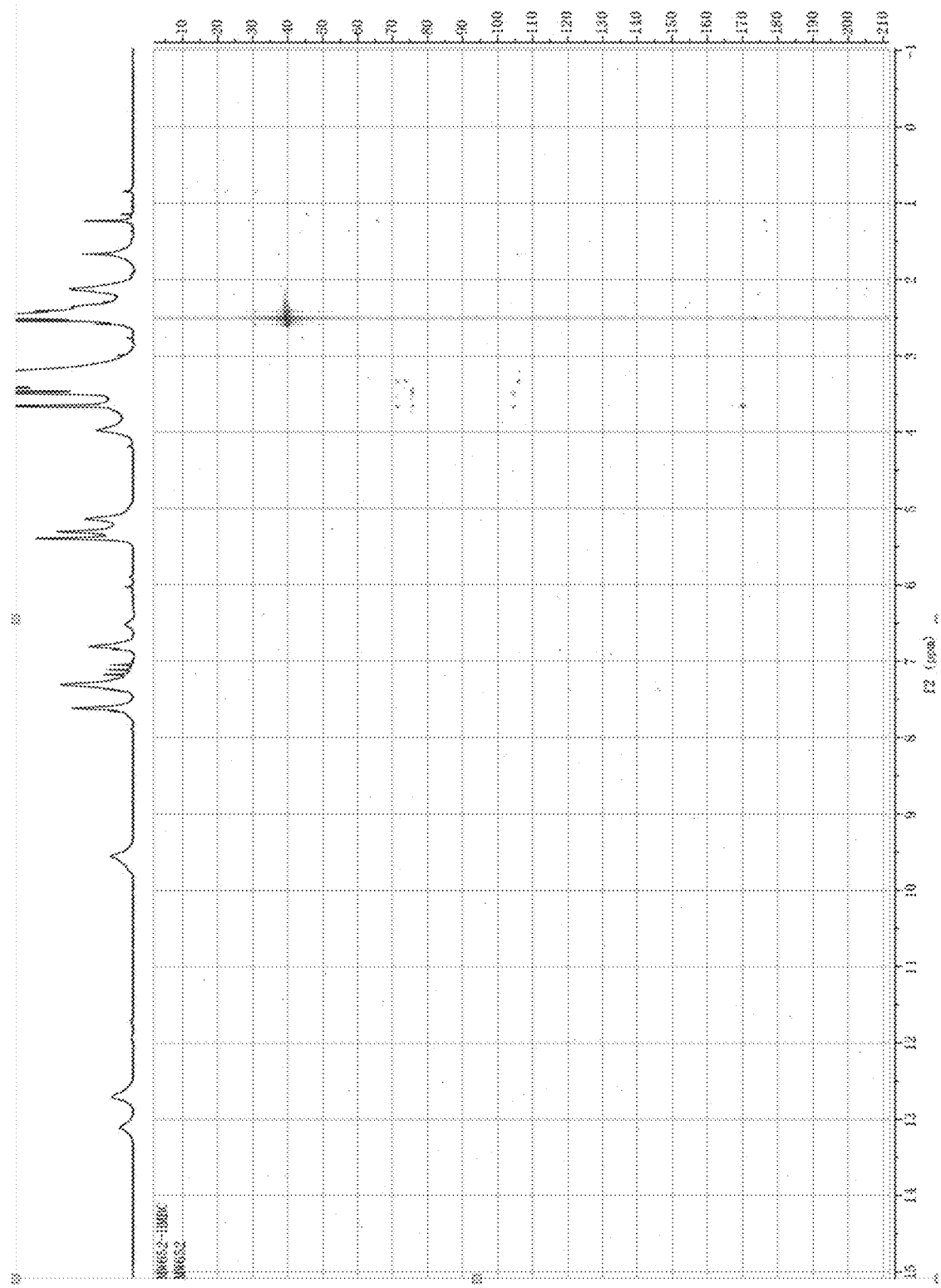

FIG. 41 HMBC spectrum of cD (800 MHz, DMSO-d6)

Figure 42:
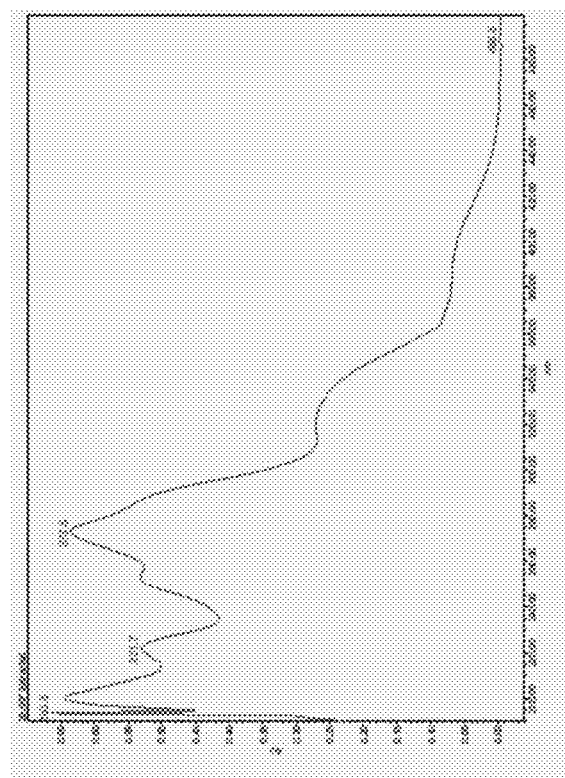
Figure 42:
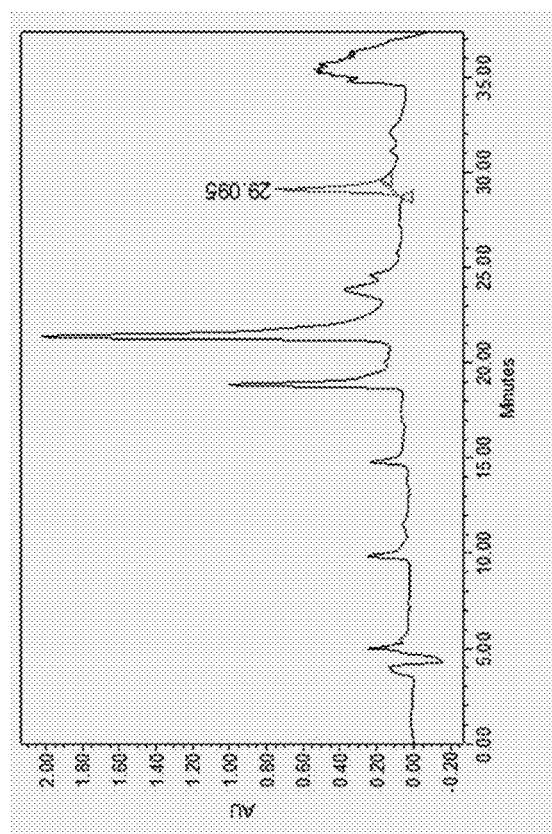

FIG. 42 Isolation of compound chrexanthomycin E (cE) and its UV spectrum.

Figure 43:
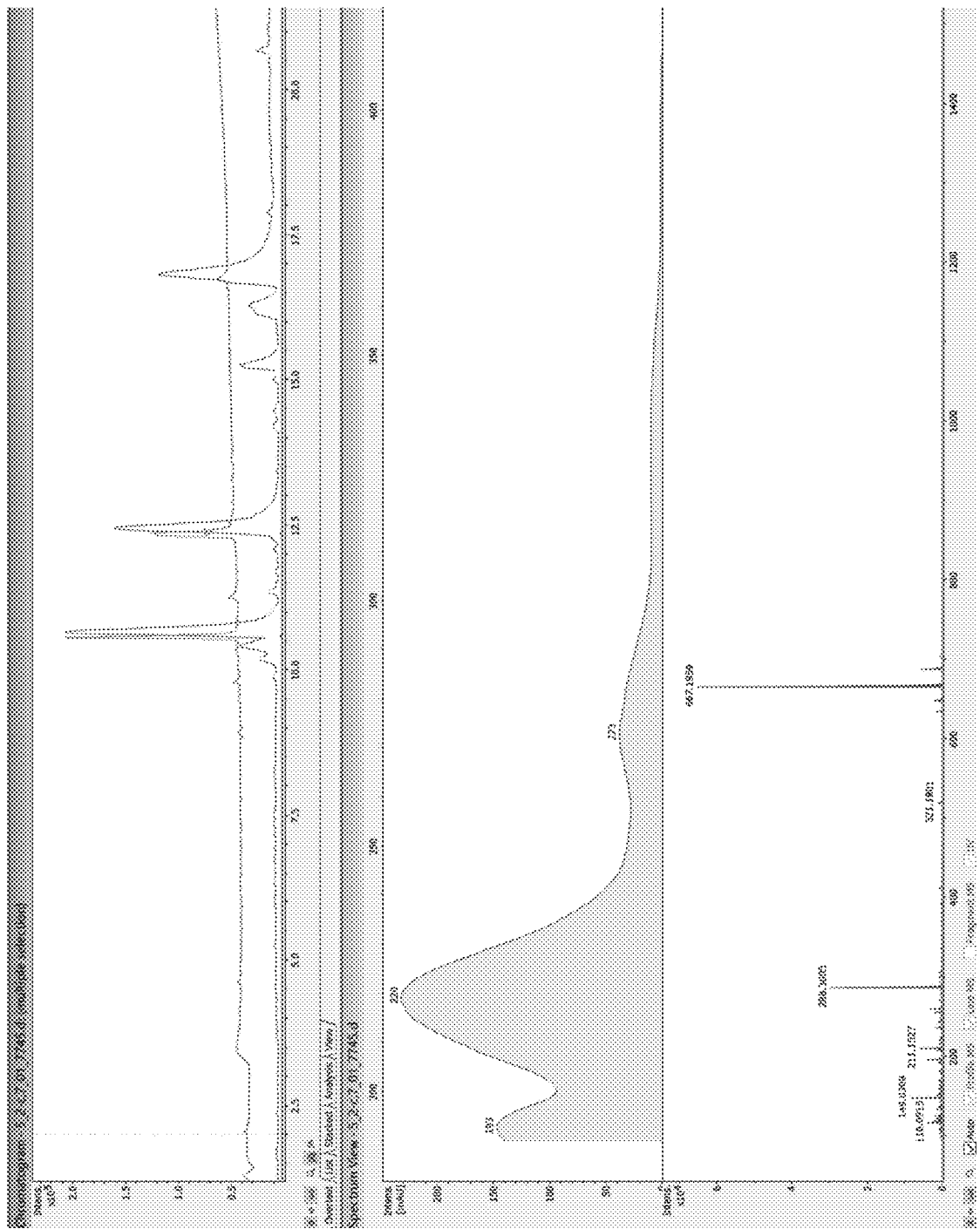

FIG. 43 Positive ion LCMS spectrum of cE (found: 667.1959)

Figure 44:
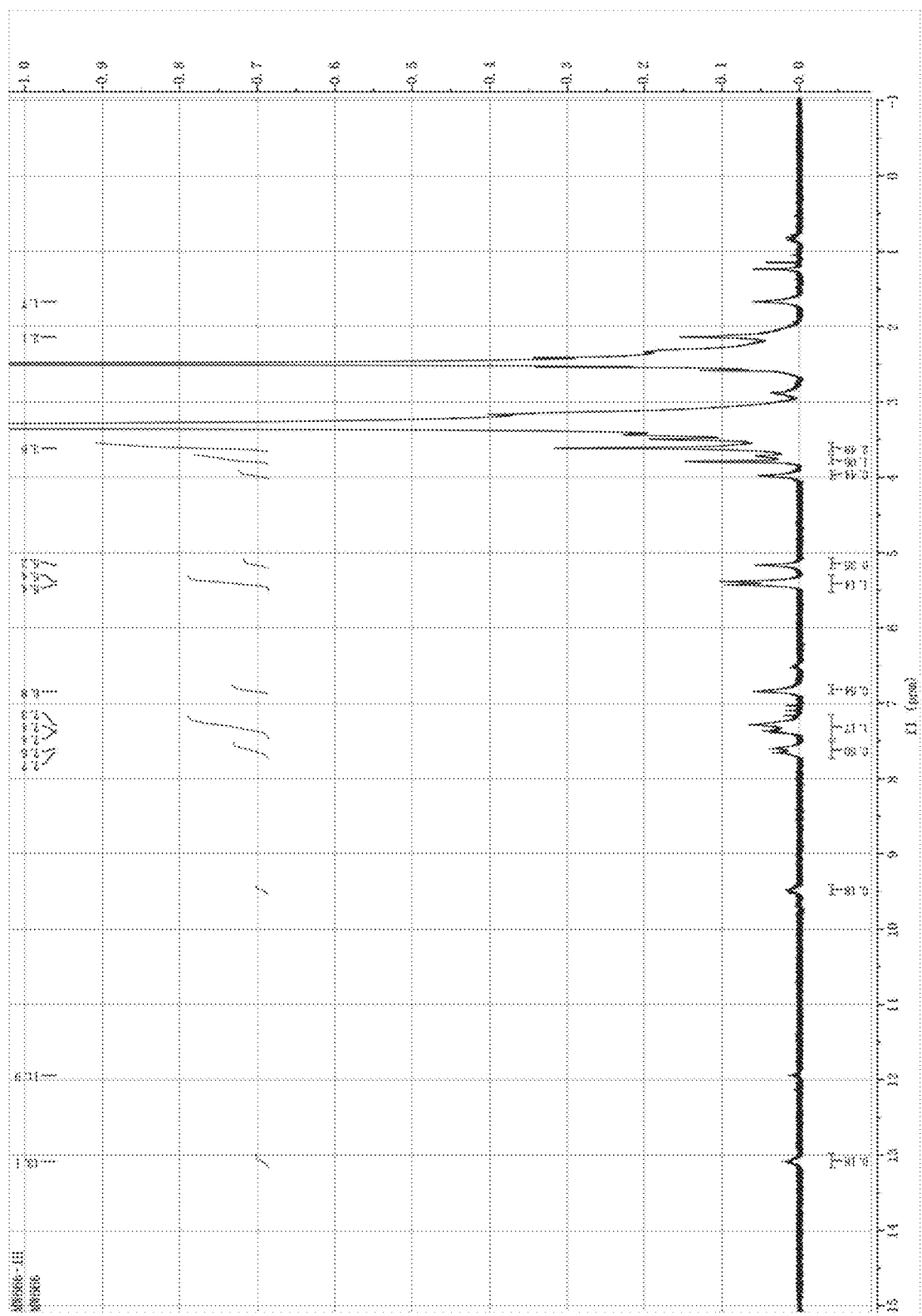

FIG. 44 1H NMR spectrum of cE (800 MHz, DMSO-d6)

Figure 45:
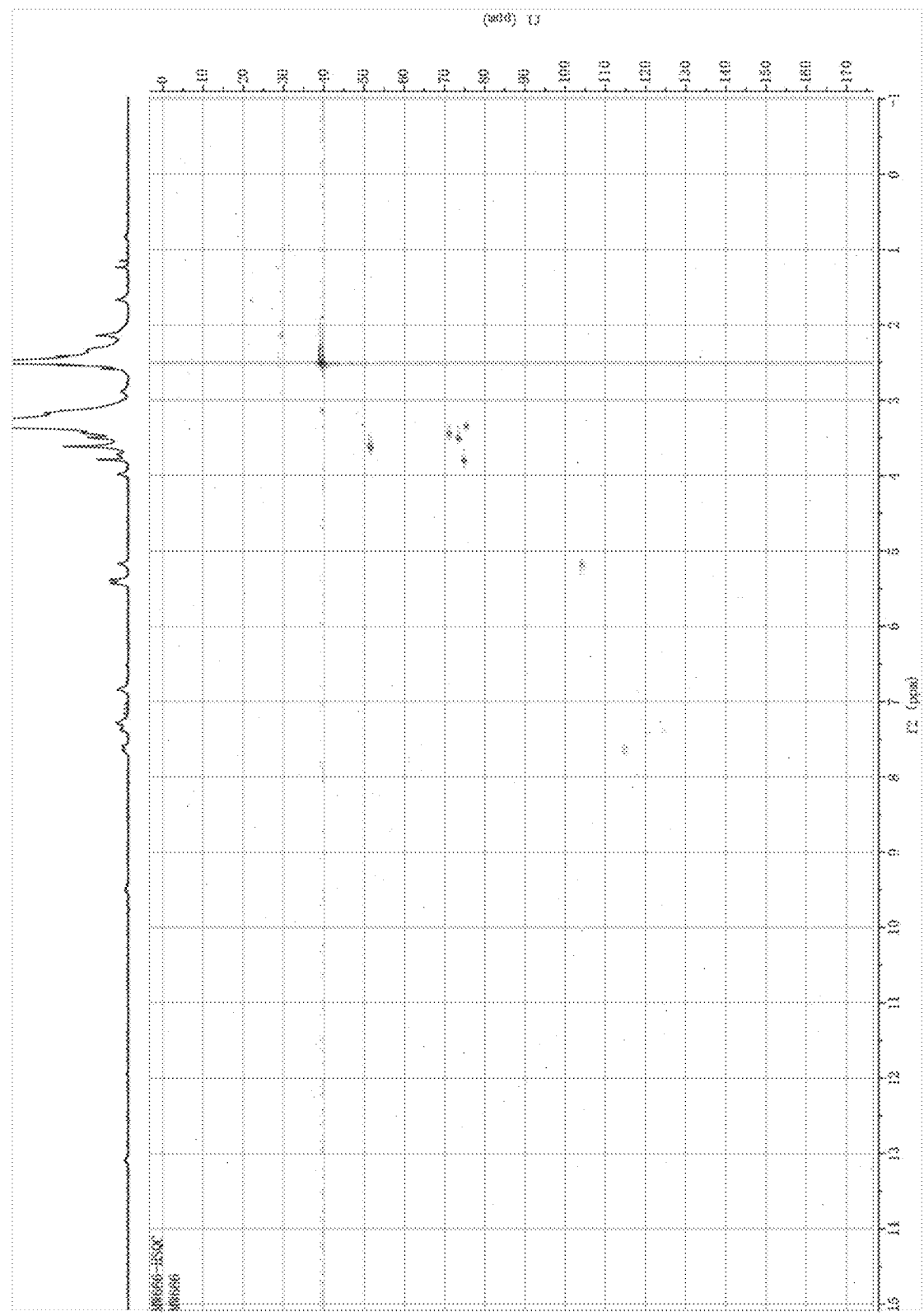

FIG. 45 HSQC spectrum of cE (800 MHz, DMSO-d6)

Figure 46:
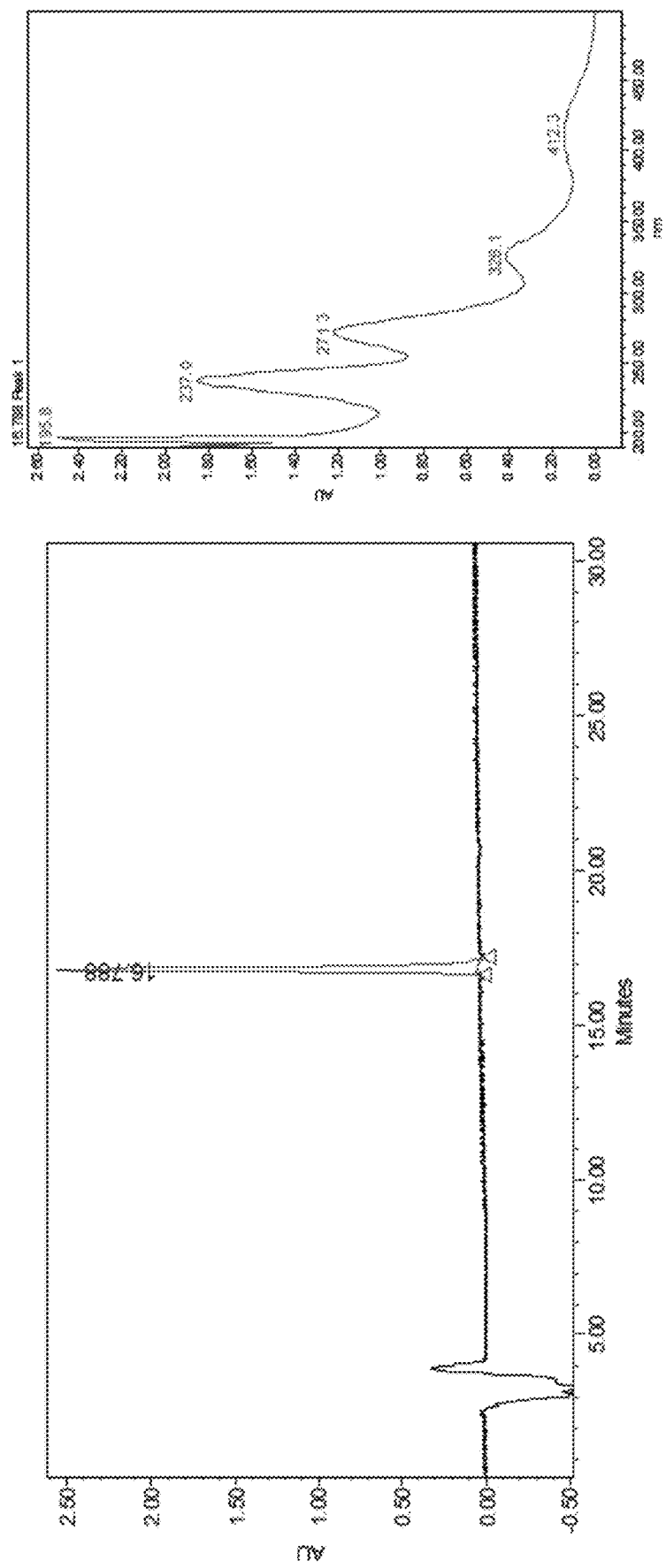

FIG. 46 Isolation of compound chrexanthomycin F (cF) and its UV spectrum.

Figure 47:
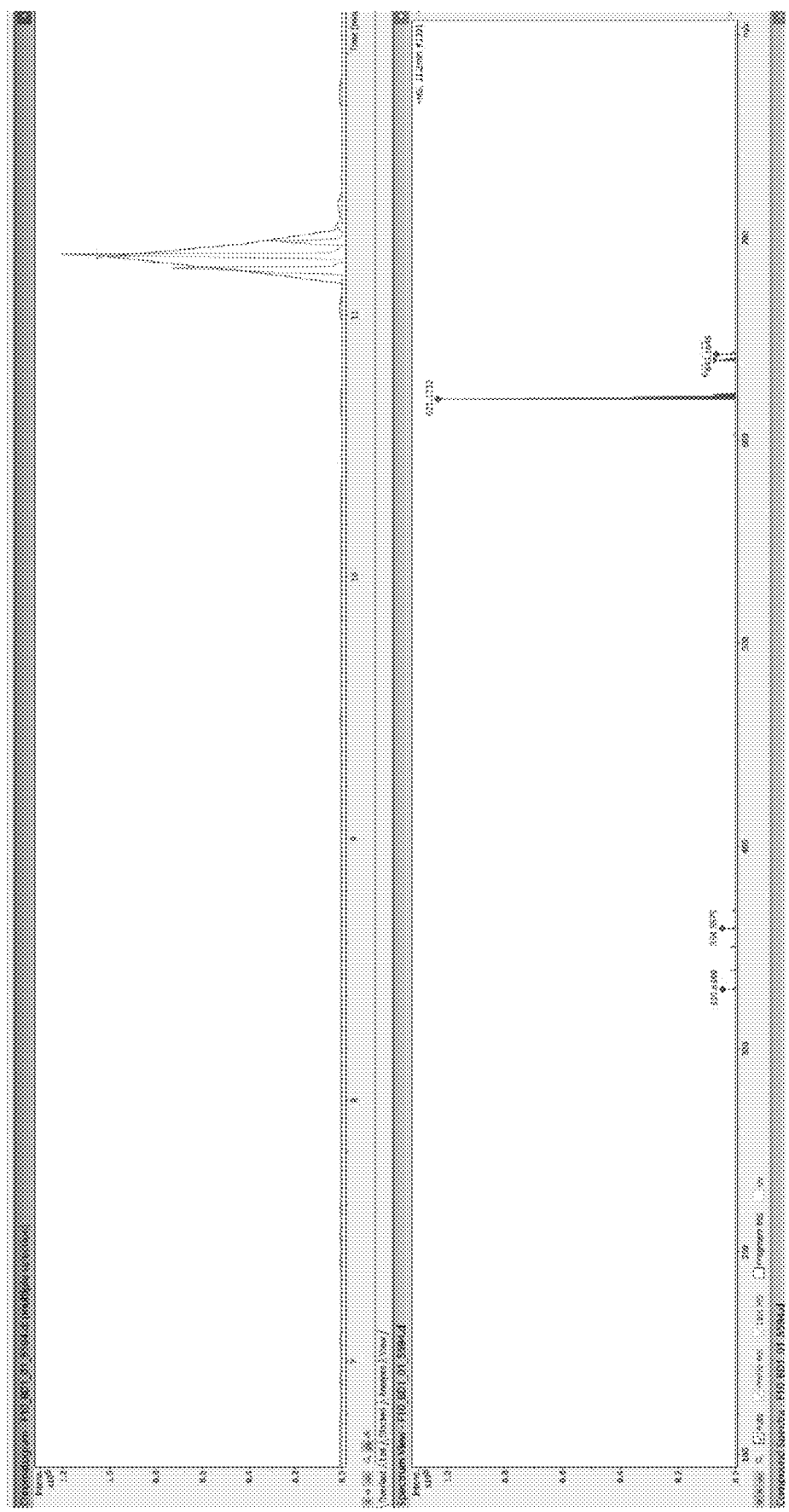

FIG. 47 Positive ion HRMS spectrum of cF (Calc: 621.1239, found: 621.1232)

Figure 48:
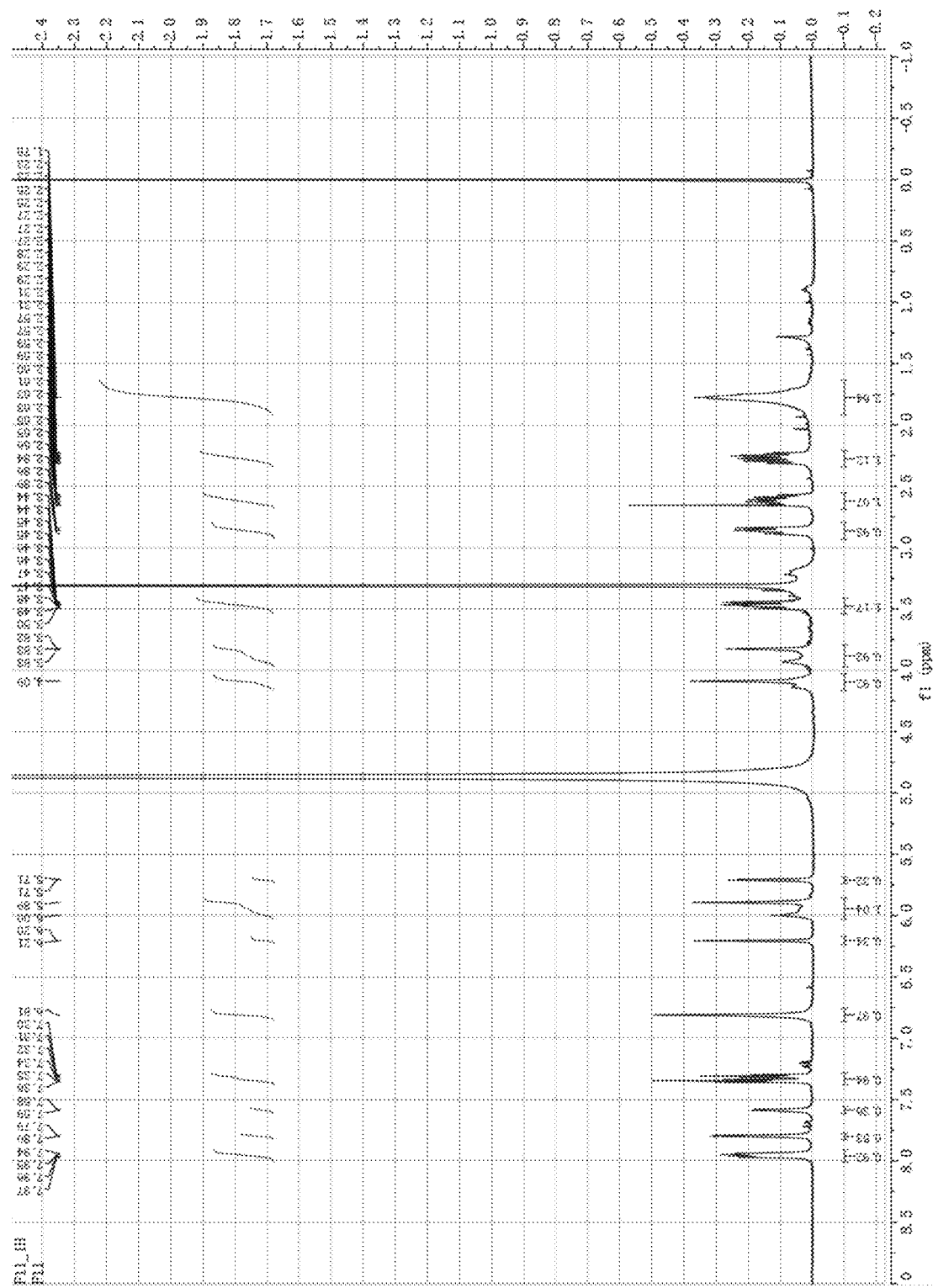

FIG. 48 1H NMR spectrum of cF (800 MHz, CD3OD)

Figure 49:
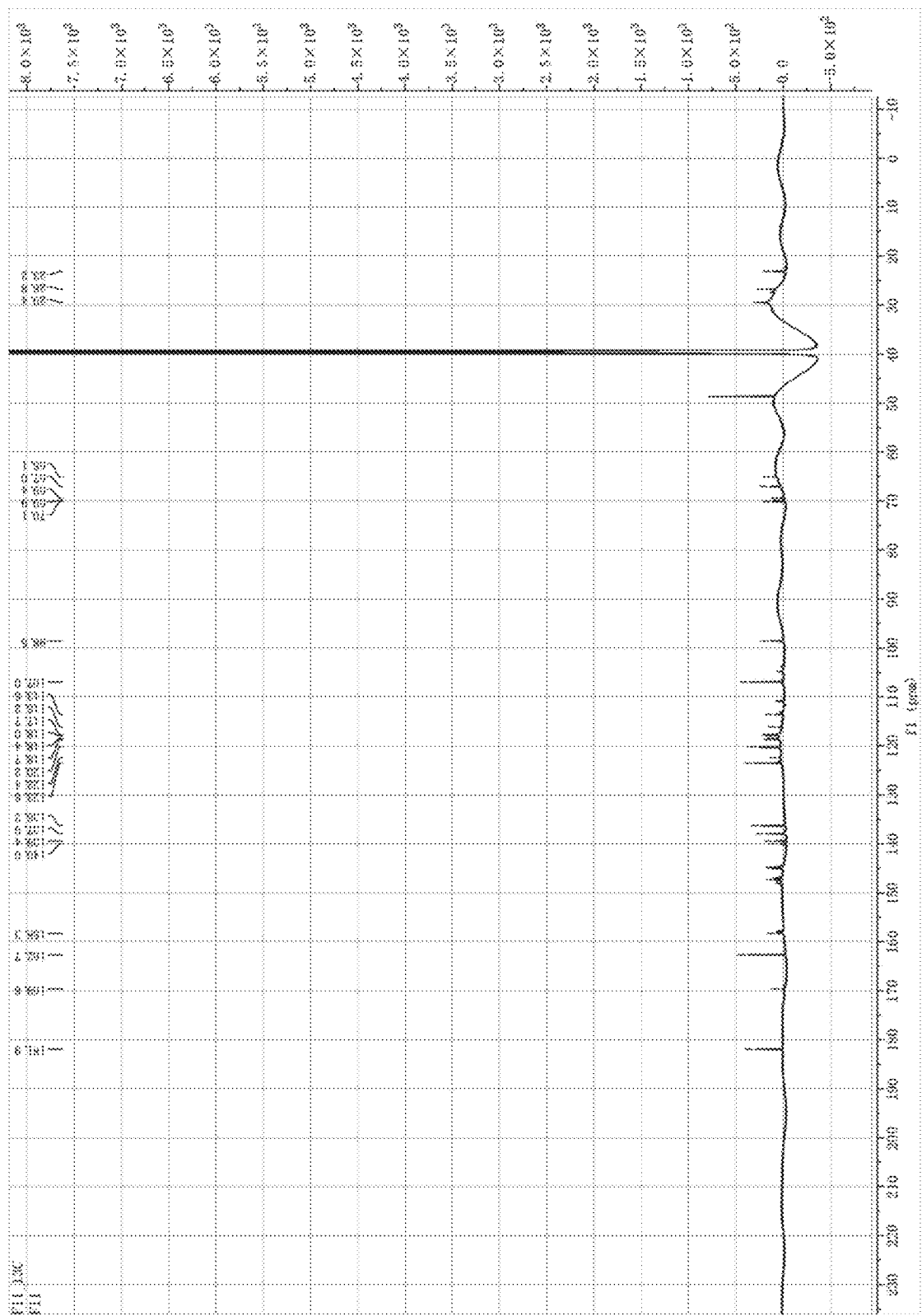

FIG. 49 13C NMR spectrum of cF (200 MHz, DMSO-d6)

Figure 50:
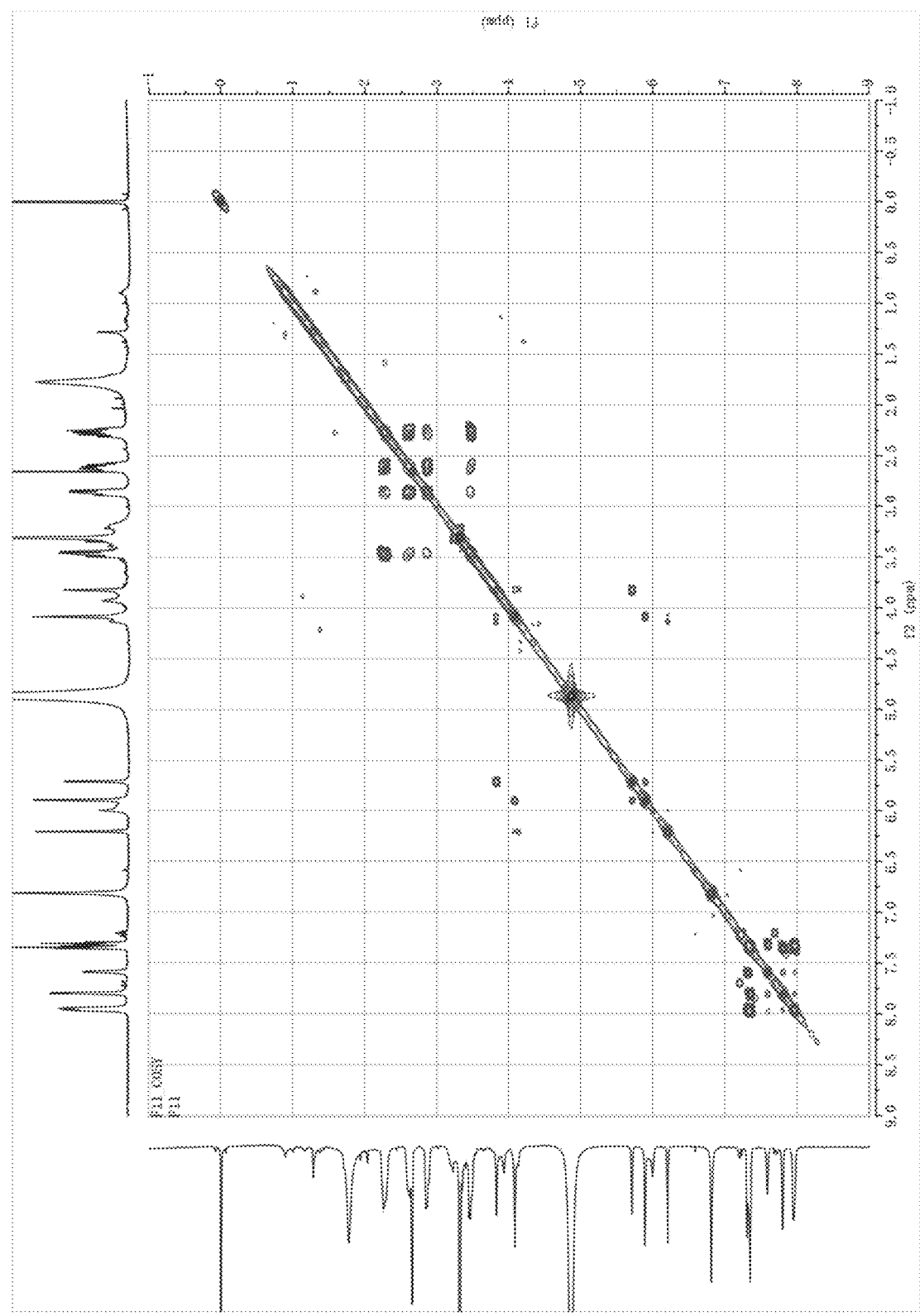

FIG. 50 COSY spectrum of cF (800 MHz, CD3OD)

Figure 51:
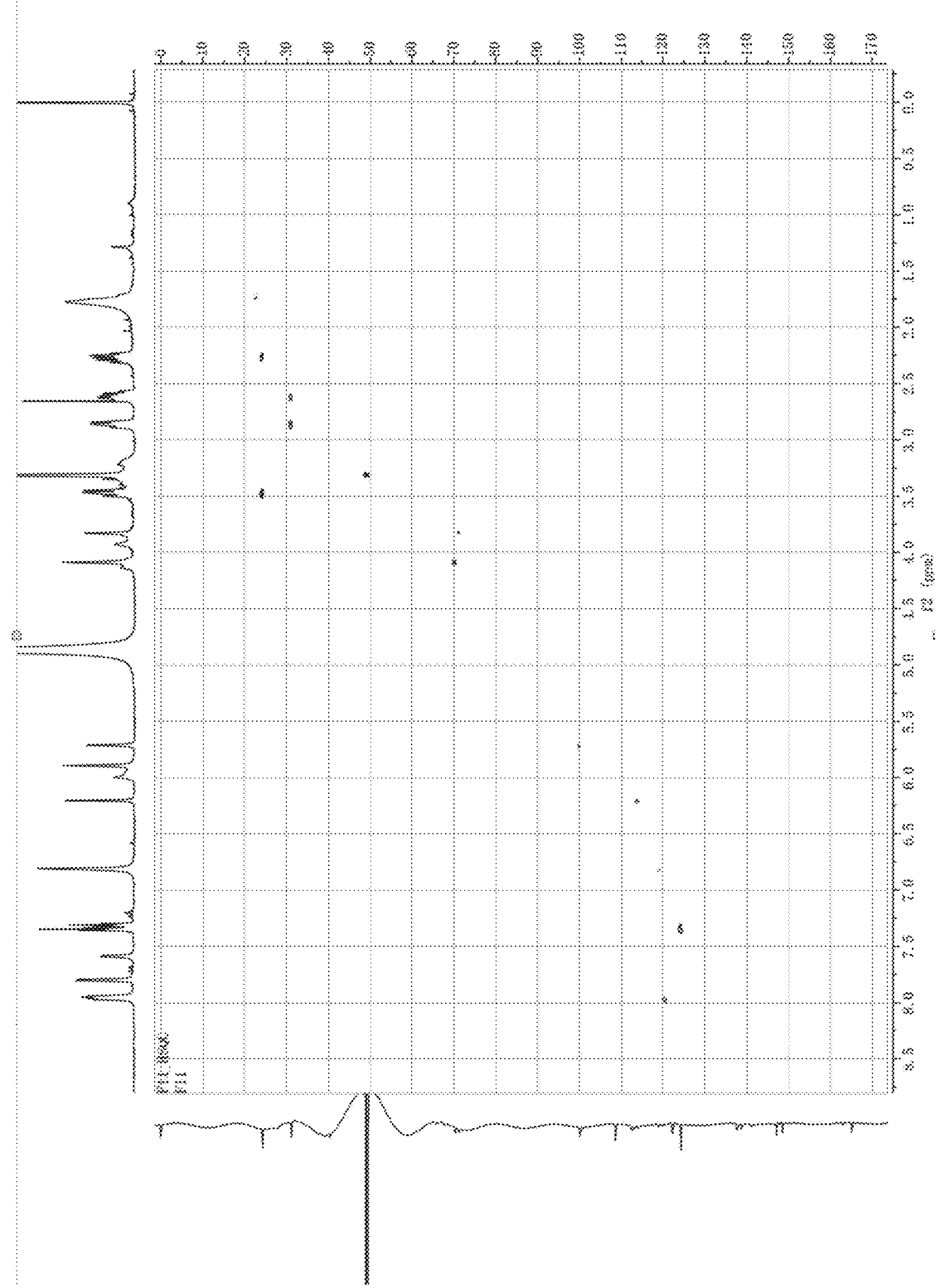

FIG. 51 HSQC spectrum of cF (800 MHz, CD3OD)

Figure 52:
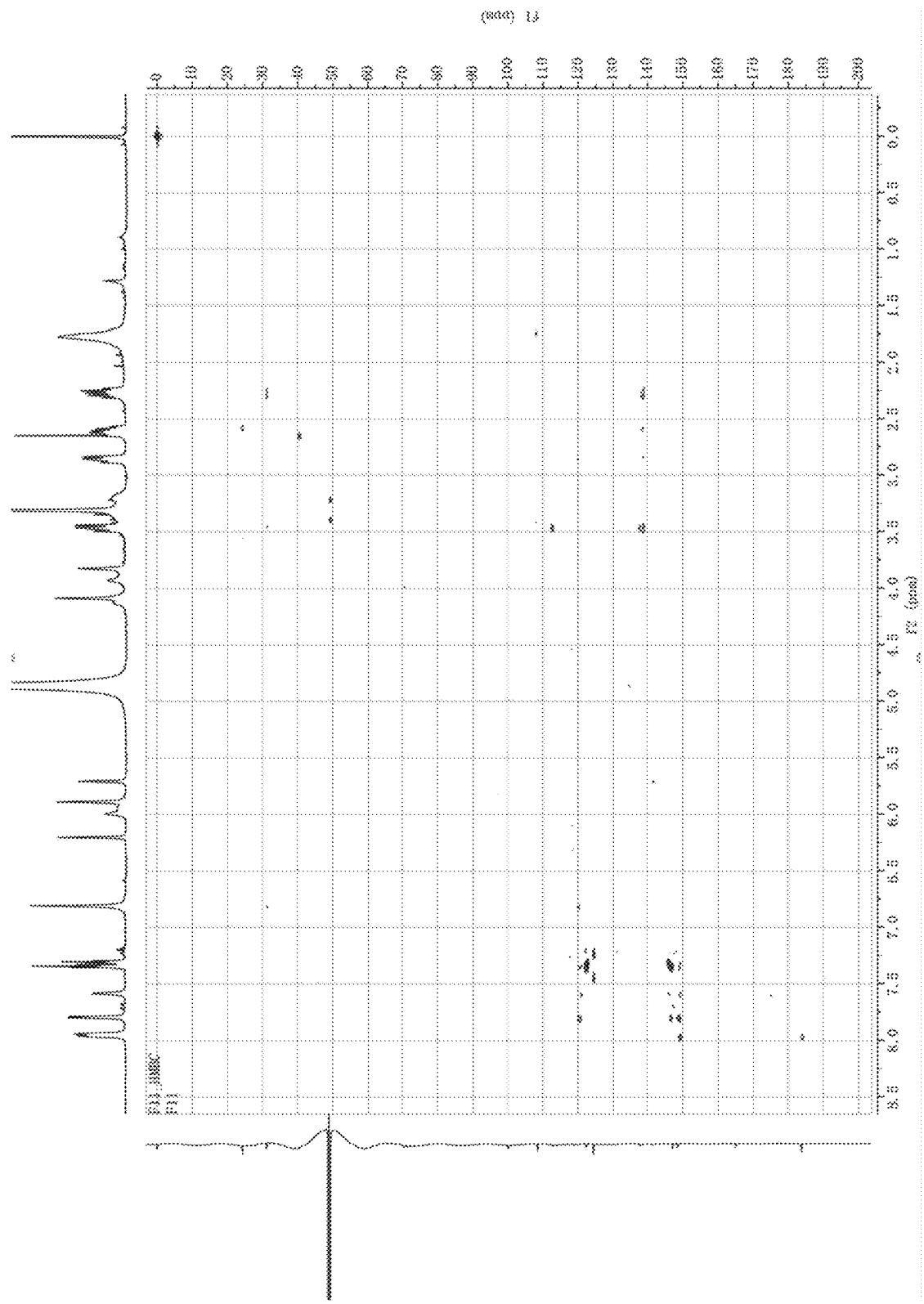

FIG. 52 HMBC spectrum of cF (800 MHz, CD3OD)

Figure 53:
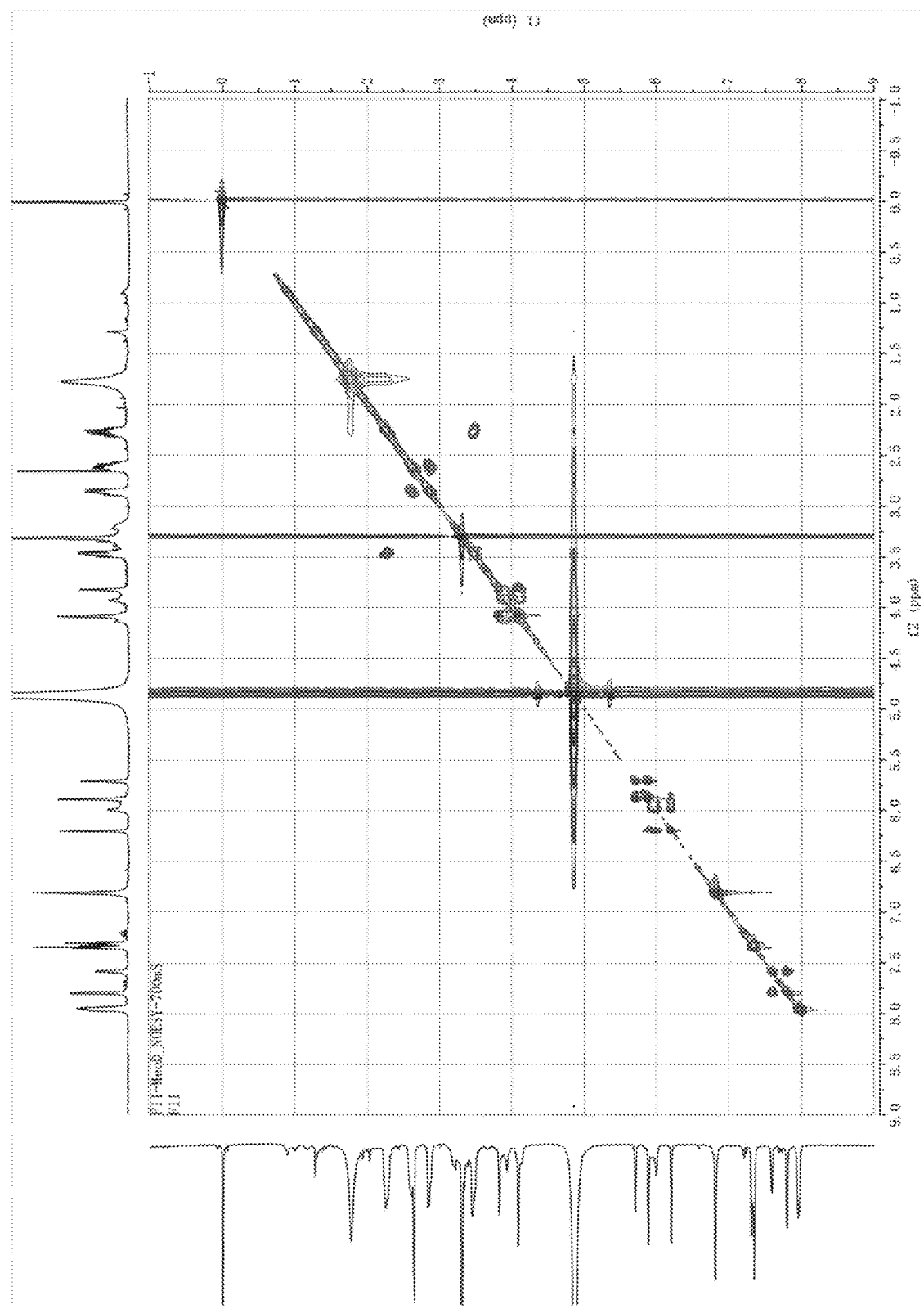

FIG. 53 NOESY spectrum of cF (800 MHz, CD3OD)

Figure 54:
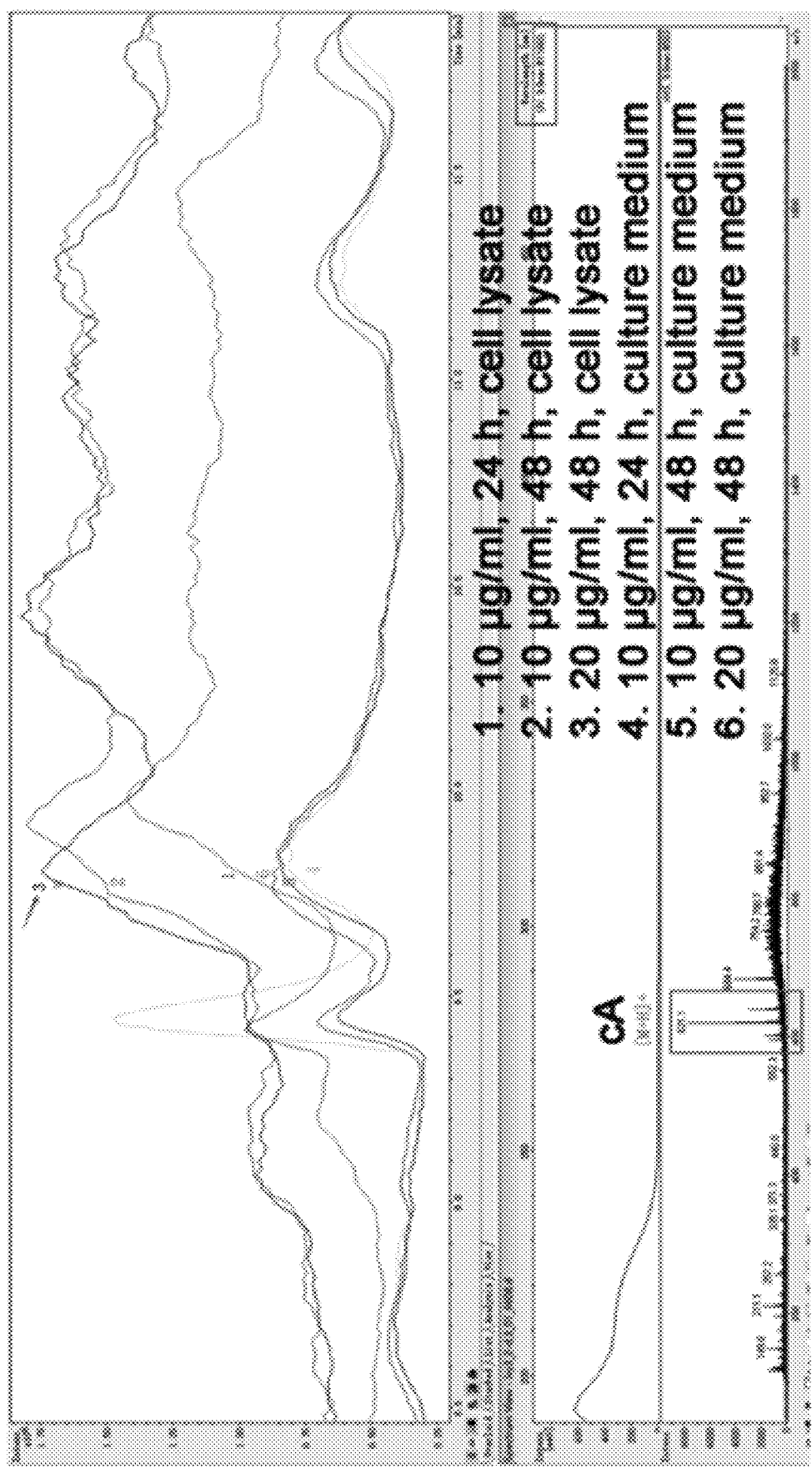

FIG. 54 Compound cA could enter into cells.

Figure 55:
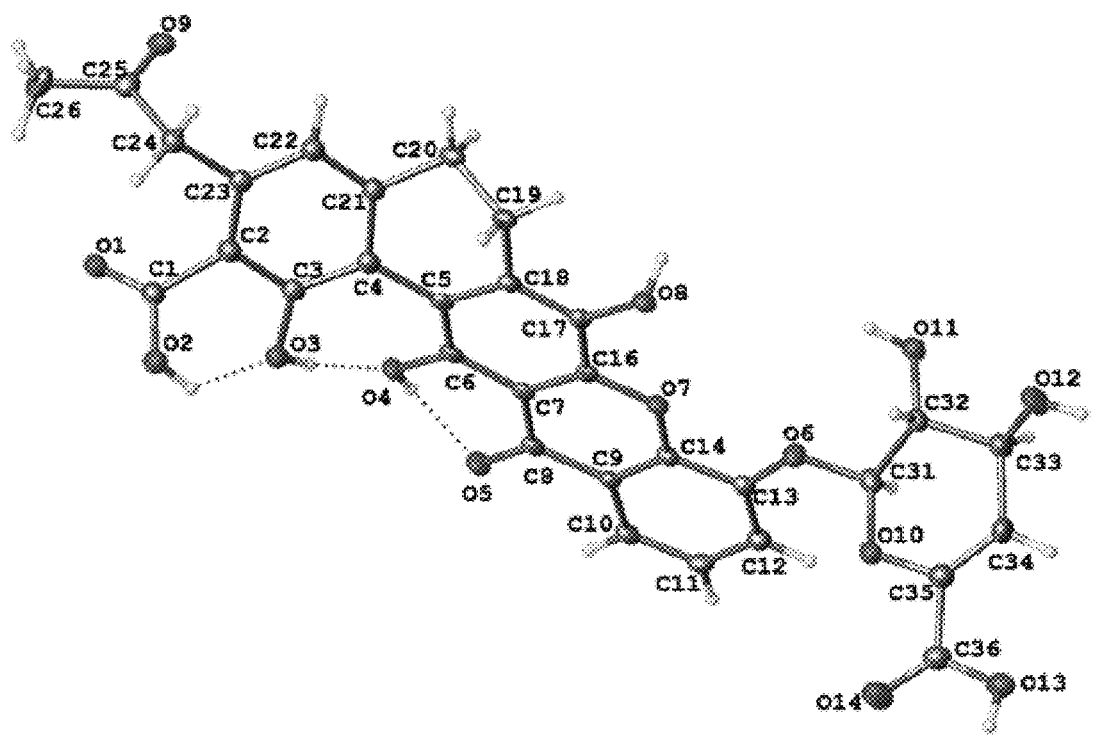
Figure 55:
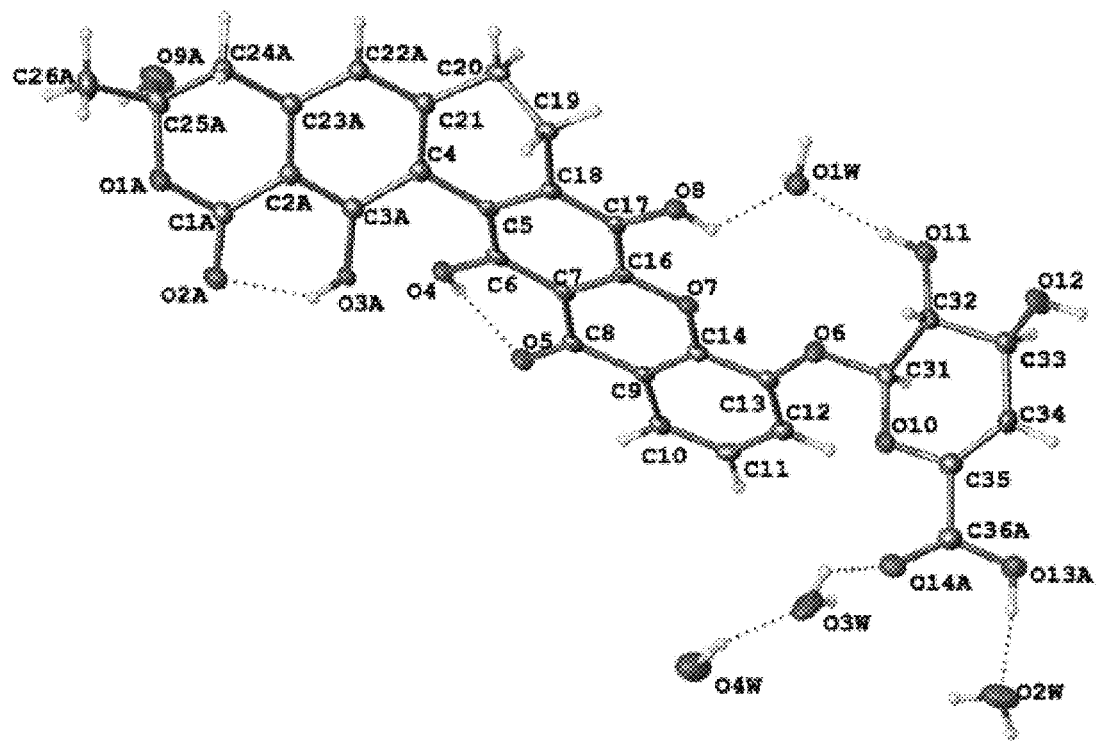

FIG. 55 Open and cyclic form single-crystal structure of cA.

BRIEF DESCRIPTION OF THE SEQUENCES

SEQ ID NO: 1: Target Probe
SEQ ID NO: 2: Control Probe
SEQ ID NO: 3: human telomeric variant
SEQ ID NO: 4: DNA quadruplex
SEQ ID NO: 5: DNA quadruplex
SEQ ID NO: 6: hexanucleotide repeat
SEQ ID NO: 7: human telomeric quadruplex
SEQ ID NO: 8: RNA quadruplex

DETAILED DISCLOSURE OF THE INVENTION

Selected Definitions

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," include the phrases "consisting essentially of," "consists essentially of," "consisting," and "consists."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed.

In the present disclosure, ranges are stated in shorthand, to avoid having to set out at length and describe each and every value within the range. Any appropriate value within the range can be selected, where appropriate, as the upper value, lower value, or the terminus of the range. For example, a range of 1-10 represents the terminal values of 1 and 10, as well as the intermediate values of 2, 3, 4, 5, 6, 7, 8, 9, and all intermediate ranges encompassed within 1-10, such as 2-5, 2-8, and 7-10. Also, when ranges are used herein, combinations and sub-combinations of ranges (e.g., subranges within the disclosed range) and specific embodiments therein are intended to be explicitly included.

In certain embodiments of the invention a subject is a mammal. Non-limiting examples of a mammal treatable according to the methods of the current invention include mouse, rat, dog, guinea pig, cow, horse, cat, rabbit, pig, monkey, ape, chimpanzee, and human. Additional examples of mammals treatable with the methods of the current invention are well known to a person of ordinary skill in the art and such embodiments are within the purview of the current invention.

For the purposes of this invention the terms "treatment, treating, treat" or equivalents of these terms refer to healing, alleviating, relieving, altering, remedying, ameliorating, improving, or affecting the condition or the symptoms of a subject suffering with a disease, for example, a neurodegenerative disorder. The subject to be treated can be suffering from or at risk of developing the disorder, for example, a neurodegenerative disorder, including, for example, Alzheimer's disease (AD), Parkinson's disease (PD), amyotrophic lateral sclerosis (ALS), Huntington's disease (HD), multiple sclerosis, epilepsy, stroke, alcohol withdrawal, progressive supranuclear palsy (PSP), Pick's disease (PiD), corticobasal degeneration (CBD), or frontotemporal dementia or parkinsonism linked to chromosome 17 (FTDP-17) or be at risk of developing an AD, PD, ALS, HD, multiple sclerosis, epilepsy, stroke, alcohol withdrawal, PSP, PiD, CBD, or FTDP-17. When provided therapeutically, the compound can be provided at (or after) the onset of a symptom. The therapeutic administration of the substance serves to attenuate any actual symptom.

For the purposes of this invention, the terms "preventing, preventive, prophylactic" or equivalents of these terms are indicate that the compounds of the subject invention are provided in advance of any disease symptoms and are a separate aspect of the invention (i.e., an aspect of the invention that is distinct from aspects related to the terms "treatment, treating, treat" or equivalents of these terms which refer to healing, alleviating, relieving, altering, remedying, ameliorating, improving, or affecting the condition or the symptoms of a subject suffering with a neurodegenerative disorder). The prophylactic administration of the compounds of the subject invention serves to prevent, reduce the likelihood, or attenuate one or more subsequent symptoms or disease.

By "therapeutically effective dose," "therapeutically effective amount", or "effective amount" is intended to be an amount of a compounds of the subject invention disclosed herein that, when administered to a subject, decreases the number or severity of symptoms AD, PD, ALS, HD, multiple sclerosis, epilepsy, stroke, alcohol withdrawal, PSP, PiD, CBD, or FTDP-17, or reduces any increase in symptoms, or improve the clinical course of the disease as compared to untreated subjects. "Positive therapeutic response" refers to, for example, improving the condition of at least one of the symptoms of AD, PD, ALS, HD, multiple sclerosis, epilepsy, stroke, alcohol withdrawal, PSP, PiD, CBD, or FTDP-17.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual. Generally, the dosage of the compounds of the subject invention will vary depending upon such factors as the patient's age, weight, height, sex, general medical condition and previous medical history. In specific embodiments, it may be desirable to administer the compounds of the subject invention in the range of about 1 mg/kg to about 50 g/kg, preferably, about 100 mg/kg to about 50 g/kg, or more preferably, about 1 g/kg to about 10 g/kg.

In some embodiments of the invention, the method comprises administration of multiple doses of the compounds of the subject invention. The method may comprise administration of 1, 2, 3, 4, 5, 6, 7, 8, 9, 10, 15, 20, 25, 30, 35, 40, or more therapeutically effective doses of a composition comprising the compounds of the subject invention as described herein. In some embodiments, doses are administered over the course of 1 day, 2 days, 3 days, 4 days, 5 days, 6 days, 7 days, 10 days, 14 days, 21 days, 30 days, or more than 30 days. The frequency and duration of administration of multiple doses of the compositions is such as to reduce or prevent AD, PD, ALS, HD, multiple sclerosis, epilepsy, stroke, alcohol withdrawal, PSP, PiD, CBD, or FTDP-17 and thereby treat or prevent a neurodegenerative disorder. Moreover, treatment of a subject with a therapeutically effective amount of the compounds of the invention can include a single treatment or can include a series of treatments. It will also be appreciated that the effective dosage of a compound used for treatment may increase or decrease over the course of a particular treatment. Changes in dosage may result and become apparent from the results of diagnostic assays for detecting neurodegenerative disorders known in the art and described herein. In some embodiments of the invention, the method comprises administration of the compounds at several time per day, including but not limiting to 2 times per day, 3 times per day, and 4 times per day.

Compounds

In preferred embodiments, the compositions and methods according to the subject invention utilize isolated chrexanthomycin A (cA) and analogs thereof, including chrexanthomycin B (cB), chrexanthomycin C (cC), chrexanthomycin D (cD), chrexanthomycin E (cE), chrexanthomycin F (cF) and/or bacterial culture extracts containing compounds cA, cB, cC, cD, cE and/or cF. Compounds cA, cB, cC, cD, cE and cF may be in a purified form or in a mixture of bacterial growth products, including crude extracts. Compounds cA, cB, cC, cD, cE and cF may be added to compositions at concentrations of about 0.0001 to about 5% by weight (wt %), preferably about 0.01 to about 5 wt %, and more preferably about 0.1 to about 1 wt %. In another embodiment, purified compounds cA, cB, cC, cD, cE and cF may be in combination with an acceptable carrier, in that compounds cA, cB, cC, cD, cE and cF may be presented at concentrations of about 0.0001 to about 5% (v/v), preferably, about 0.01 to about 5% (v/v), more preferably, about 0.1 to about 1% (v/v).

The following are chemical formulas of cA (formula (IV)), cB (formula (V)), cC (formula (VI)), cD (formula (VII)), cE (formula (VIII)) and cF (formula (IX)).

Formula (IV)

cA (formula (IV))

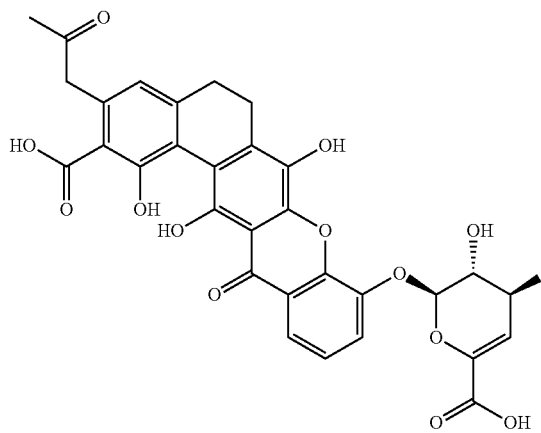

cB (formula (V))

cC (formula (VI))

cD (formula (VII))

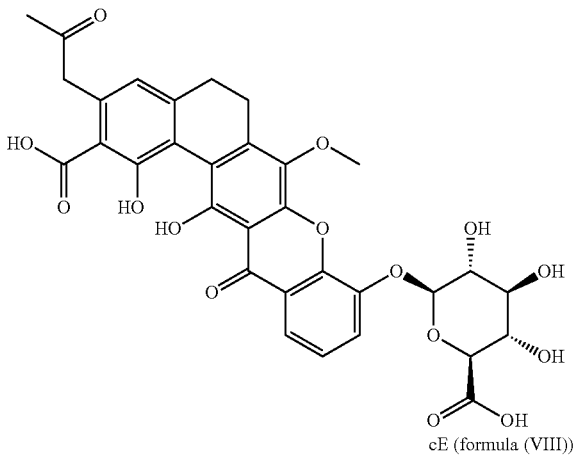

cE (formula (VIII))

cF (formula (IX))

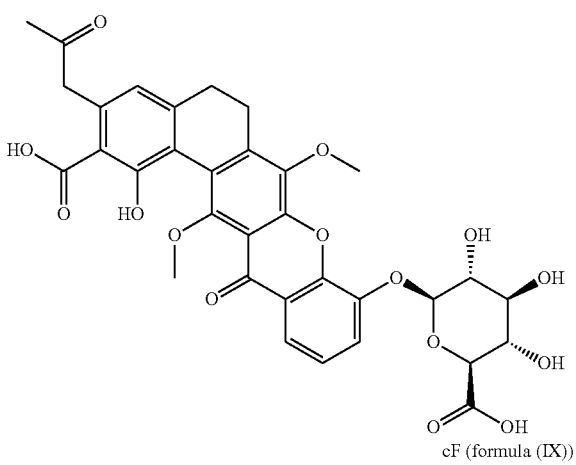

The microorganisms utilized according to the subject invention may be natural, or genetically modified microorganisms, specifically microorganisms that can synthesize the compounds of the subject invention. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In certain embodiments, the microorganisms are any bacteria that produce compounds cA, cB, cC, cD, cE or cF. Compounds cA, cB, cC, cD, cE and cF and/or associated bacteria culture extracts can be produced by bacteria, including *Streptomyces* spp. In preferred embodiments, compounds cA, cB, cC, cD, cE and cF are produced by *Streptomyces chrestomyceticus* BCC 24770 or *Streptomyces caelestis* Aw99c.

In one embodiment, the method for cultivation of microorganisms is carried out at about 5° C. to about 100° C., about 15° C. to about 60° C., about 20° C. to about 37° C., preferably, about 20° C. to about 30° C., or, more preferably, about 23° C. to about 30° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. In certain embodiments, the bacteria can undergo fermentation, said fermentation comprising contacting bacterial cells to GYM medium (4 g of yeast extract, 10 g of malt extract, and 4 g of D-glucose per liter of distilled water) or SPY media (10 g/L of starch, 2 g/L of peptone, 4 g/L of yeast extract and 20 g/L of sea salt) and, optionally, about 20 to about 100 glass beads (3 mm in diameter) at about 20° C. to 37° C., preferably about 23° C. to about 30° C., for 7 to about 14 days, preferably about 7 to about 10 days, with an agitation of 160 to about 200 rpm.

In one embodiment, the compositions of the subject invention comprise a bacterial culture produced according to the subject methods.

The microbial growth byproduct produced by microorganisms of interest may be retained in the microorganisms or secreted into the liquid medium. In another embodiment, the method for producing microbial growth byproduct may further comprise steps of concentrating and purifying the microbial growth byproduct of interest. In a further embodiment, the liquid medium may contain compounds that stabilize the activity of microbial growth byproduct.

In certain embodiments, the bacterial growth conditions used to produce the subject compounds are significantly different from the growth conditions in the natural habitats of said bacteria. For example, the sea water temperature is usually below 20° C. but the culture temperature is at least 20° C., preferably about 30° C. Also, the GYM culture medium that is preferably used to grow the bacteria used to synthesize the subject compounds does not contain any sea salt, which makes the salinity different from the natural habitat. Finally, nutrients added in the culture medium, such as, for example, yeast extract, malt extract, and glucose, are far more concentrated in the bacterial growth conditions used to produce the subject compounds compared to the natural habitats.

Preparation of Compounds cA, cB, cC, cD, cE and cF and Compositions Thereof

One cA, cB, cC, cD, cE and/or cF-based product of the subject invention is simply the bacterial growth broth containing the bacteria and/or the cA, cB, cC, cD, cE and/or cF produced by the bacteria and/or any residual nutrients. The product of bacteria growth may be used directly without extraction or purification. If desired, extraction and purification can be easily achieved using standard extraction and/or purification methods or techniques.

In preferred embodiments, cA, cB, cC, cD, cE and/or cF can be extracted from bacteria by ethyl acetate to obtain the crude extract. The crude extract can be separated by the reversed-phase C18 column chromatography and eluted with 20, 40, 60, 80, and 100% acetonitrile to obtain different fractions. Compounds can be obtained in the 60% eluate monitored at a UV wavelength of 210 nm and can be further purified by semi-preparative HPLC. Compounds can be collected, freeze-dried, and dissolved in dimethyl sulfoxide (DMSO) for further biological assessments. The compounds can also be stored in other organic solvents, such as methanol, ethyl acetate, tetrahydrofuran, acetonitrile, dichloromethane, and dimethylformamide. Typical storage concentrations can range from 10 uM to 100 mM.

Upon harvesting the cA, cB, cC, cD, cE and/or cF compositions from the growth vessels, further components can be added as the harvested product is placed into containers and/or piped (or otherwise transported for use). The additives can be, for example, dyes, pigments, pH adjusting agents, buffers, salts, adhesion-promoting compounds, solvents (e.g., isopropyl alcohol, ethanol), biocides, other microbes, and other ingredients specific for an intended use.

In certain embodiments, the cA, cB, cC, cD, cE and/or cF compositions can be added to existing compositions that are traditionally used as therapeutics.

In one embodiment, the subject compositions are formulated as an orally-consumable product, such as, for example a food item, capsule, pill, or drinkable liquid. An orally deliverable pharmaceutical is any physiologically active substance delivered via initial absorption in the gastrointestinal tract or into the mucus membranes of the mouth. The topic compositions can also be formulated as a solution that can be administered via, for example, injection, which includes intravenously, intraperitoneally, intramuscularly, intrathecally, intracerebroventricularly or subcutaneously. In other embodiments, the subject compositions are formulated to be administered via the skin through a patch or directly onto the skin for local or systemic effects. The compositions can be administered sublingually, buccally, rectally, or vaginally. Furthermore, the compositions can be sprayed into the nose for absorption through the nasal membrane, nebulized, inhaled via the mouth or nose, or administered in the eye or ear.

Orally consumable products according to the invention are any preparations or compositions suitable for consumption, for nutrition, for oral hygiene, or for pleasure, and are products intended to be introduced into the human or animal oral cavity, to remain there for a certain period of time, and then either be swallowed (e.g., food ready for consumption or pills) or to be removed from the oral cavity again (e.g., chewing gums or products of oral hygiene or medical mouth washes). While an orally-deliverable pharmaceutical can be formulated into an orally consumable product, and an orally consumable product can comprise an orally deliverable pharmaceutical, the two terms are not meant to be used interchangeably herein.

Orally consumable products include all substances or products intended to be ingested by humans or animals in a processed, semi-processed, or unprocessed state. This also includes substances that are added to orally consumable products (particularly food and pharmaceutical products) during their production, treatment, or processing and intended to be introduced into the human or animal oral cavity.

Orally consumable products can also include substances intended to be swallowed by humans or animals and then digested in an unmodified, prepared, or processed state; the orally consumable products according to the invention therefore also include casings, coatings, or other encapsulations that are intended to be swallowed together with the product or for which swallowing is to be anticipated.

In one embodiment, the orally consumable product is a capsule, pill, syrup, emulsion, or liquid suspension containing a desired orally deliverable substance. In one embodiment, the orally consumable product can comprise an orally deliverable substance in powder form, which can be mixed with water or another liquid to produce a drinkable orally-consumable product.

In some embodiments, the orally-consumable product according to the invention can comprise one or more formulations intended for nutrition or pleasure. These particularly include baking products (e.g., bread, dry biscuits, cake, and other pastries), sweets (e.g., chocolates, chocolate bar products, other bar products, fruit gum, coated tablets, hard caramels, toffees and caramels, and chewing gum), alcoholic or non-alcoholic beverages (e.g., cocoa, coffee, green tea, black tea, black or green tea beverages enriched with extracts of green or black tea, Rooibos tea, other herbal teas, fruit-containing lemonades, isotonic beverages, soft drinks, nectars, fruit and vegetable juices, and fruit or vegetable juice preparations), instant beverages (e.g., instant cocoa beverages, instant tea beverages, and instant coffee beverages), meat products (e.g., ham, fresh or raw sausage preparations, and seasoned or marinated fresh meat or salted meat products), eggs or egg products (e.g., dried whole egg, egg white, and egg yolk), cereal products (e.g., breakfast cereals, muesli bars, and pre-cooked instant rice products), dairy products (e.g., whole fat or fat reduced or fat-free milk beverages, rice pudding, yoghurt, kefir, cream cheese, soft cheese, hard cheese, dried milk powder, whey, butter, buttermilk, and partly or wholly hydrolyzed products containing milk proteins), products from soy protein or other soy bean fractions (e.g., soy milk and products prepared thereof, beverages containing isolated or enzymatically treated soy protein, soy flour containing beverages, preparations containing soy lecithin, fermented products such as tofu or tempeh products prepared thereof and mixtures with fruit preparations and, optionally, flavoring substances), fruit preparations (e.g., jams, fruit ice cream, fruit sauces, and fruit fillings), vegetable preparations (e.g., ketchup, sauces, dried vegetables, deep-freeze vegetables, pre-cooked vegetables, and boiled vegetables), snack articles (e.g., baked or fried potato chips (crisps) or potato dough products and extrudates on the basis of maize or peanuts), products on the basis of fat and oil or emulsions thereof (e.g., mayonnaise, remoulade, and dressings), other ready-made meals and soups (e.g., dry soups, instant soups, and pre-cooked soups), seasonings (e.g., sprinkle-on seasonings), sweetener compositions (e.g., tablets, sachets, and other preparations for sweetening or whitening beverages or other food). The present compositions may also serve as semi-finished products for the production of other compositions intended for nutrition or pleasure.

The subject composition can further comprise one or more pharmaceutically acceptable carriers, and/or excipients, and can be formulated into preparations, for example, solid, semi-solid, liquid, or gaseous forms, such as tablets, capsules, powders, granules, ointments, solutions, suppositories, injections, inhalants, and aerosols.

The term "pharmaceutically acceptable" as used herein means compatible with the other ingredients of a pharmaceutical composition and not deleterious to the recipient thereof.

Carriers and/or excipients according the subject invention can include any and all solvents, diluents, buffers (such as, e.g., neutral buffered saline, phosphate buffered saline, or optionally Tris-HCl, acetate or phosphate buffers), oil-in-water or water-in-oil emulsions, aqueous compositions with or without inclusion of organic co-solvents suitable for, e.g., IV use, solubilizers (e.g., Polysorbate 65, Polysorbate 80), colloids, dispersion media, vehicles, fillers, chelating agents (e.g., EDTA or glutathione), amino acids (e.g., glycine), proteins, disintegrants, binders, lubricants, wetting agents, emulsifiers, sweeteners, colorants, flavorings, aromatizers, thickeners (e.g. carbomer, gelatin, or sodium alginate), coatings, preservatives (e.g., Thimerosal, benzyl alcohol, polyquaterium), antioxidants (e.g., ascorbic acid, sodium metabisulfite), tonicity controlling agents, absorption delaying agents, adjuvants, bulking agents (e.g., lactose, mannitol) and the like. The use of carriers and/or excipients in the field of drugs and supplements is well known. Except for any conventional media or agent that is incompatible with the target health-promoting substance or with the composition, carrier or excipient use in the subject compositions may be contemplated.

In one embodiment, the compositions of the subject invention can be made into aerosol formulations so that, for example, it can be nebulized or inhaled. Suitable pharmaceutical formulations for administration in the form of aerosols or sprays are, for example, powders, particles, solutions, suspensions or emulsions. Formulations for oral or nasal aerosol or inhalation administration may also be formulated with carriers, including, for example, saline, polyethylene glycol or glycols, DPPC, methylcellulose, or in mixture with powdered dispersing agents or fluorocarbons. Aerosol formulations can be placed into pressurized propellants, such as dichlorodifluoromethane, propane, nitrogen, fluorocarbons, and/or other solubilizing or dispersing agents known in the art. Illustratively, delivery may be by use of a single-use delivery device, a mist nebulizer, a breath-activated powder inhaler, an aerosol metered-dose inhaler (MDI), or any other of the numerous nebulizer delivery devices available in the art. Additionally, mist tents or direct administration through endotracheal tubes may also be used.

In one embodiment, the compositions of the subject invention can be formulated for administration via injection, for example, as a solution or suspension. The solution or suspension can comprise suitable non-toxic, parenterally-acceptable diluents or solvents, such as mannitol, 1,3-butanediol, water, Ringer's solution, or isotonic sodium chloride solution, or suitable dispersing or wetting and suspending agents, such as sterile, non-irritant, fixed oils, including synthetic mono- or diglycerides, and fatty acids, including oleic acid. One illustrative example of a carrier for intravenous use includes a mixture of 10% USP ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Water or saline solutions and aqueous dextrose and glycerol solutions may be preferably employed as carriers, particularly for injectable solutions. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

In one embodiment, the compositions of the subject invention can be formulated for administration via topical application onto the skin, for example, as topical compositions, which include rinse, spray, or drop, lotion, gel, ointment, cream, foam, powder, solid, sponge, tape, vapor, paste, tincture, or using a transdermal patch. Suitable formulations of topical applications can comprise in addition to any of the pharmaceutically active carriers, for example, emollients such as carnauba wax, cetyl alcohol, cetyl ester wax, emulsifying wax, hydrous lanolin, lanolin, lanolin alcohols, microcrystalline wax, paraffin, petrolatum, polyethylene glycol, stearic acid, stearyl alcohol, white beeswax, or yellow beeswax. Additionally, the compositions may contain humectants such as glycerin, propylene glycol, polyethylene glycol, sorbitol solution, and 1,2,6 hexanetriol or permeation enhancers such as ethanol, isopropyl alcohol, or oleic acid.

Methods of Using Compounds of the Subject Invention

In certain embodiments, compound cA (chrexanthomycin A) and five structurally-similar analogs (chrexanthomycin B (cB), chrexanthomycin C (cC), chrexanthomycin D (cD), chrexanthomycin E (cD), chrexanthomycin F (cF)) can be administered to a subject. In certain embodiments, compound cA, cB, cC, cD, cE, or cF can bind to DNA or RNA G4C2 G-quadruplex (G4), can have neuroprotective bioactivities on protecting neuronal cells from glutamate-induced excitotoxicity, and can be used as therapies for neurodegenerative diseases, such as, for example, AD, PD, ALS, HD, multiple sclerosis, epilepsy, stroke, alcohol withdrawal, PSP, PiD, CBD, or FTDP-17.

In certain embodiments, compound cA, cB, cC, cD, cE, or cF may not be cytotoxic on any type of eukaryotic cell, particularly on either neuronal or HEK293T cells. In certain embodiments, cA or cC can selectively protect cells from excitotoxicity caused cell death, particularly differentiated HT22 cells.

In certain embodiments, a tautomerization process can result in two forms cA, cB, cC, cD, cE, or cF: an open form and a cyclic form.

In certain embodiments, cA, cB, cC, cD, cE, or cF, preferably cA, cB, or cC can physically interact with G-quadruplex (G4), preferably a DNA $(G4C2)_4$ (SEQ ID NO: 5) G-quadruplex (G4). In certain embodiments, cA, cB, cC, cD, cE, or cF, preferably cA, can bind to RNA $(G4C2)_2$ (SEQ ID NO: 8) G4. In certain embodiments, cA, cB, cC, cD, cE, or cF, preferably cA, cB, cC or cF, can selectively bind to the RRM domain of RNA binding protein, hnRNP H. In certain embodiments, the RRM domain of hnRNP H can bind to RNA $(G4C2)_2$ (SEQ ID NO: 8) G4 and DNA $(G4C2)_4$ (SEQ ID NO: 5) G4, which can form a complex of cA, cB, cC, cD, cE, and/or cF, preferably cA, with hnRNP H, RNA $(G4C2)_2$ (SEQ ID NO: 8) G4 and DNA $(G4C2)_4$ (SEQ ID NO: 5) G4. In certain embodiments, cA, cB, cC, cD, cE, or cF, preferably cA, do not bind with other G4 structures, such as, for example DNA $(G4C2)_2$ (SEQ ID NO: 4) G4, human telomeric G4s, and chicken G4. In certain embodiments, cA, cB, cC, cD, cE, or cF, specifically cA and cC, can inhibit $(G4C2)_{29}$ (SEQ ID NO: 6)-caused cell death and can reduce G4C2 RNA foci numbers in $(G4C2)_{29}$ (SEQ ID NO: 6)-expressing cells, specifically Neuro2a cells. In certain embodiments, cA, cB, cC, cD, cE, or cF can rescue $(G4C2)_{29}$ (SEQ ID NO: 6)-caused eye degeneration in animals. In certain embodiments, cA, cB, cC, cD, cE, or cF can be used to treat C9orf72 ALS or FTD by blocking multiple pathological targets and improving neuron survival.

In addition, cA, cB, cC, cD, cE and cF can significantly inhibit aberrant Tau aggregation and/or decrease or eliminate tau fibril formation, tau oligomer formation, or tau protofibril formation.

In certain embodiments, the compounds of the subject invention, specifically cA, cB, cC, cD, cE or cF, can penetrate the blood brain barrier of a subject without hemolytic effects and can also rescue $(G4C2)_{29}$ (SEQ ID NO: 6) repeats-caused eye degeneration in animals. In certain embodiments, the compounds of the subject invention, particularly cA, cB, cC, cD, cE or cF, can contact neuronal cells after crossing the blood brain barrier.

MATERIALS AND METHODS

Bacterial Strains

The strain *Streptomyces chrestomyceticus* BCC 24770 was purchased from Thailand Bioresource Research Center, MRSA ATCC 43300. The strain *Streptomyces caelestis* Aw99c was isolated from the Red Sea coastal water side of fish market near Jeddah (21029.622N 39009.617E). The culture was isolated by BD Difco 212168 Actinomycete Isolation Agar.

Fermentation, Extraction, and Isolation

The strain *Streptomyces chrestomyceticus* BCC 24770 was cultured in two 125 ml Erlenmeyer flasks containing 50 ml of the GYM medium (4 g of yeast extract, 10 g of malt extract, and 4 g of D-glucose per liter of distilled water) and 20-30 glass beads (3 mm in diameter) at 30° C. and with an agitation of 180 rpm for three days. 1% of the seed broth was then transferred into ten Erlenmeyer flasks containing 1 L of the GYM media and around 100 glass beads for fermentation at 30° C. with an agitation of 180 rpm for 10 days. The strain *Streptomyces caelestis* Aw99c was cultured in 37×1.0 L volume of SPY media (10 g/L of starch, 2 g/L of peptone, 4 g/L of yeast extract and 20 g/L of sea salt) at 23° C. for 7 days. Each flask contained about 100 glass beads (3 mm in diameter). The spent fermentation culture was filtered with 8 layers of cheesecloth.

The bacterial culture broth was extracted with an equal volume of ethyl acetate three times to obtain the crude extract. The crude extract was separated by the reversed-phase C18 column chromatography and eluted with 20, 40, 60, 80, and 100% acetonitrile to obtain different fractions. Compounds were obtained in the 60% eluate monitored at a UV wavelength of 210 nm (Waters 2998 Photodiode Array Detector) and further purified by semi-preparative HPLC (Waters 2695 Separations Module; Milford, USA), using a Phenomenex Luna C18 column, 250×10 mm in size, and designed for a particle size of 5 m, eluted with an isocratic mobile phase at a flow rate of 3 ml/min (Solution A: acetonitrile with 0.5% trifluoroacetic acid (TFA); solution B: Milli-Q water with 0.5% TFA. Acetonitrile/water ratio was 30%). The eluate was monitored at a UV wavelength of 210 nm (Waters 2998 Photodiode Array Detector). Compounds were collected, freeze-dried by Labconco FreeZone 4.5 Liter Benchtop Freeze Dry System, and dissolved in dimethyl sulfoxide (DMSO) for further biological assessments.

Structural Elucidation

MS data were recorded from a Bruker ultrafleXtreme ultra-high-resolution TOF LC-MS system and a MALDI TOF/TOF Mass Spectrometer (Bruker Daltonics). Optical rotations were determined using a Jasco P-2000 Polarimeter. $^1H$ and $^{13}C$ NMR spectra were performed on 800 MHz and 200 MHz Varian spectrometers, respectively. All standard 2D NMR experimental spectra, including NOESY, HSQC, HMBC, and COSY were collected at 25° C. Circular dichroism (CD) spectra were measured by Chirascan Circular Dichroism Spectrometer.

Crystallization and X-Ray Crystallography

Crystallization of cA was achieved by solvent diffusion of an acetonitrile-methanol solution over several days. Single crystal X-ray data were collected on a Rigaku OD Supernova instrument (Cu-Ka radiation) at −173.15° C. A thin yellow plate (0.2×0.08×0.02 mm) was immersed in Paratone and mounted in a cryo-loop on a Rigaku-Oxford Diffraction Supernova diffractometer and diffraction data were collected at −173.15° C. The resulting monoclinic crystal structure refined successfully to a conventional R1=5.98% with residual electron density peak/hole of +0.26/−0.29 eÅ−3 and a Flack handedness parameter of 0.1 (3). This revealed the cA skeleton with a 4,5-dehydro-D-glucuronic acid moiety at one end, (sugar C2'=R, C3'=S) a central hydroquinone-xanthone unit and at the other end the compound showed a disordered arrangement between the open and cyclic form, representing isomers that are in solution equilibrium. A 50:50 disorder in the crystal is required due to the potential overlap of groups in neighboring molecular pairs. Hence an open form is in close contact with a cyclic form. The structural arrangement of the two disordered molecular fragments refines geometrically sensibly without the need for severe restraints. The cyclic form is an alpha-hydroxy-lactone, with R-stereochemical center. The open form, which is indicated in forming supramolecular association with the quadruplex has exocyclic carboxylic acid (—COOH) and acetonyl (—CH2-COMe) groups. The structure contains several water and methanol molecules, that are also partially disordered as a consequence of disorder in the main molecule.

Molecule Docking

Docking, energy filtering, clustering, and ranking of DNA $(G4C2)_4$ (SEQ ID NO: 5) G4-cA, DNA $(G4C2)_4$ (SEQ ID NO: 5) G4-cB, and DNA $(G4C2)_4$ (SEQ ID NO: 5) G4-cC were done by the Autodock4.2[61]. NMR structure of DNA $(G4C2)_4$ (SEQ ID NO: 5) G4 (PDB code: 2N2D) was obtained from the Protein Data Bank (PDB). The Lamarckian Genetic algorithm was applied, and a total of 150 separate dockings with a maximum number of 1.75×10$^6$ energy evaluations were performed. During the docking procedure, DNA structure was regarded as rigid, while ligand molecules were considered to be flexible. Finally, the conformation with the lowest binding free energy and the most cluster member was selected as the most probable binding conformation. PyMOL was used to analyze the potential presence of interacting bonds of the most favorable confirmation obtained from Autodock.

DNA/RNA G4 Sample Preparation

Single DNA/DNA strands were purchased from Integrated DNA Technologies (IDT) and Takara. Single-strand DNA/RNA sample at 100 μM was then annealed by heating up to 95° C. for 15 mins, and slowly cooled to room temperature in the annealing buffer (70 mM KCl, 20 mM potassium phosphate (pH 7.0)) for overnight. The final NMR samples contained 0.1 mM DNA or RNA in 70 mM KCl and 20 mM potassium phosphate buffer (pH 7.0).

One-Dimensional (1D) $^1$H-NMR Titration Experiments

The 1D $^1$H-NMR spectra were performed at 25° C. All compounds were dissolved in isotope-labeled $d_6$-DMSO (Sigma-Aldrich) at about 50 mM concentration, working as stock solutions. To avoid chemical shift changes of DNA/RNA G4 resulted from $d_6$-DMSO addition, 10 L $d_6$-DMSO was added into 500 μL of 0.1 mM DNA/RNA G4 solution in the NMR buffer (20 mM potassium phosphate buffer and 70 mM KCl, pH 7.0, 10% $D_2O$) and then 1D $^1$H-NMR spectrum was recorded as a reference. During NMR titration experiments of adding each compound into the DNA/RNA G4 solution, the maximal volume of 10 μL of each compound in $d_6$-DMSO solution was regarded as a final data point.

Expression and Purification of the RRM Domain of hnRNP H/F and Human Orc6

The coding sequence of the RRM domain of hnRNP H/F, or human Orc6 was inserted into the expression vector pET-28a(+) (Novagen). Protein was expressed in *Escherichia coli* BL21(DE3) at 37° C. for 5 hours. Cell lysates were subject to affinity purification with nickel-nitrilotriacetic acid resin (Qiagen) followed by cleavage of hexahistidine tag with Protease 3C enzyme. Products were further purified on a Superdex 75 column (GE Healthcare). For NMR studies, uniformly $^{15}$N labeled protein was expressed and purified as described above, except for cells grown in M9 medium containing 100% $^{15}$N enriched ammonium chloride (Cambridge Isotopes) and d-glucose.

NMR Titration of the RRM Domain of hnRNP H/F or hOrc6 with Compounds or DNA/RNA G4s Titration experiments were performed by recording a series of 2D $^{15}$N-HSQC spectra on uniformly $^{15}$N-labeled RRM domain (~0.1 mM) in the presence of different amounts of DNA/RNA or compounds at 25° C. Protein samples and stock solutions of DNA/RNA were all prepared in 20 mM potassium phosphate buffer and 70 mM KCl, pH 7.0, 10% $D_2O$. All compounds were dissolved in isotope-labeled $d_6$-DMSO (Sigma-Aldrich) at about 50 mM concentration, working as stock solutions. To avoid chemical shift changes of protein samples resulted from $d_6$-DMSO addition, 10 μL $d_6$-DMSO was added into 500 μL of 0.1 mM protein solution in the NMR buffer (20 mM potassium phosphate buffer and 70 mM KCl, pH 7.0, 10% $D_2O$) and then the 2D HSQC was recorded as a reference.

Parallel Artificial Membrane Permeability Assay

500 μL of 500 μM test compound and 200 μM Equilibrium Standards for each test compound were prepared. 5 μL DMSO plus 245 μL PBS served as blank control. Firstly, 300 μL PBS was added to each well in the acceptor plate. With the donor plate in its tray, 5 μL 4% Lecithin in Dodecane was added directly to the well membranes of the donor plate. 200 μL of each 500 μM test compound was added to duplicate wells of the donor plate. The donor plate was carefully placed into the acceptor plate wells and incubated at 37° C. for 18 hours. Then the liquid in acceptor plate wells was collected as Acceptor Solution for analysis. Absorbance spectrum from 200 nm to 500 nm in 10 nm intervals was read to determine the peak absorbance of test compounds and blank control.

Hemolysis Assays

Hemolytic activity was determined with 2% fresh red blood cells from a healthy rabbit. Blood cells were obtained and washed with PBS buffer four to five times and centrifuged at 1500 rpm for 10 mins until the upper phase became clear. Compounds were diluted with PBS to final concentrations of 1000, 500, 250 μg/mL, added to the same volume of 2% red blood cells and incubated at 37° C. for 1 hour. Samples were centrifuged at 10,000 rpm for 5 mins, and supernatants were added into 96-well plates and measured at 570 nm with a Thermo Scientific Multiskan FC multiplate photometer (Thermo Scientific™, USA). An aliquot of 10% Triton X-100 was used as the positive control, and 1% DMSO dissolved in PBS was used as the negative control.

Cell Culture

HEK293T, Neuro2a, and HT22 cells (Sigma-Aldrich, SCC129) were cultured in DMEM (Thermo Fisher Scientific, 11965092) with 10% fetal bovine serum (FBS; Thermo Fisher Scientific, 26140079) plus penicillin-streptomycin (Thermo Fisher Scientific, 15140163; 10,000 U/mL) at 37° C. in a humidified incubator with an atmosphere of 5% $CO_2$ and 95% air.

MTT Assay

Cytotoxicity of compounds was tested by MTT assay. Cells were grown in DMEM (Gibco) with 10% FBS and 1% penicillin-streptomycin at 37° C. with 5% $CO_2$. In total, $5\times10^3$ cells were seeded in each well of 96-well plates and cultured for 24 hours. Then cells were treated with different concentrations of compounds dissolved in DMSO for another 24 hours. After incubating with 20 μl of MTT (5 mg/mL) for each well at 37° C. for another four hours, 100 μl of DMSO was added to dissolve formazan. Absorbance was measured using a Multiskan™ FC microplate photometer at 570 nm. $IC_{50}$ data were analyzed with GraphPad Prism software.

Transfection

DNA constructs were transfected to neuronal Neuro2a cell lines using Lipofectamine 2000 (Thermo Fisher Scientific, 11668019). 4 to 6 hours after transfection, fresh culture medium was used to replace the transfection medium, and cells were incubated for another 48 hours to allow recovery and construct expression.

RNA Fluorescent In Situ Hybridisation and Immunocytochemistry

Neuro2a cells planted on coverslips were transfected with pHR-Tre3G-29xGGGGCC-12xMS2 plasmid (#99149), incubated for 2-3 days and then fixed with 4% paraformaldehyde for 15 min at room temperature. Cells were permeabilised with 0.1% TritonX-100 in PBS for 10 min before hybridisation. Target probe (GGCCCCGGCCCCGGCCCCGGCCCC) (SEQ ID NO: 1) with a 5'-Cy3 and control probe (CAGGCAGGCAGGCAGGCAGG) (SEQ ID NO: 2) with a 5'-Cy5 were added to the hybridisation solution (0.9M NaCl, 0.02M Tris-HCl, 0.01% SDS, 20% formamide). Cells were then incubated in the mixed solution at 46° C. for 3 h. Cells were washed three times in washing solution (0.02M Tris-HCl, 0.001% SDS, 5 mM EDTA) at 48° C., 15 min each time. Then, cells were stained with primary antibodies (Anti-DNA G-quadruplex (G4) antibody (Cat. No. MABE1126) or Anti-hnRNP H antibody (ab10374)) at 1:500 dilution and incubated at 4° C. overnight. In the next day, cells were washed three times with PBS (10 min each time), and then incubated with secondary antibodies (Alexa 488 anti-mouse for G4 or Alex 488 anti-rabbit for hnRNP H) at 1:500 dilution for 1 h at room temperature. Superfluous secondary antibodies were washed away with PBS for three times (10 min each time). Then cells were incubated with DAPI at 1:5000 dilution for 5 mins and washed with PBS once. Finally, cells on slides were air-dried, mounted in Hydromount medium and analysed by confocal microscopy (Leica, SP8).

Drosophila Feeding

A fly line expressing 29 GGGGCC repeats (29R) (SEQ ID NO: 6), under the GMR-GAL4 promoter (GMR-GAL4-(G4C2)$_{29}$ (SEQ ID NO: 6)), was used. Both GMR-GAL4-(G4C2)$_{29}$ (SEQ ID NO: 6) and WT flies were raised at room temperature (25° C.) on a cornmeal medium supplemented with dry yeast. DMSO was served as vehicle control, compounds cA and cC were added in a working concentration of 100 μM (62 μg/mL and 63.8 μg/mL), respectively. Parent flies for cross were set in solid food containing testing compound, and F1 larvae were thus fed with food continuously until eclosion. After eclosion, F1 flies were transferred to normal food containers without compounds.

External Eye Assay

Eye images of GMR-GAL4-(G4C2)$_{29}$ (SEQ ID NO: 6) or WT adult flies at day 7 after eclosion were captured using a CCD camera on an Olympus stereomicroscope. Eye morphologies of flies in different treatment groups were compared to evaluate the retina degeneration level. The affected eye area and total eye area were measured to calculate the degeneration ratio by ImageJ.

Glutamate-Induced Excitotoxicity Cell Model

Cultured HT22 cells were differentiated by applying 10 μM retinoic acid (Sigma-Aldrich, R2625-50MG) and 500 μM cAMP (Sigma-Aldrich, A6885) in DEME medium supplied with 0.5% FBS (differentiation medium) and incubated 48 hours before adding other treatments. 5 mM L-glutamate acid was applied to the original differentiation medium for further 24-hours incubation. Cell viability was measured by MTT assay described above.

Thioflavin T (ThT) Fluorescent Tau Accumulation Assay

Tau-R3 protein was synthesized and purchased from ChinaPeptides Co., Ltd. ThT (ab120751, 1 mM) solution was freshly prepared in 50 mM Tris-HCl buffer (pH 7.4) and passed through a 0.45 μm pore size filter to remove insoluble particles before use. Tau-R3 (20 μM) was incubated with 20 μM ThT and 10 μM heparin in the presence or absence of cA, cB and cC. Samples in 200 μL were added to 96-well plates and incubated at 37° C. for 24-48 hours. ThT fluorescence intensity was recorded using a microplate reader with 440/480 nm excitation/emission filters at different time points. Non-linear regression analysis was performed to fit the boltzmann sigmoidal.

TEM Imaging

Samples from ThT fluorescence experiments were directly applied to a 300-mesh carbon coating copper grid. 20 μL of aggregate samples were dispensed onto a sheet of parafilm, and a copper grid was placed onto the sample drop for 5 mins. The copper grid with samples was moved to water drop for 5 mins-washing, and then stained with 2% uranyl acetate for 5 mins. Images were captured using a transmission electron microscope (Thermo Scientific Talos L120C) at a magnification of 13500× and an acceleration voltage of 120 kV.

Statistical Analysis

All data were obtained from at least three independent preparations. Quantifications were performed in a blinded manner. Statistical analysis was performed with GraphPad Prism 6. Differences between groups were analyzed using the unpaired t-test. A p value≤0.05 was considered significant.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1-Preliminary Screening and Neuroprotective Cell Modeling

Fractions F8, F9, F10, F11, and F13 were isolated from EtOAc extracted crude extract of bacteria strain *Streptomy-* ces chrestomyceticus BCC 24770 (FIG. 1A) for fermentation of 10 days in the GYM medium at 30° C. These fractions were selected based on their UV absorbance pattern and retention time on HPLC (FIG. 1B), which were predicted with novel chemical structures.

Figure 1I:
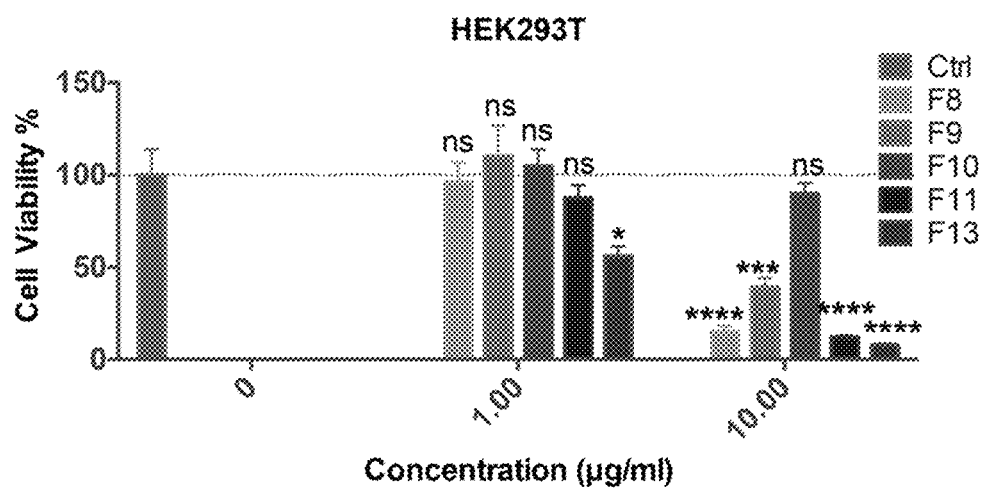

Preliminary cytotoxicity tests of F8, F9, F10, F11, and F13 were performed on the neuronal cell line-Neuro2a cells and HEK293T cells. Except for F10, all the other fractions showed cytotoxicity at 1 µg/ml in Neuro2A cells, and F13 even showed cytotoxicity at 0.1 µg/ml. In contrast, there was no cytotoxicity of F10 even at a high concentration of 10 µg/ml (FIGS. 1C-1H). Similarly, F8, F9, F11, and F13 showed significant cytotoxicity at 10 µg/ml in the HEK293T cells, with which the cell viability was below 50% while with F10 treatment the viability of cells was close to 100% (FIG. 1I). Therefore, F10 was chosen for further investigation. Meanwhile, F10 signal were also detected in the EtOAc extracted crude extract of bacteria strain *Streptomyces caelestis* Aw99c with the fermentation of 7 days in the SPY medium at 23° C.

Figure 1J:
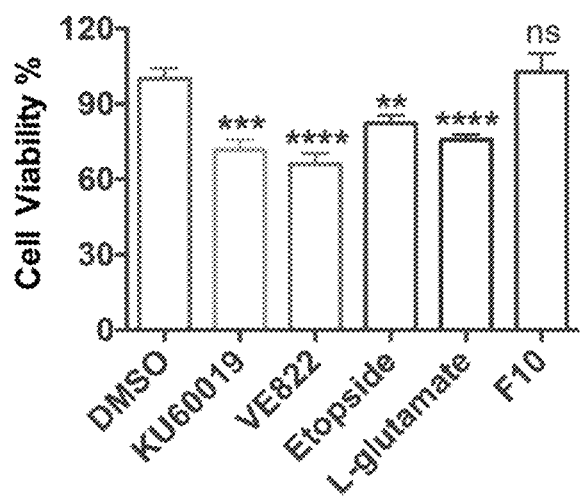
Figure 1K:
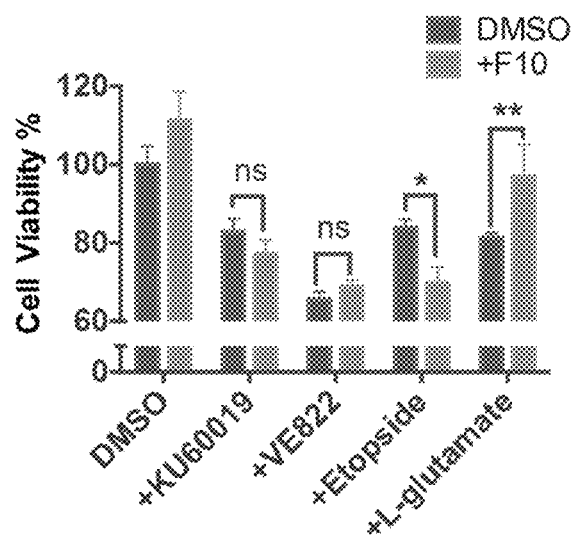

To simulate primary neurons better, the neuronal cell lines (HT22 and Neuro2a) used in the experiment were differentiated at least for 3 days before adding compounds. After differentiation, several different drugs (1 µM KU60019, 0.5 µM VE822, 1 µM Etoposide or 5 mM L-glutamate) were applied to the culture medium respectively to induce neuronal cell death. A 20%-40% cell death was induced by these drugs treatments (FIGS. 1J-1K). Intriguingly, F10 rescued the cell viability from 80% to almost 100%, almost close to the control group in the L-glutamate induced neuronal cell death model other than the other models (KU60019, VE822, Etoposide) (FIG. 1K), indicating F10 might protect neuronal cells from excitotoxicity-induced cell death by L-glutamate.

Example 2—The Purification of Compound Chrexanthomycin A (cA) and its Analogs

A pure fraction of F10 was enriched by semi-preparative HPLC (Flow rate: 3 mL min$^{-1}$, Solution A: acetonitrile with 0.5% trifluoroacetic acid (TFA); solution B: Milli-Q water with 0.5% TFA. Acetonitrile concentration increased from 25% to 45% in 70 min. Retention time: 38.5 minutes), and we named this compound chrexanthomycin A (cA). cA was obtained as a yellow powder after freeze-drying the product from HPLC semi-preparation and its molecular weight was confirmed by High-resolution Mass Spectrometer as 621.1235 [M+H]$^+$, calcd for $C_{31}H_{25}O_{14}$. Its specific rotation was −49.8 using methanol as solvent at room temperature. UV (MeOH) $\lambda_{max}$ nm 224, 243, 271, 401. Similarly, cB, and cC were also obtained as yellow powder after freeze-drying the product from HPLC semi-preparation. The molecular weight of compounds cB and cC were confirmed using High-resolution Mass Spectrometer as 635.1387 [M+H]$^+$, calcd for $C_{32}H_{27}O_{14}$; 639.1332 [M+H]$^+$, calcd for $C_{31}H_{27}O_{15}$. Their specific rotations were −27.3, −25.3. respectively. The UV (MeOH) $\lambda_{max}$ nm 222, 248, 270, 389 for cB, and the UV (MeOH) $\lambda_{max}$ nm 224, 271, 290, 401 for cC.

A pure fraction of chrexanthomycin D (cD) and chrexanthomycin E (cE) were collected together with cC during semi-preparation since their similar UV pattern as cC (Flow rate: 3 mL min$^{-1}$, Solution A: acetonitrile with 0.5% trifluoroacetic acid (TFA); solution B: Milli-Q water with 0.5% TFA. Acetonitrile concentration was isocratic at 40%. Retention time: 21.6 minutes for cD; 29.0 minutes for cE). cD and cE were obtained as yellow powders after freeze-drying the product from HPLC semi-preparation. A high-resolution Mass Spectrometer confirmed their molecular weights of compounds cD: 653.1784 [M+H]$^+$, calcd for $C_{32}H_{29}O_{15}$; cE: 667.1959 [M+H]$^+$, calcd for $C_{33}H_{31}O_{15}$. Compared to cC, their molecular differences of 14 and 28 indicate they were analogs of cC, UV (MeOH) $\lambda_{max}$ 222, 273, 330, 401 nm.

cF is the isomer of cA with the same molecular weight, but it has a different UV absorption; A pure fraction of chrexanthomycin F (cF) was enriched by semi-preparative HPLC (Flow rate: 3 mL min$^{-1}$, Solution A: acetonitrile with 0.5% trifluoroacetic acid (TFA); solution B: Milli-Q water with 0.5% TFA. Acetonitrile concentration was isocratic at 30%; Retention time: 40.9 minutes). cF was obtained as a yellow powder after freeze-drying the product from HPLC semi-preparation. A high-resolution Mass Spectrometer confirmed the molecular weight of this compound to be 621.1232 [M+H]$^+$, calcd for $C_{31}H_{25}O_{14}$. UV (MeOH) $\lambda_{max}$ 237, 270, 325, 410 nm.

Example 3—The Structure Elucidation of cA and its Analogs

Figure 2A:
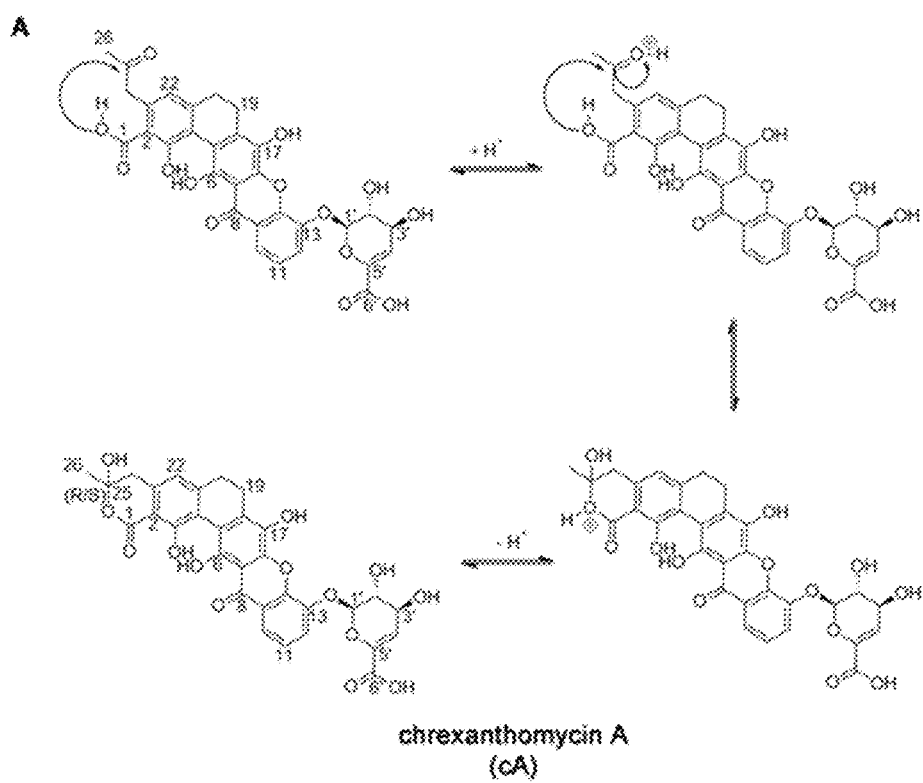
FIGS. 2A-2F Chemical structures of cA and its analogs.

For the structure elucidation of cA: three aromatic protons $H_6$ ($\delta H=7.97$, 1H, dd, J=8.0, 1.5 Hz), $H_8$ ($\delta H=7.79$, 1H, dd, J=8.0, 1.5 Hz), $H_7$ ($\delta H=7.38$, 1H, t, J=8.0 Hz), were observed to have COSY correlations, as well as the HMBC correlations from $H_{12}$ to $C_4$ ($\delta C=182.9$) and $C_{10}$ ($\delta C=148.4$), $H_7$ to $C_5$ ($\delta C=122.7$) and $C_9$ ($\delta C=146.4$), and $H_8$ ($\delta H=7.79$) to $C_6$ and $C_{10}$, indicates the presence of an aromatic ring connected with hydroxyls at $C_9$ and $C_{10}$, and a ketone at $C_5$. The sugar moiety can also be determined through COSY and HMBC correlations. According to COSY correlations, $H_1'$ ($\delta H=5.82$, 1H, d, J=5.5 Hz), $H_2'$ ($\delta H=4.16$, 1H, dd, J=5.5, 4.7 Hz), $H_3'$($\delta H=4.34$, 1H, dd, J=4.7, 3.6 Hz), and $H_4'$ ($\delta H=6.23$, 1H, d, J=3.6 Hz) strung together, together with the HMBC correlations from $H_1'$ to $C_5'$ ($\delta C=142.2$), $H_3'$ to $C_5'$ and $H_4'$ to $C_6'$($\delta C=165.1$), we can confirm this is a 4',5'-anhydroglucuronic acid moiety; Furthermore, the HMBC correlation from $H_1'$ to $C_9$ linked these two parts together through an O-glycosidic bond. The fragment's molecular weight we elucidated is around 400, far away from the actual results confirmed by HRMS and MALDI. Therefore, we assume there is a loss of signals when doing NMR tests. But the results have not improved with the change of solvents, relaxation time, and test temperature. With the help of crystallization, shiny yellow plates were observed in the bottom of the vessels using the vapor diffusion method. The single-crystal particle was picked to do X-ray diffraction for X-ray crystallography successfully. The XRD data clearly indicated the backbone of the compound. Intriguingly, two tautomeric structures with the same pentacyclic xanthone core and attached with an unusual 4',5'-anhydroglucuronic acid moiety were observed. Considering they share the same molecular weight, in addition to one interesting phenomenon was observed when using methanol-$d_4$ to do NMR tests that several proton signals in the high field region were broadened at room temperature while they became sharp when the temperature raised to 45° C., leading to the conclusion of tautomerization. And we proposed that cA structure with two forms, an open-ring structure 6-(2-oxopropyl) benzoic acid and a closed-ring cyclic hemiketal through the hydrogen transfer mechanism (FIG. 2A). Due to the lack of selectivity in the formation of the closed-ring structure, there should be two configurations of the cyclic hemiketal's chiral center. Consistently, our experimental XRD data showed both open-ring form and the cyclic form of the compound cA (FIG. 2E) exist in dynamic equilibrium.

Figure 2B:
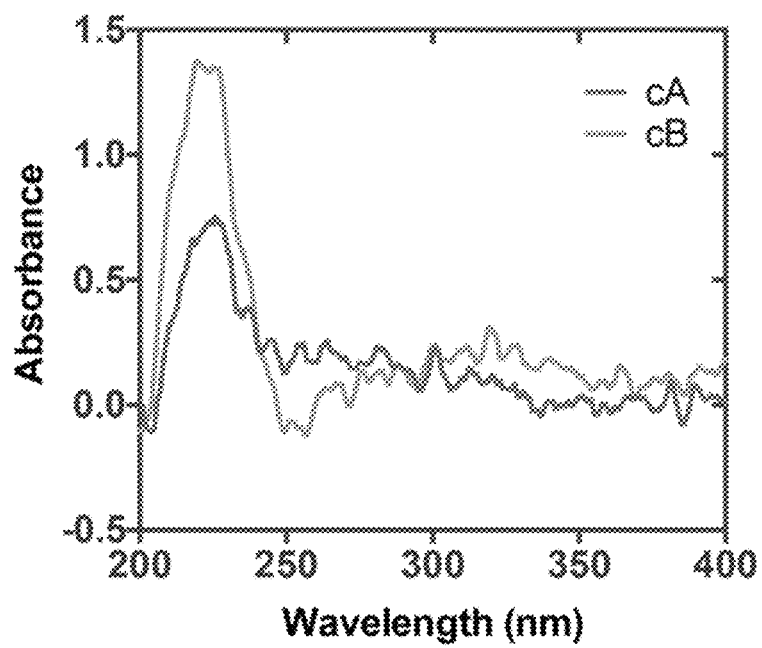
Figure 2C:
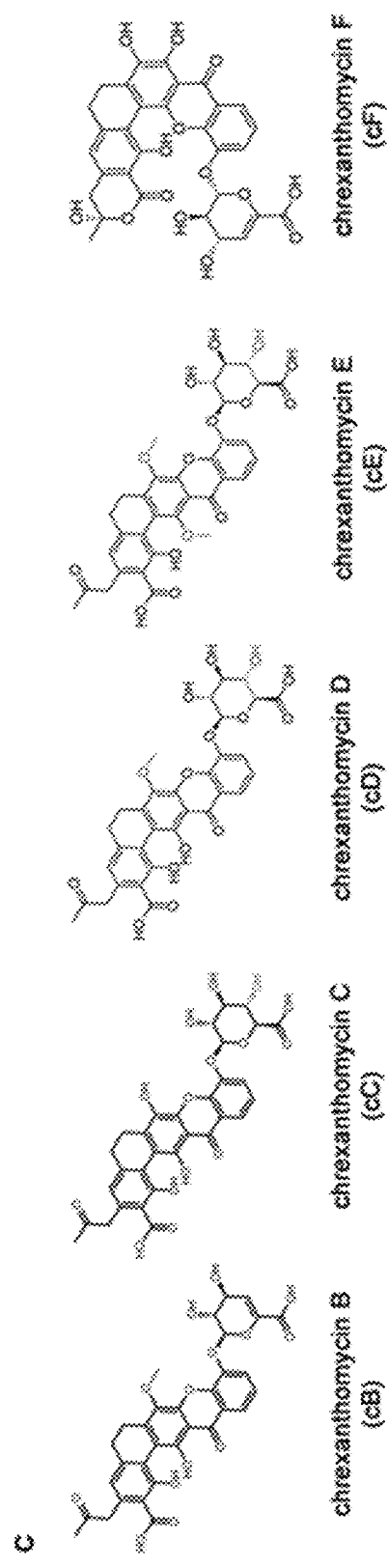
Figure 2D:
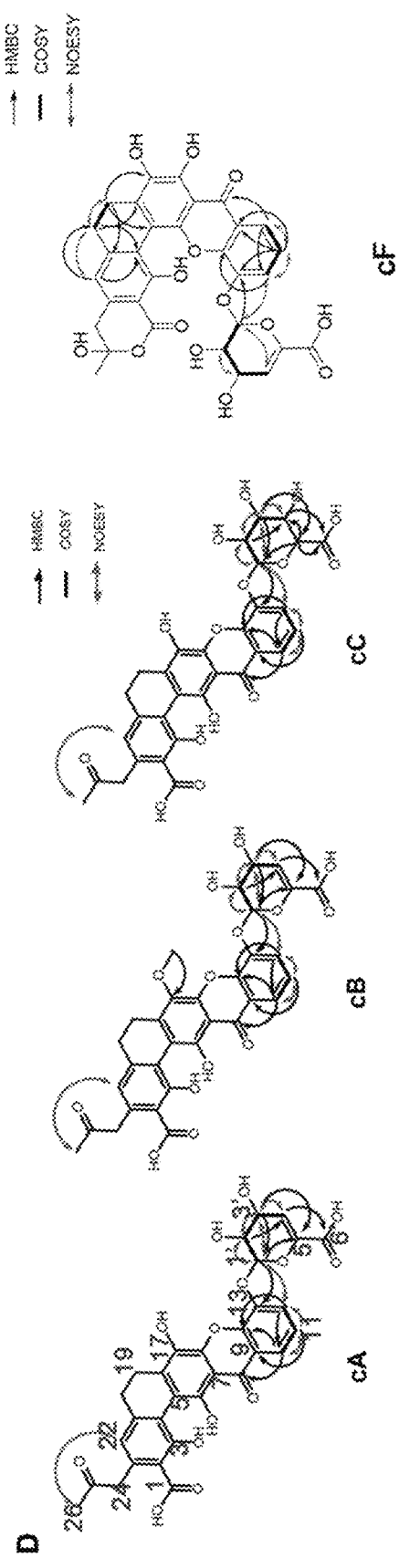
Figure 2E:
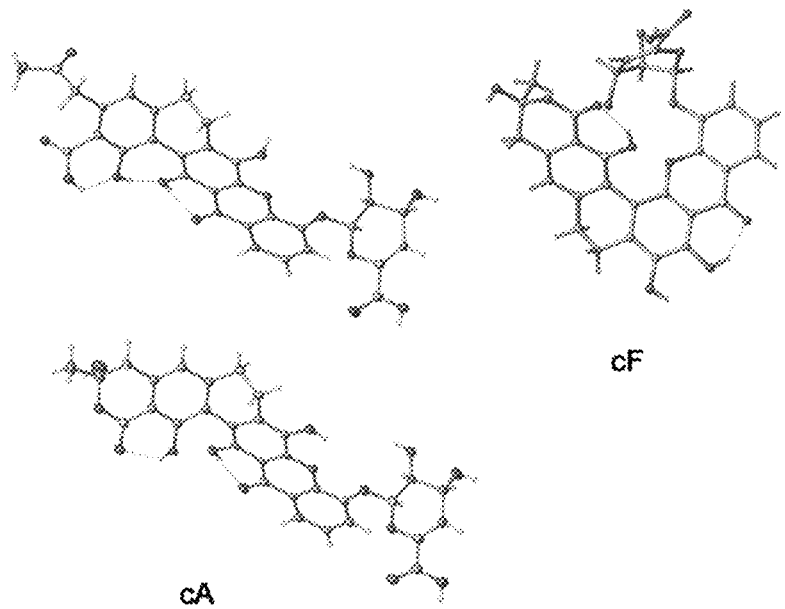

Once the structure of cA is confirmed, the structures of cB and cC were elucidated by comparing their NMR data with those of cA. Since the UV spectrum of cB is identical to that of cA, which indicates they share the same chromophore and backbone, and the difference of their molecular weight, 14, indicates it is analog of cA. Combining with the NMR spectra analysis and the CD spectrum comparison with cA (FIG. 2B), one more methoxyl group was observed, $\delta H=3.96$, 3H, s, with carbon chemical shift $\delta C=61.5$, and HMBC correlation between the methoxyl and carbon with chemical shift $\delta C=135.6$ indicates that $C_{13}$ was etherified. Furthermore, despite the disorders in the crystal structure of cB, we still determine the position of the methoxyl group unequivocally. As for cC, due to its molecular weight is 18 more than that of cA, and slight differences in UV pattern suggest the change of chromophore, by analyzing the NMR spectra, the anomeric carbon signal at $C_1'(\delta_C=104.5, \delta_H=5.16)$ and the presence of several oxymethine protons confirmed the presence of an O-glycoside in this structure. The COSY and HMBC correlations were observed between $\delta H_{2'\ 3.51}$ ppm $(\delta C_2'=73.8)$, $\delta H_{3'}$ 3.33 ppm $(\delta C_3'=75.8)$, $\delta H_{4'\ 3.45}$ ppm $(\delta C_4'=71.5)$, $\delta H_{5'\ 3.45}$ ppm $(\delta C_5'=75.5)$, and the HMBC correlations between $H_4'$, $H_5'$ and carboxylic acid carbon signal $C_6'(\delta C=170.0)$, and $H_5'$ to $C_1'$ and $C_3'$ established that this sugar moiety was a glucuronic acid, and comparing the NMR spectra with known structure contains the glucuronic acid, the stereochemistry of cC can also be confirmed. cD and cE were collected behind when preparing cC since their similar UV pattern as cC and molecular differences of 14 and 28 indicate they were analogs of cC. Both the glucuronic acid and methoxyl group was observed. As for cE, the difference compared with cD was the loss of a low field phenolic hydroxyl group, according to the biosynthesis pathway, which indicates another methoxyl substitution in the $C_6$ position. As for cF, single crystals were grown using methanol as the only solvent; a tiny yellow rod was observed in the bottom of the glass tubes after three days at room temperature, using the vapor diffusion method; The XRD data has good quality hence the stereochemistry is confirmed, and its backbone is clearly revealed, except the formation direction of the pentacyclic xanthone rings, cF also attached with an unusual 4',5'-anhydroglucuronic acid moiety (FIG. 2E, right panel).

Figure 2F:
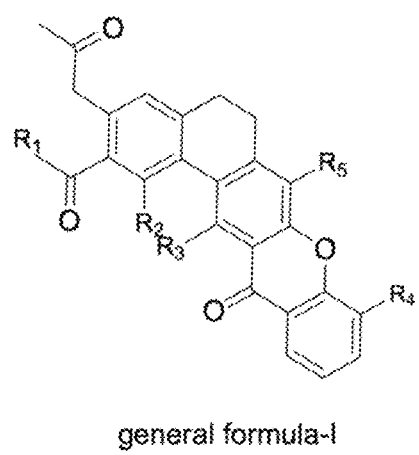
Figure 2F:
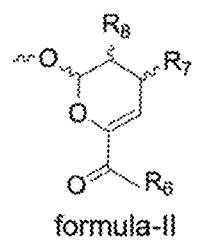
Figure 2F:
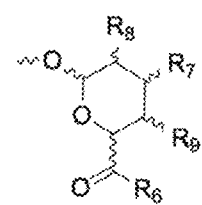

In summary, the planar structures of cA, cB, cC, cD, cE and cF (FIG. 2C) were established through a combination of HRMS, 1D, 2D NMR spectra, including $^1$H, $^{13}$C, COSY, HSQC, HMBC, and NOESY as well as single crystal crystallography. For NMR spectra, both DMSO-$d_6$ and methanol-$d_4$ were used as the solvent for the NMR tests. The key 2D NMR correlations ($^1$H,$^1$H-COSY, HMBC, NOESY) are shown in FIG. 2D. Thus, the general formula of the compound series was shown in FIG. 2F. $R_{1-9}$ represent different substituent groups. R1, $R_2$, $R_6$, $R_7$, $R_8$, and $R_9$ could be hydroxyl group. $R_3$ and $R_5$ could be either hydroxyl group, methoxyl group or ethoxyl group. $R_4$ could be either formula-II or formula-III.

Example 4—Compounds cA, cB, cC, and cF Selectively Bind to DNA (G4C2)$_4$ (SEQ ID NO: 5) G4

Being motivated by the interest in C9orf72 related ALS/FTD disease, we were seeking potential small molecules targeting C9orf72 G4C2 HRE. By in silico analysis, cA, cB and cC were all predicted to interact with DNA (G4C2)$_4$ (SEQ ID NO: 5) G4 (FIG. 3A), the secondary structure formed by the C9orf72 HRE DNA. The docking model with the lowest energy suggested that the compound cA, cB and cC perfectly fit into the wide groove between two strands of the G4 (FIG. 3B). Three hydrogen bonds were predicted to form between the G16(a), G8(b), G14(c) with the hydroxyl radical groups of cA, cB and cC (FIG. 4A).

We next confirmed the binding of cA and DNA (G4C2)$_4$ (SEQ ID NO: 5) G4 by NMR titration experiments. According to the 1D $^1$H-NMR spectra titrated with a different concentration ratio of G4 with cA (FIG. 3C) from 1:1 (light brown) to 1:10 (pink), apparent chemical shift changes in the peaks of G2/G10, G1/G14, G22, and G13 were observed, indicating a binding between cA and the DNA (G4C2)$_4$ (SEQ ID NO: 5) G4 structure. Similarly, cB, cC and cF were also proved to bind to DNA (G4C2)$_4$ (SEQ ID NO: 5) G4 by NMR titration (FIG. 3C).

Example 5—Compound cA Binds to RNA (G4C2)$_2$ (SEQ ID NO: 8) G4 and RRM Domains of hnRNP H In addition to C9orf72 HRE DNA, the C9orf72 HRE RNA was also found to form a noncanonical secondary structure, G-quadruplex (G4) (FIG. 3D), which might disrupt normal transcription, thus leading to the accumulation of abortive RNA transcripts and the loss of full-length RNA transcripts[34,35] A similar NMR titration experiment of RNA (G4C2)$_2$ (SEQ ID NO: 8) G4 and cA was performed. Chemical shift changes were observed in the 1D $^1$H-NMR spectrum with the ratio of 1:3 (green), 1:5 (blue) and 1:10 (pink) for RNA (G4C2)$_2$ (SEQ ID NO: 8) G4 and cA compared to the RNA (G4C2)$_2$ (SEQ ID NO: 8) G4 only (black) and DMSO control (brown) (FIG. 3E).

Notably, it was reported that the expanded RNA G4C2 repeats could be transcribed bidirectionally and form RNA foci, which is one of the primary mechanisms for the pathogenesis of C9orf72-associated ALS/FTD. In this scenario, specific RNA-binding proteins (RBPs), like hnRNP H, are recruited by the RNA foci, resulting in RNA processing impairment and further cytotoxicity to the central nervous system[30,36,37]. Therefore, we tested the binding possibility of cA with the RRM domain of hnRNP H by NMR titration. According to the overlapped $^{15}$N-$^1$H HSQC spectra of RRM1/2 of hnRNP H (black) and RNA (G4C2)$_2$ (SEQ ID NO: 8) G4 (red), it showed that the RRM domain of hnRNP H bound to RNA (G4C2)$_2$ (SEQ ID NO: 8) G4 (FIG. 4B) while cA (red/green) also bound to the RRM domain of hnRNP H (blue), occupying its binding sites to RNA (G4C2)$_2$ (SEQ ID NO: 8) G4 (FIGS. 3E-3I). Intriguingly, the DNA (G4C2)$_4$ (SEQ ID NO: 5) G4 was also shown a potent binding affinity to the RRM domain of hnRNP H (FIG. 4C). Therefore, it is possible that cA bound to a complex formed by the DNA (G4C2)$_4$ (SEQ ID NO: 5) G4, RNA (G4C2)$_2$ (SEQ ID NO: 8) G4 and hnRNP H. In contrast, cB and cF showed much weaker bindings to the RRM domain of hnRNP H while the binding of cC to the RRM domain of hnRNP H seemed to be a little bit stronger than cA (FIGS. 3E-3I).

Figure 5E:
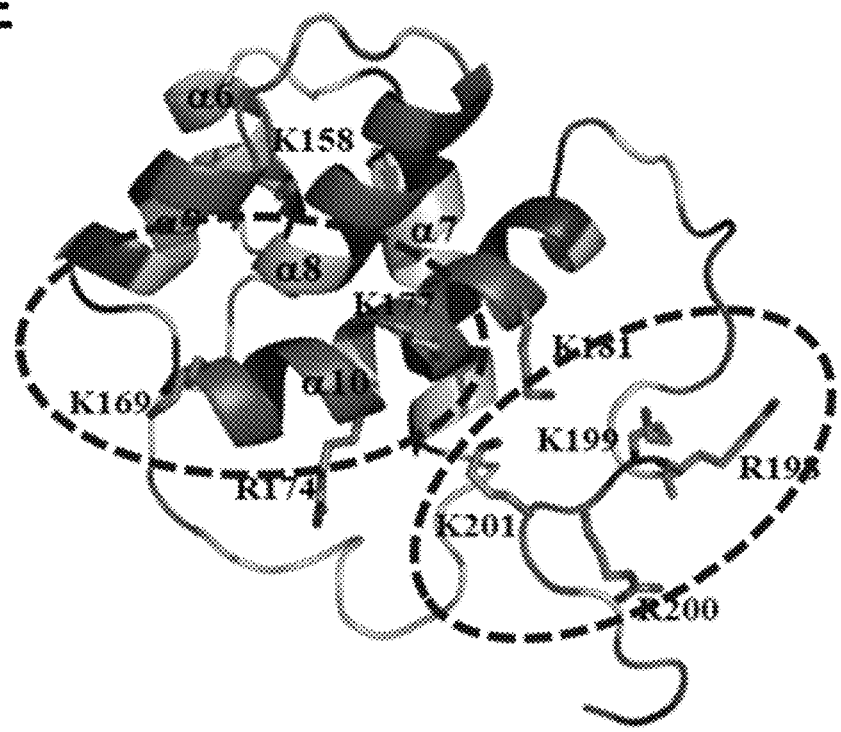

Example 6—Compound cA Binds to hnRNP F and Orc6 hnRNP F is another RNA binding protein, which could be recruited during RNA foci formation. Notably, we demonstrated that the RRM domain of hnRNP F showed significant binding affinity both to the DNA (G4C2)$_4$ (SEQ ID NO: 5) G4 and compound cA (FIG. 5A, FIG. 5B). Also, cA almost blocked all the binding sites of hnRNP F RRM domain for DNA (G4C2)$_4$ (SEQ ID NO: 5) G4 (FIG. 5C). In addition, we proved that cA bound to human ORC6, a subunit of the origin recognition complex (ORC) by NMR titration experiments (FIG. 5D). The binding sites on ORC6 are as shown in FIG. 5E, indicating the cA can block the binding of ORC to DNA replication origin thus inhibiting DNA replication.

Example 7—Compound cA does not Bind to Other G4 Structures

In the previous study, G4 folded by the C9orf72 HRE DNA and RNA was proved to show structural polymorphisms, which highly contributed to the pathogenesis of C9orf72 ALS/FTD. In addition to the four-repeat G4C2 DNA G4, there are parallel and hybrid G4 conformations formed simultaneously by the two-repeat G4C2 DNA[38,39]. To test whether cA binds to G4s formed by C9orf72 G4C2 HRE DNA with different length, the NMR titration of DNA (G4C2)$_2$ (SEQ ID NO: 4) G4 (FIG. 6A) with cA at a ratio of 1:1, 1:5, and 1:10 were performed. The 1D $^1$H NMR spectra showed that neither with 1:1 (light brown), 1:5 (blue) nor 1:10 (pink) titration of cA made significant chemical shift changes compared to the DNA (G4C2)$_2$ (SEQ ID NO: 4) G4 only spectrum (black) (FIG. 6B). In addition to the GGGGCC sequence, other G-rich DNA or RNA strands are able to form polymorphic G4s, too. For example, the human telomeric variant, htel21_T18 (d[(GGGTTA)$_2$-GGGTTTGGG]) (SEQ ID NO: 3), is chair-type (FIG. 6C); while the conformation of the human telomeric quadruplex d[TA(GGGTTA)$_3$GGG] (SEQ ID NO: 7), named htel23, is hybrid-type[40,41] (FIG. 6D). To investigate the binding preference of cA, NMR titration of cA with htel21_T18 and htel23_hybird was performed, respectively. The 1D $^1$H NMR spectra showed that there were no obvious chemical shift changes of the htel21_T18 and of that with cA at 1:10 titration (FIG. 6E). Similarly, the 1D $^1$H NMR spectra of the htel23_hybrid with cA at 1:10 titration showed no obvious chemical shift changes, either (FIG. 6F). As another control, the DNA G-quadruplex formed by chicken DNA replication origin (FIG. 6G) did not show binding to cA at a titration of 1:3 as well (FIG. 6H). To sum up, compound cA showed binding preference to specific DNA/RNA G4C2 G4 structures, indicating a high selectivity.

DB1246 (FIG. 7A), a small molecule, was identified to be able to bind and stabilize RNA (G4C2)$_4$ (SEQ ID NO: 5) G4 by other researchers[42]. As a nice control, we would like to know whether DB1246 directly binds to these G4 structures. Surprisingly, we found that DB1246 strongly bound to not only DNA (G4C2)$_4$ (SEQ ID NO: 5) G4 (FIG. 7B) and RNA (G4C2)$_2$ (SEQ ID NO: 8) G4 (FIG. 7C), but also DNA (G4C2)$_2$ (SEQ ID NO: 4) G4 (FIG. 7D) and human telomeric htel21_T18 G4 (FIG. 7E), implying that DB1246 is a common ligand for G4s. Taken together, these findings suggested a better selectivity and binding specificity of cA, as a possible drug candidate worth of further study.

Example 8—Compounds cA and Cc Rescue G4C2 HRE Relative Pathologies Both In Vitro and In Vivo Considering the significance of compounds binding to G4C2 HRE G4 (FIGS. 3A-3D), compounds cA, cB and cC can work in the same way binding to G4C2 HRE DNA in the cells, reducing the G4C2 HRE caused cell death. To test, a plasmid of DNA (G4C2)$_{29}$ (SEQ ID NO: 6) repeats was transfected into Neuro2a cells to establish a C9orf72 ALS/FTD cell model, and significant cell death (>50%) was observed with the (G4C2)$_{29}$ (SEQ ID NO: 6) repeats overexpression (FIGS. 8A-8B). Intriguingly, the application of both cA and cC at a concentration of 1 µg/ml partially increased the cell viability, while cB (1 µg/ml) made it worse (FIG. 8B).

Due to the binding of cA to RNA (G4C2)$_2$ (SEQ ID NO: 8) G4 and RNA binding protein, hnRNP H, which co-localizes with most of the G4C2 RNA foci detected in C9orf72 mutant ALS and FTD brain tissues[37], we next determine whether compounds cA and cC could affect the G4C2 RNA foci formation, which is one the key pathologies in the C9orf72 ALS. Firstly, we confirmed that RNA foci were specifically observed in the (G4C2)$_{29}$ (SEQ ID NO: 6) overexpressed Neuro2a cells (FIG. 8C). We found that 1 g/ml treatment of cA or cC for 2 days significantly reduced G4C2 RNA foci numbers in cells but seldomly changed the CAGG (control probe) RNA foci numbers (FIG. 8D).

We next treated WT Drosophila and Drosophila with GMR-GAL4 driver promoted expression of (G4C2)$_{29}$-repeats (SEQ ID NO: 6) (GMR-GAL4-(G4C2)$_{29}$) (SEQ ID NO: 6) with cA or cC by feeding larvae with compounds in solid food. DMSO was used as a negative control. The eyes of day 7 adult Drosophila with GMR-GAL4-(G4C2)$_{29}$ (SEQ ID NO: 6) were much rougher than the same age WT fly, indicating eye degeneration (FIG. 8E). The affected eye degeneration area accounted for over 50% of the whole eye (FIG. 8F). Intriguingly, cA or cC treatment made the eye much smoother and more reflective (FIG. 8E) compared to the degenerated eye of GMR-GAL4-(G4C2)$_{29}$ (SEQ ID NO: 6) Drosophila, significantly rescuing the eye degeneration phenotype (FIG. 8F).

Example 9—The Permeability, Cytotoxicity and Hemolytic Activity of cA, cB, cC

To evaluate the permeability of compounds cA, cB, cC, we tested these compounds by a parallel artificial membrane permeability assay (PAMPA-09). Using memantine, and nimodipine as positive controls, we found that compound cA showed the best permeability among the three compounds, a similar level to nimodipine (FIG. 9A), while DB1246 showed much worse permeability than cA, cB, cC. In addition, we also tested the permeability on live cells. Neuro2a cells treated with cA at different concentrations (10 µg/ml, 20 µg/ml) for different incubation time (24 h, 48 h) were lysed. Supernatants of cell lysates were collected and analyzed by UPLC-MS. Meanwhile, cell media from different treatment groups were used as control. Compound cA was detected in all groups, while the signal intensity was significantly increased in the 48 h incubation group compared to the 24 h incubation group (FIG. 25, 1-3). In contrast, the intensity of cA signal was the same in the three corresponding cell media groups (FIG. 25, 4-6). These data suggested that cA could penetrate cell membrane and enter into cells.

To evaluate the cytotoxicity of compounds cA, cB and cC, different concentrations (0.1, 1, 10 µg/ml) of these compounds were applied to HEK293T cell lines. Then cell viabilities were measured by MTT assay. Intriguingly, compound cA and cC showed no cytotoxicity up to 10 µg/ml, however, compound cB showed significant cytotoxicity even at a very low dosage, 0.1 µg/ml (FIG. 9B). Moreover, hemolytic activities of cA, cB and cC were measured to evaluate the safety index of these compounds. Coincidentally, both cA and cC showed no hemolytic activity even at the concentration of 1000 μg/ml, while cB showed significant hemolytic activity starting at 500 μg/ml in a dose-dependent manner (FIG. 9C). Taken together, these data suggested that compound cA and cC, with good permeability, without cytotoxicity and hemolytic activity, are better candidates with higher safety index than cB for further evaluations.

Example 10—Compounds cA and cC Rescue Differentiated HT22 Cells from Glutamate Excitotoxicity In the C9orf72 associated ALS/FTD, the G4C2 HRE make motor neurons more vulnerable to aberrant neuron excitation[43]. Meanwhile, the hyperactivation of glutamate receptors drives a toxic level of neuronal activity, promoting the non-ATG (RAN) translation of G4C2 repeat-associated DPR proteins[44], leading to further toxicity of motor neurons. Thus, we would like to test our compounds in a glutamate (E)-induced excitotoxicity cell model. Intriguingly, compound cA and cC significantly rescued differentiated HT22 cells from excitotoxicity-caused death (FIG. 10D). By contrast, cB and cE exacerbated the glutamate-induced cell death compared to the model group, indicating they were cytotoxic, but not neuroprotective (FIG. 10D, FIG. 10H); while cD and cF exhibited neither protective effect nor cytotoxic in the glutamate (E)-induced excitotoxicity cell model (FIG. 10D, FIG. 10H).

Meanwhile, the dose-response relationships of cA, cB, cC, cD, cE and cF were measured. As positive control drugs, memantine, nimodipine and DB1246 were also tested. The $EC_{50}$ of memantine, nimodipine and DB1246 were 23.93, 1.135 and 12.18 μM, respectively (FIGS. 10A-10C); while the $EC_{50}$ of cA, cB, cC, cD, cE were 0.3099, 11.14, 0.03244, 53.57, 1.141e+11 μM, respectively (FIGS. 10E-10G, FIGS. 10I-10K). Among these compounds, only cA showed a good dose-response curve, even better than memantine, indicating its potential of being developed as a neuroprotective compound.

Example 11—Compounds cA, cB, cC, cD, cE and cF all Inhibit Tau-R3 Aggregation In Vitro In the C9orf72 ALS/FTD, there is a strong genetic association between the microtubule-binding protein, tau and the G4C2 HRE. The latter significantly increases aberrant Tau aggregation in *Drosophila* by inhibiting autophagosome-lysosome fusion[45,46]. The co-expression of Tau and G4C2 repeats produces a synergistic deterioration of the neurodegeneration phenotype of ALS/FTD[46]. Considering the tight correlation of Tau aggregation with the ALS/FTD pathogenesis, we tested our compounds in a non-cell-based Tau-R3 aggregation inhibition assay. Using heparin as an inducer and ThT as a probe, cA limited ThT fluorescence significantly (FIG. 11A), suggesting it worked as an inhibitor on the Tau-R3 fibrils aggregation. The inhibition $IC_{50}$ of cA was about 0.3213 μg/ml (FIG. 11B). Both cB and cC inhibited Tau-R3 aggregation with the $IC_{50}$ of 1.302 μg/ml (FIGS. 11C-11D) and 3.677 μg/ml (FIGS. 11E-11F). Moreover, we conducted high magnification TEM imaging to characterize the morphological changes of Tau-R3 fibrils with cA, cB and cC treatments. As shown in FIG. 11G, the Tau-R3 only fibrils were long and compact, and several bundles of fibrils were observed. While with cA (10 μg/ml), cB (5 μg/ml) or cC (10 μg/ml) treatments, the Tau-R3 fibrils were broken into shorter and thinner fragments. Notably, some of the Tau-R3 formed amorphous aggregates (red arrow) in the presence of cA. These data were in accordance with the ThT assay, indicating cA, cB and cC disrupted the Tau-R3 fibril formation in vitro. Also, cD, cE and cF all inhibited Tau-R3 aggregation with $IC_{50}$ of 3.102 μg/ml, 4.083 μg/ml and 2.179 μM (FIGS. 11H-11M). The trend of the inhibition rate of these compounds was different from that in either DNA/RNA G4C2 G-quadruplex binding or neuroprotectivity and hemolytic activity, suggesting a distinct underlying mechanism. Furthermore, the misfolding of tau protein into filaments in neurons of the central nervous system can be found in various neurodegenerative diseases, such as Alzheimer's disease et al. Therefore, the inhibition on tau aggregation represented a potential of cA and its derivatives in targeting multiple other neurodegenerative diseases more than ALS.

Example 12—The Comparison of cA and its Analogs in Bioactivities

Bioactivity differences of these structurally-similar marine natural compounds are compelling. Similar to cA, cB, cC, and cF all bound to DNA $(G4C2)_4$ (SEQ ID NO: 5) G-quadruplex and hnRNP H, while according to the NMR titration experiments, the binding affinity among these three compounds were different, basically like cC>cA>cB>cF (FIGS. 3C-3E). Intriguingly, cC showed better neuroprotective activity than cA, while cB, cD, cE and cF were all worse than cA. In the $(G4C2)_{29}$ (SEQ ID NO: 6)-cells, cC enhanced cell viability from 20% to 40%, and 30% in cA treated group. By contrast, the cB treated group was even worse than the model group (G4C2 29 repeats), indicating potent cytotoxicity other than protectivity (FIG. 8B). Consistent with the G4C2 repeats model, cB and cE also worsened the cell viability in the L-glutamate induced cell death model. Meanwhile, both cA and cC protected cells from excitotoxicity caused death in the L-glutamate cell death model. However, cD and cF neither showed protective effect nor cytotoxicity in the L-glutamate cell death model (FIG. 10D, FIG. 10H). Coincidentally, cA and cC showed no hemolytic activity with a pretty high concentration of 1 mg/ml, while cB showed significant hemolytic activity starting at 0.5 mg/ml in a dose-dependent manner (FIG. 9C).

The intrinsic cause of their bioactivity differences could be attributed to their tiny structure differences. According to the structure difference of cA and its derivatives, cB, cC, as well as cC's derivatives, cD and cE, the structure-activity relationship was evident at a glance. The importance of the hydroxyl group in C-17 was crucial not only for the DNA $(G4C2)_4$ (SEQ ID NO: 5) G-quadruplex binding but also for its neuroprotective activity and hemolytic activity. cB, the methylation product of cA, exhibited significant hemolytic activity and potent cytotoxicity, hence weaken its neuroprotective activity. The hydrophobicity of the adding methyl blocked the hydrogen bond formation between the compound and the DNA $(G4C2)_4$ (SEQ ID NO: 5) G-quadruplex, thus reducing the binding affinity. Compared to cA, the double bonds were opened and one more hydroxyl group was added to the C-4' at the glucuronic acid of cC, which was beneficial to its binding to G-quadruplex and neuroprotective effects on cells. cD and cE, methylation products of cC, showed cytotoxicity as well. Therefore, these data suggested that the hydroxyl groups replaced by methyl groups was highly associated with the cytotoxicity of this compound series.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Chen, W. W., Zhang, X. & Huang, W. J. Role of neuroinflammation in neurodegenerative diseases (Review). Mol Med Rep 13, 3391-3396 (2016).
2. Scheltens, P., et al. Alzheimer's disease. The Lancet 388, 505-517 (2016).
3. Hardiman, O., et al. Amyotrophic lateral sclerosis. Nat Rev Dis Primers 3, 17071 (2017).
4. Poewe, W., et al. Parkinson disease. Nat Rev Dis Primers 3, 17013 (2017).
5. Long, J. M. & Holtzman, D. M. Alzheimer Disease: An Update on Pathobiology and Treatment Strategies. Cell 179, 312-339 (2019).
6. Hou, Y., et al. Ageing as a risk factor for neurodegenerative disease. Nat Rev Neurol 15, 565-581 (2019).
7. Eratne, D., et al. Alzheimer's disease: clinical update on epidemiology, pathophysiology and diagnosis. Australas Psychiatry 26, 347-357 (2018).
8. Lopez, O. L. & Kuller, L. H. Epidemiology of aging and associated cognitive disorders: Prevalence and incidence of Alzheimer's disease and other dementias. Handb Clin Neurol 167, 139-148 (2019).
9. Garre-Olmo, J. [Epidemiology of Alzheimer's disease and other dementias]. Rev Neurol 66, 377-386 (2018).
10. Tysnes, O. B. & Storstein, A. Epidemiology of Parkinson's disease. J Neural Transm (Vienna) 124, 901-905 (2017).
11. Abbas, M. M., Xu, Z. & Tan, L. C. S. Epidemiology of Parkinson's Disease-East Versus West. Mov Disord Clin Pract 5, 14-28 (2018).
12. Rafii, M. S. & Aisen, P. S. Advances in Alzheimer's disease drug development. BMC Med 13, 62 (2015).
13. Hung, S. Y. & Fu, W. M. Drug candidates in clinical trials for Alzheimer's disease. J Biomed Sci 24, 47 (2017).
14. Witt, A., Macdonald, N. & Kirkpatrick, P. Memantine hydrochloride. Nat Rev Drug Discov 3, 109-110 (2004).
15. Reisberg, B., et al. Memantine in moderate-to-severe Alzheimer's disease. N Engl J Med 348, 1333-1341 (2003).
16. Popovic, M., Caballero-Bleda, M., Popovic, N., Bokonjic, D. & Dobric, S. Neuroprotective effect of chronic verapamil treatment on cognitive and noncognitive deficits in an experimental Alzheimer's disease in rats. Int J Neurosci 92, 79-93 (1997).
17. Albarran, M. T., Lopez-Burillo, S., Pablos, M. I., Reiter, R. J. & Agapito, M. T. Endogenous rhythms of melatonin, total antioxidant status and superoxide dismutase activity in several tissues of chick and their inhibition by light. J Pineal Res 30, 227-233 (2001).
18. Charvin, D., Medori, R., Hauser, R. A. & Rascol, O. Therapeutic strategies for Parkinson disease: beyond dopaminergic drugs. Nat Rev Drug Discov 17, 804-822 (2018).
19. Kuller, L. H. A new era for dementia epidemiology: Alzheimer's disease, hardening of arteries, or just old age? Eur J Epidemiol 33, 613-616 (2018).
20. Harvey, A. L., Edrada-Ebel, R. & Quinn, R. J. The re-emergence of natural products for drug discovery in the genomics era. Nat Rev Drug Discov 14, 111-129 (2015).
21. Haefner, B. Drugs from the deep: marine natural products as drug candidates. Drug Discov Today 8, 536-544 (2003).
22. Xiao, G., Shao, X., Zhu, D. & Yu, B. Chemical synthesis of marine saponins. Nat Prod Rep 36, 769-787 (2019).
23. He, W., Zhang, Z. & Ma, D. A Scalable Total Synthesis of the Antitumor Agents Et-743 and Lurbinectedin. Angew Chem Int Ed Engl 58, 3972-3975 (2019).
24. Yamada, Y. [Studies on discovery and synthesis of bioactive marine organic molecules]. Yakugaku Zasshi 122, 727-743 (2002).
25. Pravin Shinde, P. B., Anita Mandhare Marine natural products as source of new drugs: a patent review (2015-2018). Expert Opinion on Therapeutic Patents 29, 283-309 (2019).
26. H. Blasco, S. M., P. Corcia and P. H. Gordon. The Glutamate Hypothesis in ALS-Pathophysiology and Drug Development. Current Medicinal Chemistry 21, 3551-3575 (2014).
27. Mehta, A., Prabhakar, M., Kumar, P., Deshmukh, R. & Sharma, P. L. Excitotoxicity: bridge to various triggers in neurodegenerative disorders. Eur J Pharmacol 698, 6-18 (2013).
28. Dong, X. X., Wang, Y. & Qin, Z. H. Molecular mechanisms of excitotoxicity and their relevance to pathogenesis of neurodegenerative diseases. Acta Pharmacol Sin 30, 379-387 (2009).
29. Balendra, R. & Isaacs, A. M. C9orf72-mediated ALS and FTD: multiple pathways to disease. Nat Rev Neurol 14, 544-558 (2018).
30. Kumar, V., Hasan, G. M. & Hassan, M. I. Unraveling the Role of RNA Mediated Toxicity of C9orf72 Repeats in C9-FTD/ALS. Front Neurosci 11, 711 (2017).
31. Mazanetz, M. P. & Fischer, P. M. Untangling tau hyperphosphorylation in drug design for neurodegenerative diseases. Nat Rev Drug Discov 6, 464-479 (2007).
32. Julien, J. P. Amyotrophic lateral sclerosis. unfolding the toxicity of the misfolded. Cell 104, 581-591 (2001).
33. Schneider, A. & Mandelkow, E. Tau-based treatment strategies in neurodegenerative diseases. Neurotherapeutics 5, 443-457 (2008).
34. Cammas, A. & Millevoi, S. RNA G-quadruplexes: emerging mechanisms in disease. Nucleic acids research 45, 1584-1595 (2017).
35. Kumar, V., Kashav, T., Islam, A., Ahmad, F. & Hassan, M. I. Structural insight into C9orf72 hexanucleotide repeat expansions: Towards new therapeutic targets in FTD-ALS. Neurochem Int 100, 11-20 (2016).
36. Mauger, D. M., Lin, C. & Garcia-Blanco, M. A. hnRNP H and hnRNP F complex with Fox2 to silence fibroblast growth factor receptor 2 exon IIIc. Mol Cell Biol 28, 5403-5419 (2008).
37. Lee, Y. B., et al. Hexanucleotide repeats in ALS/FTD form length-dependent RNA foci, sequester RNA binding proteins, and are neurotoxic. Cell Rep 5, 1178-1186 (2013).
38. Zhou, B., et al. Characterizations of distinct parallel and antiparallel G-quadruplexes formed by two-repeat ALS and FTD related GGGGCC sequence. Sci Rep 8, 2366 (2018).
39. Zhou, B., Liu, C., Geng, Y. & Zhu, G. Topology of a G-quadruplex DNA formed by C9orf72 hexanucleotide repeats associated with ALS and FTD. Sci Rep 5, 16673 (2015).

40. Liu, C., et al. A chair-type G-quadruplex structure formed by a human telomeric variant DNA in K(+) solution. Chem Sci 10, 218-226 (2019).
41. Liu, C., et al. G-quadruplex structures formed by human telomeric DNA and C9orf72 hexanucleotide repeats. Biophys Rev 11, 389-393 (2019).
42. Simone, R., et al. G-quadruplex-binding small molecules ameliorate C9orf72 FTD/ALS pathology in vitro and in vivo. EMBO Mol Med 10, 22-31 (2018).
43. Selvaraj, B. T., et al. C9ORF72 repeat expansion causes vulnerability of motor neurons to Ca2+-permeable AMPA receptor-mediated excitotoxicity. Nat Commun 9(2018).
44. Westergard, T., et al. Repeat-associated non-AUG translation in C9orf72-ALS/FTD is driven by neuronal excitation and stress. EMBO Mol Med 11(2019).
45. Wen, X., et al. Tau Accumulation via Reduced Autophagy Mediates GGGGCC Repeat Expansion-Induced Neurodegeneration in Drosophila Model of ALS. Neurosci Bull (2020).
46. He, H., et al. Amyotrophic Lateral Sclerosis-associated GGGGCC repeat expansion promotes Tau phosphorylation and toxicity. Neurobiol Dis 130, 104493 (2019).
47. Kondo, K., Eguchi, T., Kakinuma, K., Mizoue, K. & Qiao, Y. F. Structure and biosynthesis of FD-594; a new antitumor antibiotic. J Antibiot 51, 288-295 (1998).
48. Kang, H. S. & Brady, S. F. Arixanthomycins A-C: Phylogeny-Guided Discovery of Biologically Active eDNA-Derived Pentangular Polyphenols. Acs Chemical Biology 9, 1267-1272 (2014).
49. Kang, H. S. & Brady, S. F. Mining Soil Metagenomes to Better Understand the Evolution of Natural Product Structural Diversity: Pentangular Polyphenols as a Case Study. Journal of the American Chemical Society 136, 18111-18119 (2014).
50. Wang, P., Zhang, W. J., Zhan, J. X. & Tang, Y. Identification of OxyE as an Ancillary Oxygenase during Tetracycline Biosynthesis. Chembiochem 10, 1544-1550 (2009).
51. Gao, C. Z., et al. Hexaricins, Pradimicin-like Polyketides from a Marine Sediment-Derived Streptosporangium sp and Their Antioxidant Effects. J Nat Prod 81, 2069-2074 (2018).
52. Dorst, J., Ludolph, A. C. & Huebers, A. Disease-modifying and symptomatic treatment of amyotrophic lateral sclerosis. Ther Adv Neurol Disord 11, 1756285617734734 (2018).
53. Donnelly, C. J., et al. RNA toxicity from the ALS/FTD C9ORF72 expansion is mitigated by antisense intervention. Neuron 80, 415-428 (2013).
54. Starr, A. & Sattler, R. Synaptic dysfunction and altered excitability in C9ORF72 ALS/FTD. Brain Res 1693, 98-108 (2018).
55. Yuva-Aydemir, Y., Almeida, S. & Gao, F. B. Insights into C9ORF72-Related ALS/FTD from Drosophila and iPSC Models. Trends Neurosci 41, 457-469 (2018).
56. Selvaraj, B. T., Livesey, M. R. & Chandran, S. Modeling the C9ORF72 repeat expansion mutation using human induced pluripotent stem cells. Brain Pathol 27, 518-524 (2017).
57. DeJesus-Hernandez, M., et al. Expanded GGGGCC Hexanucleotide Repeat in Noncoding Region of C9ORF72 Causes Chromosome 9p-Linked FTD and ALS. Neuron 72, 245-256 (2011).
58. Xu, W. & Xu, J. C9orf72 Dipeptide Repeats Cause Selective Neurodegeneration and Cell-Autonomous Excitotoxicity in Drosophila Glutamatergic Neurons. J Neurosci 38, 7741-7752 (2018).
59. Dong, W., et al. Ablation of C9orf72 together with excitotoxicity induces ALS in rats. FEBS J 288, 1712-1723 (2021).
60. Wang, E., Thombre, R., Shah, Y., Latanich, R. & Wang, J. G-Quadruplexes as pathogenic drivers in neurodegenerative disorders. Nucleic acids research (2021).
61. G. M. Morris, D. S. G., R. S. Halliday, R. Huey, W. E. Hart, R. K. Belew, A. J. Olson. Automated Docking Using a LamarckianGenetic Algorithm and an EmpiricalBinding Free Energy Function. J. Comput. Chem. 19, 1639-1662 (1998).

We claim:

1. A compound of formula (IV), formula (V), formula (VI), formula (VII), formula (VIII), or formula (IX):

formula (IV)
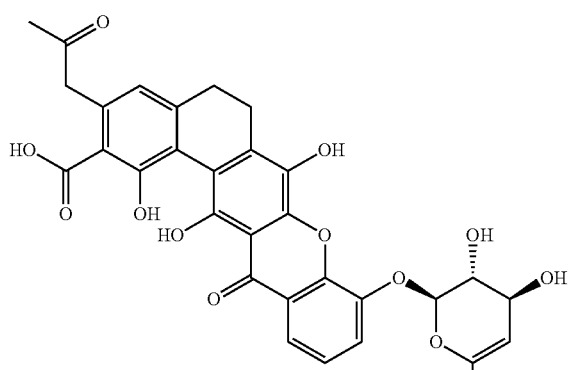

formula (V)
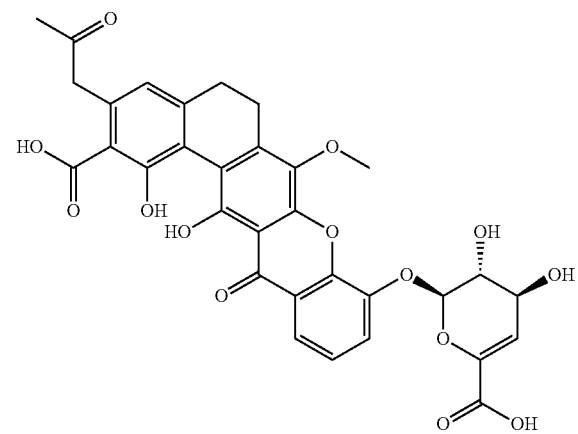

formula (VI)
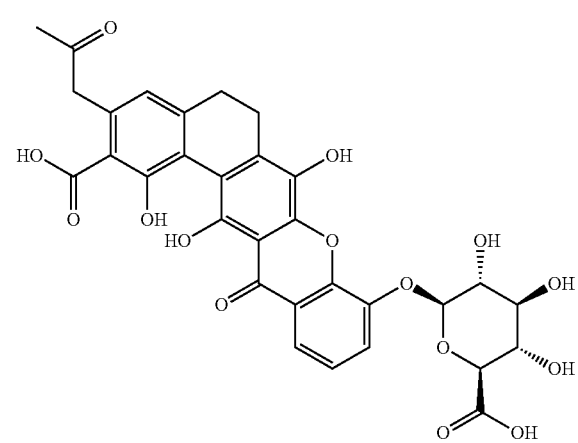

formula (VII)
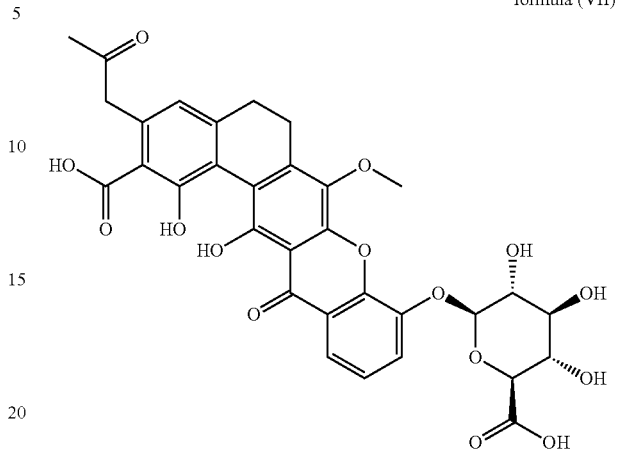

formula (VIII)
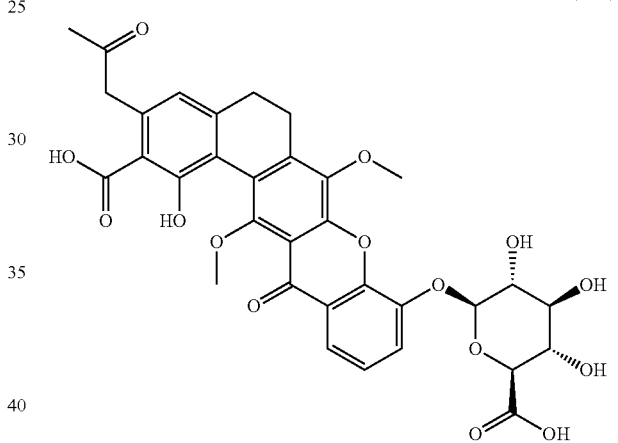

formula (IX)
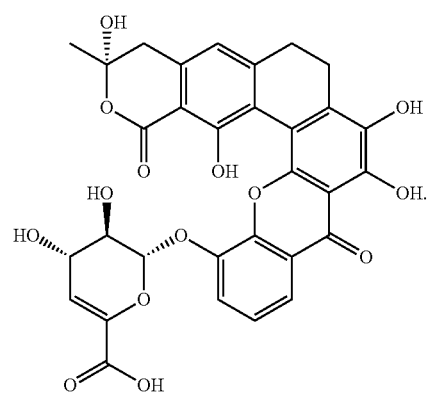

2. A composition comprising the compound of claim 1 and a pharmaceutically acceptable carrier and/or excipient.

3. A method of binding to a G-quadruplex (G4), RRM domain of RNA binding protein hnRNP H, or DNA binding proteins hnRNP F or hORC6, the method comprising administering the compound of formula (IV), formula (V), formula (VI), formula (VII), formula (VIII), or formula (IX) to a subject, wherein the subject has a neurodegenerative disease:

formula (IV):

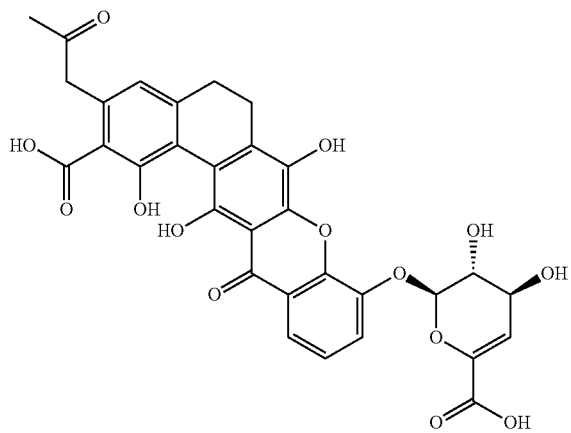

formula (V)

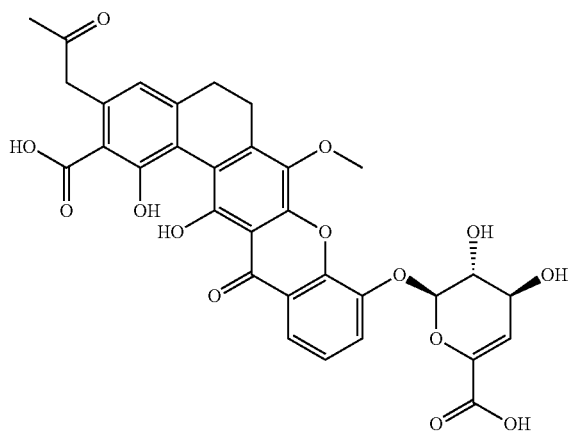

formula (VI)

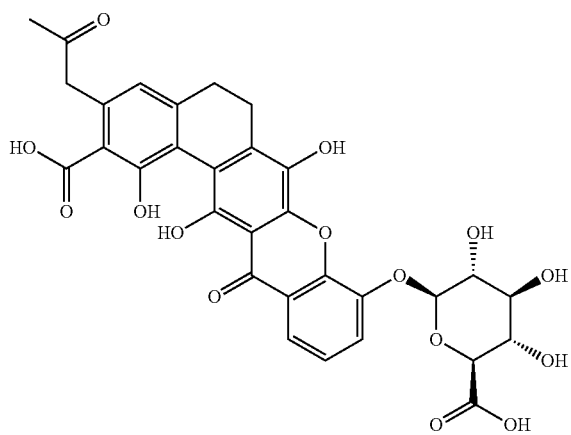

-continued formula (VII)

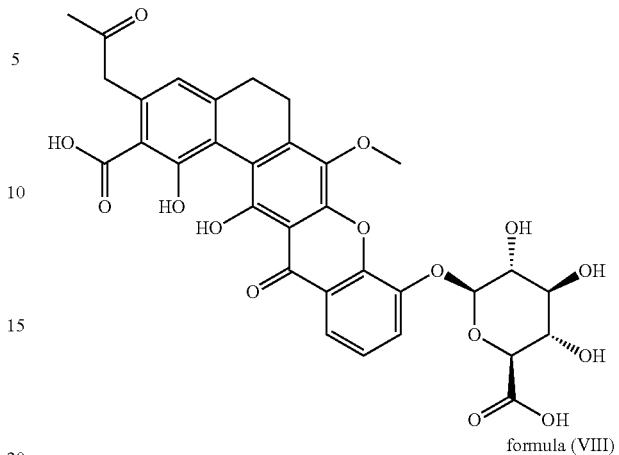

formula (VIII)

formula (IX)

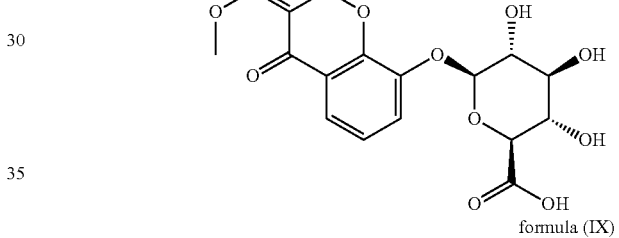

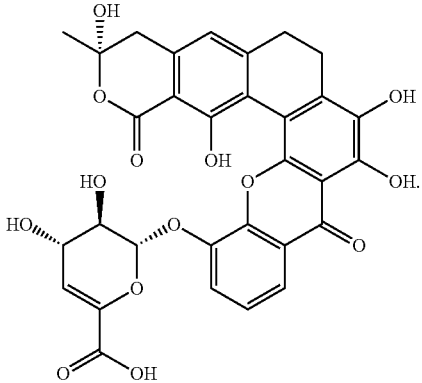

4. The method of claim 3, wherein a route of administration is intravenous injection or oral administration.

5. The method of claim 3, wherein the compound of formula (IV), formula (V), formula (VI), formula (VII), formula (VIII), or formula (IX) crosses the blood brain barrier.

6. The method of claim 5, further comprising the compound of formula (IV), formula (V), formula (VI), formula (VII), formula (VIII), or formula (IX) entering or contacting neuronal cells.

7. The method of claim 3, wherein the G4 is DNA (G4C2)4 (SEQ ID NO: 5) or RNA (G4C2)2 (SEQ ID NO: 8).

8. The method of claim 3, further comprising reducing glutamate-induced excitotoxicity of neuronal cells.

9. The method of claim 3, further comprising inhibiting or eliminating tau aberrant aggregation.

10. The method of claim 9, wherein the tau aberrant aggregation is tau fibril formation, tau oligomer formation, and/or tau protofibril formation.

11. The method of claim 3, wherein the neurodegenerative disease is Alzheimer's disease (AD), Parkinson's disease (PD), amyotrophic lateral sclerosis (ALS), Huntington's disease (HD), multiple sclerosis, epilepsy, stroke, alcohol withdrawal, progressive supranuclear palsy (PSP), Pick's disease (PiD), corticobasal degeneration (CBD), frontotemporal dementia or parkinsonism linked to chromosome 17 (FTDP-17).

12. A method of blocking DNA replication, the method comprising administering the compound of formula (IV), formula (V), formula (VI), formula (VII), formula (VIII), or formula (IX) to a subject, wherein the compound of formula (IV), formula (V), formula (VI), formula (VII), formula (VIII), or formula (IX) binds to human ORC6 protein:

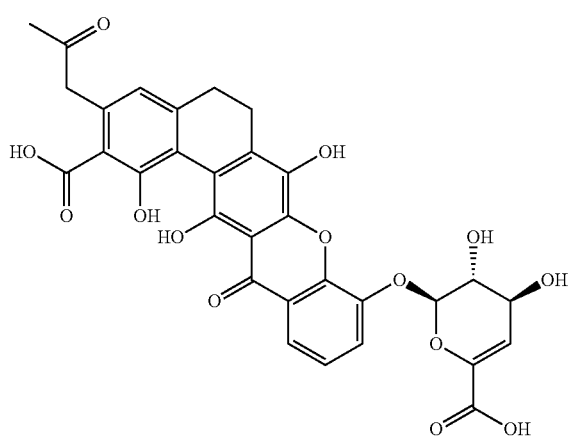

formula (IV)

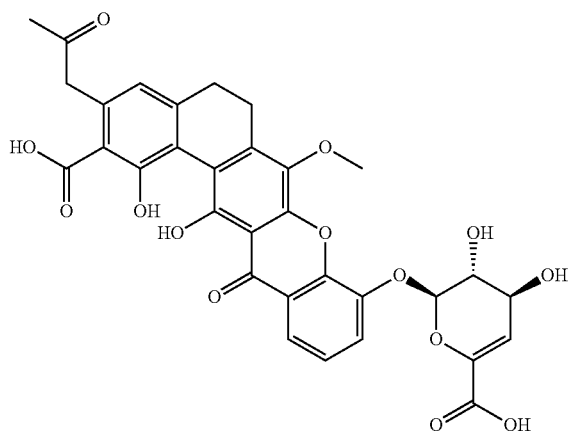

formula (V)

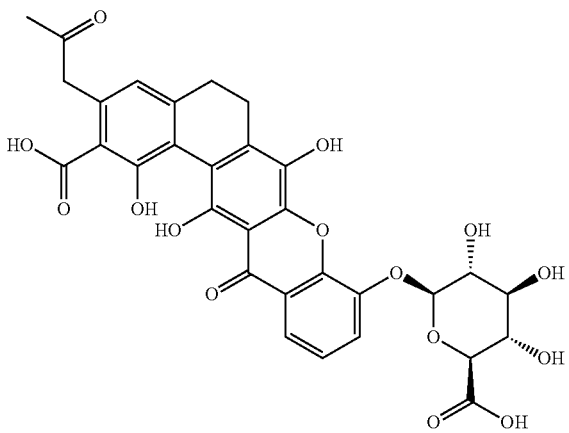

formula (VI)

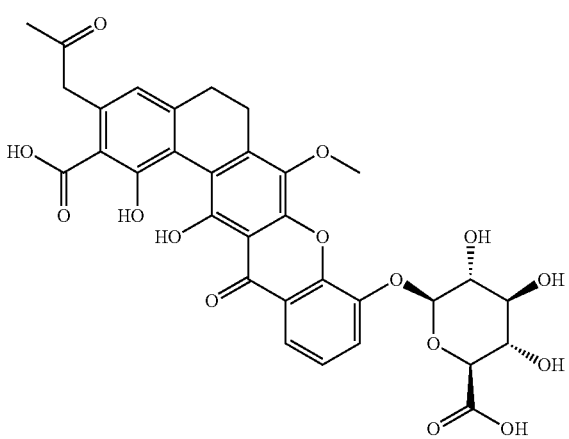

formula (VII)

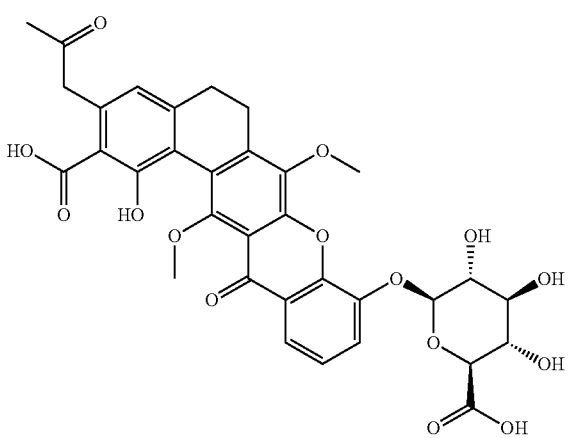

formula (VIII)

-continued
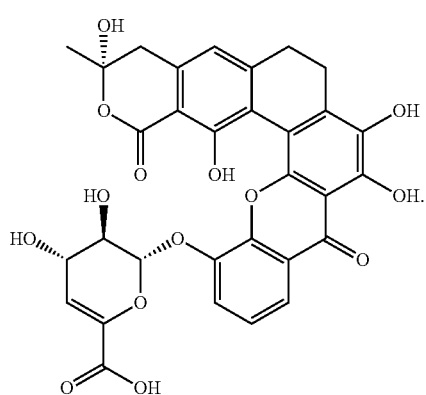
formula (IX)
* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Target probe

<400> SEQUENCE: 1
ggccccggcc ccggccccgg cccc                                    24

<210> SEQ ID NO 2
<211> LENGTH: 20
<212> TYPE: DNA
<213> ORGANISM: Artificial Sequence
<220> FEATURE:
<223> OTHER INFORMATION: Control probe

<400> SEQUENCE: 2
caggcaggca ggcaggcagg                                         20

<210> SEQ ID NO 3
<211> LENGTH: 21

```
<212> TYPE: DNA
<213> ORGANISM: Homo sapiens

<400> SEQUENCE: 3
gggttagggt tagggtttgg g                                            21

<210> SEQ ID NO 4
<211> LENGTH: 12
<212> TYPE: DNA
<213> ORGANISM: Homo sapiens

<400> SEQUENCE: 4
ggggccgggg cc                                                      12

<210> SEQ ID NO 5
<211> LENGTH: 24
<212> TYPE: DNA
<213> ORGANISM: Homo sapiens

<400> SEQUENCE: 5
ggggccgggg ccggggccgg ggcc                                         24

<210> SEQ ID NO 6
<211> LENGTH: 174
<212> TYPE: DNA
<213> ORGANISM: Homo sapiens

<400> SEQUENCE: 6
ggggccgggg ccggggccgg ggccggggcc ggggccgggg ccggggccgg ggccggggcc   60
ggggccgggg ccggggccgg ggccggggcc ggggccgggg ccggggccgg ggccggggcc  120
ggggccgggg ccggggccgg ggccggggcc ggggccgggg ccggggccgg ggcc        174

<210> SEQ ID NO 7
<211> LENGTH: 23
<212> TYPE: DNA
<213> ORGANISM: Homo sapiens

<400> SEQUENCE: 7
tagggttagg gttagggtta ggg                                          23

<210> SEQ ID NO 8
<211> LENGTH: 12
<212> TYPE: RNA
<213> ORGANISM: Homo sapiens

<400> SEQUENCE: 8
ggggccgggg cc                                                      12
```